US005612201A

United States Patent [19]
De Plaen et al.

[11] Patent Number: 5,612,201
[45] Date of Patent: *Mar. 18, 1997

[54] ISOLATED NUCLEIC ACID MOLECULES USEFUL IN DETERMINING EXPRESSION OF A TUMOR REJECTION ANTIGEN PRECURSOR

[75] Inventors: Etienne De Plaen; Thierry Boon-Falleur; Bernard Lethé; Jean-Pierre Szikora; Charles De Smet; Patrick Chomez, all of Brussels, Belgium

[73] Assignee: Ludwig Institute for Cancer Research, New York, N.Y.

[*] Notice: The term of this patent shall not extend beyond the expiration date of Pat. No. 5,512,444.

[21] Appl. No.: 299,849

[22] Filed: Sep. 1, 1994

Related U.S. Application Data

[63] Continuation-in-part of Ser. No. 37,230, filed as PCT/US92/04354, May 22, 1992, which is a continuation-in-part of Ser. No. 807,043, Dec. 12, 1991, Pat. No. 5,342,774, which is a continuation-in-part of Ser. No. 764,364, Sep. 23, 1991, Pat. No. 5,327,252, which is a continuation-in-part of Ser. No. 728,838, Jul. 9, 1991, abandoned, which is a continuation-in-part of Ser. No. 705,702, May 23, 1991, abandoned.

[51] Int. Cl.$^6$ .............................. C12P 19/34; C12Q 1/68; C07H 21/02; C07H 21/04
[52] U.S. Cl. ........................... 435/91.2; 435/6; 536/23.1; 536/24.33
[58] Field of Search ........................ 435/6, 91.2; 536/23.1, 536/24.3–24.33

[56] References Cited

U.S. PATENT DOCUMENTS 5,342,774   8/1994   Boon et al. .......................... 435/240.2

FOREIGN PATENT DOCUMENTS

WO9220356   11/1992   WIPO .

OTHER PUBLICATIONS

Van der Bruggen et al., "A Gene Encoding an Antigen Recognized By Cytolytic T Lymphocytes on Human Melanoma", Science 254: 1643–1657 (Dec. 1991).

Brasseur et al., "Human gene MAGE–1, which codes for a tumor rejection antigen, is expressed by some breast tumors", Int. J. Cancer 42: 839–841 (1992).

DeSmet et al., "Sequence and expression pattern of the human MAGE 2 gene", Immunogenetics 39: 121–129 (1994).

Gaugler et al., "Human Gene MAGE–3 Codes For An Antigen Recognized on a Melanoma by Autologous Cytolytic T Lymphocytes", J. Exp. Med. 179: 921–930 (Mar., 1994).

*Primary Examiner*—Stephanie W. Zitomer
*Assistant Examiner*—Dianne Rees
*Attorney, Agent, or Firm*—Felfe & Lynch

[57] ABSTRACT

The invention relates to nucleic acid molecules which are useful in determining expression of the family of molecules known as the MAGE tumor rejection antigen precursors. These nucleic acid are molecules useful as diagnostic aids for determining whether or not an individual has cancer. Methods using these molecules are also described.

3 Claims, 19 Drawing Sheets

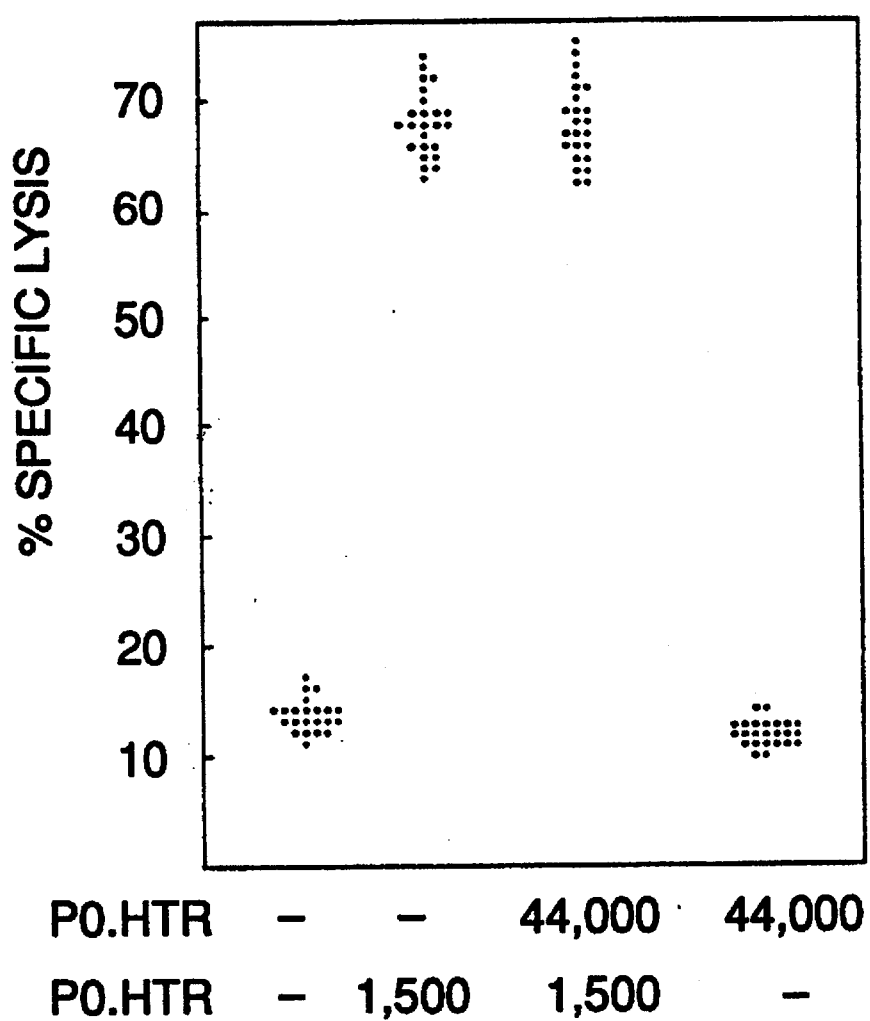

FIG. 9

```
MAGE-3 III    CCTCCCCAGAGTCCTCAGGGAGAGCCCTCCagCcTtcCCACTACCATGaACTaCcCTTCtctgGAGcCAAtCCtatGAGGacTCCAGCaaCTCCAGCAaCCaaGAAGAGGAGG
                                                                                                              →
                                                                                                              CHO-3
MAGE-2 II     CCTCCCCAcAGTCCTCAGGGAGAGCCCTCCagCTTctCgACTACCATCAACTaCACTCTttgGAGaCAAtCCttgAGaCAAtGAGGGCTCCAGCaTGAGGGCTCCAGCAaCCaaGAAGAGGAGG
                                                                                                              →
                                                                                                              CHO-2
MAGE-1 I      CCTCCCCAGAGTCCTCAGGGAGAGCCCTCCGCGCCTTTCCCACTACCATCAACTTCACTCGACAGAGGCAACCCAGTGAGGGTTCCAGCAGCCGTGAAGAGGAGG
              225  CHO-8
                →

III GGCCAAGCACCTtcccTgaCC-TGGAGTCCgaTTCCaAGCAGCaCTCagTAGgAAGGTGGCCGAgTTGGTTcaTTTCTGCTCCTCAAgTATCGAGCCA
          II  GGCCAAGaAtgTtTcccgaCCtTGGAGTCCtGGAGTCCaAGCAGCaATCagTAGgAAGaTGGtTGAgTTGGTtcaTTTCTGCTCCTCAAgTATCGAGCCA
          I   GGCCAAGCACCTCTTgTATCC-TGGAGTCCTTGTTCCGAGCAGTAATCACTAAGAAGGTGGCTGATTTGGTTGGTTTCTGCTCCTCAAATATCGAGCCA
              325

III GGGAGCCggTCACAAAGGCAGAAATGCTGGgGAGTGTCgTCggAAATTggCAGtAtTtcTTTCCTgtGATCTTCAGCAAAGCTTCcagtTCCTTGCAGCT
          II  GGGAGCCggTCACAAAGGCAGAAATGCTGAGAGTGTCCTCAGAAATTgCCAGGaCTtcTTTCCgtGATCTTCAGCAAAGCCTCCGAGTaCTTGCAGCT
          I   GGGAGCCAGTCACAAAGGCAGAAATGCTGAGAGTGTCATCAAAAATTACAAGCACTGTTTCTCGAGATCTTCGGCAAAGCCTCTGAGTCCTTGCAGCT
              425                                                                  SEQ-4
                                                                                    →

III GGTCTTTGGCATcGAgcTGAtGGAAGtgGACCCCAtGACCCGGcCACTCtgTAcaTCt-TTGcCACCTGCCTGGCcCTCCTCCTACGATGCCTGCTGGGTGACAAT
          II  GGTCTTTGGCATcGAgTGCATGGAAGtgtGCCCCAtCAGCCACTCtgTAcaTCCTTGTCACCTGCCTGGCcCTCCTCCTACGATGCCTGCTGGGCGACAAT
          I   GGTCTTTGGCATTGACGTGAAGGAAGCAGACCCACCGGCCACTCCTATGTCCTTGTCACCTGCCTAGTCTCTCCTATGATGCCTGCTGGGTGATAAT
              525

III CAGATCAATGCCAAGgCAGGCcTTCCTGATAAtcGTCTGGcCATaAtCGAagaGAGGGCGaCtgTGCcCCTGAGGAGaAAATCGGAGGAGCTGAGTG
          II  CAGgTCATGCCCAAGACAGGCcTCCTGATAATcGTC-TGGCCATaAAtCGAATaGAGGGCGaCtgTGCcCCTGAGGAGaAAATCGGAGGAGCTGAGTa
          I   CAGATCAATGCCAAGACAGCAGGCTTCCTGATAATTGTCCTGGTCATGATTGCAATGAGGGGCGGCCATGCTCCTGAGGAGGAGAAATCGGGAGGAGCTGAGTG
              625                                                                                    CHO-9
                                                                                                      ←
```

FIG. 11A

| | Northern blot probed with cross-reactive MAGE-1 probe* | EXPRESSION OF MAGE GENE FAMILY cDNA-PCR product probed with oligonucleotide specific for: | | | RECOGNITION BY ANTI-E CTL tested by: | | Expression of antigen MZ2-E after transfection** |
|---|---|---|---|---|---|---|---|
| | | MAGE-1 MAGE-2 MAGE-3† | | | TNF release‡ | Lysis§ | |
| Cells of patient MZ2 | | | | | | | |
| melanoma cell line MZ2-MEL.3.0 | + | +++ | +++ | +++ | + | + | |
| tumor sample MZ2 (1982) | + | +++ | +++ | +++ | | | |
| antigen-loss variant MZ2-MEL.2.2 | + | − | − | +++ | − | − | |
| CTL clone MZ2-CTL.82/30 | − | − | − | − | | | |
| PHA-activated blood lymphocytes | − | − | − | − | | | |
| Normal tissues | | | | | | | |
| Liver | − | − | − | − | | | |
| Muscle | − | − | − | − | | | |
| Skin | − | − | − | − | | | |
| Lung | − | − | − | − | | | |
| Brain | − | − | − | − | | | |
| Kidney | − | − | − | − | | | |
| Melanoma cell lines of HLA-A1 patients | | | | | | | |
| LB34-MEL | + | ++ | +++ | +++ | + | +− | ++ |
| MI665/2-MEL | − | − | − | − | − | − | ++ |
| MI10221-MEL | + | − | ++ | +++ | − | − | |
| MI13443-MEL | + | +++ | +++ | +++ | + | + | −+ |
| SK33-MEL | + | − | +++ | +++ | − | − | |
| SK23-MEL | + | − | +++ | +++ | − | − | |

\* Data obtained in the conditions of figure 5.
† Data obtained as described in figure 6.
‡ TNF release by CTL 82/30 after stimulation with the tumor cells as described in (11).
§ Lysis of 51 Cr labelled target by CTL 82/30 in the conditions of figure 1.
\*\* Cells transfected with the 2.4 kb fragment of gene MAGE-1 were tested for their ability to stimulate TNF release by CTL 82/30

FIG. 11B

| | | EXPRESSION OF MAGE GENE FAMILY | | | | RECOGNITION BY ANTI-E CTL | | Expression of antigen MZ2-E after transfection** |
|---|---|---|---|---|---|---|---|---|
| | | Northern blot probed with cross-reactive MAGE-1 probe* | cDNA-PCR product probed with oligonucleotide specific for: | | | tested by: | | |
| | | | MAGE-1 | MAGE-2 | MAGE-3† | TNF release‡ | Lysis§ | |
| Melanoma cell lines of other patients | LB17-MEL | + | + | +++ | +++ | – | – | – |
| | LB33-MEL | + | – | +++ | +++ | – | – | – |
| | LB4-MEL | – | – | – | – | – | – | |
| | LB41-MEL | – | – | – | – | – | – | |
| | MI4024-MEL | + | +++ | +++ | +++ | – | – | |
| | SK29-MEL | – | – | – | – | – | – | |
| | MZ3-MEL | + | + | +++ | +++ | – | – | |
| | MZ5-MEL | + | – | +++ | +++ | – | – | |
| Melanoma tumor sample | BB5-MEL | + | +++ | ++ | +++ | – | – | |
| Other tumor cell lines | small cell lung cancer H209 | + | – | +++ | +++ | | – | |
| | small cell lung cancer H345 | + | – | +++ | +++ | | – | |
| | small cell lung cancer H510 | + | – | +++ | +++ | | – | |
| | small cell lung cancer LB11 | + | + | +++ | +++ | | – | |
| | bronchial squamous cell carcinoma LB37 | + | – | +++ | +++ | | – | |
| | thyroid medullary carcinoma TT | + | +++ | ++ | ++ | | – | |
| | colon carcinoma LB31 | + | – | ++ | +++ | – | – | |
| | colon carcinoma LS411 | – | – | – | – | – | – | |
| Other tumor samples | chronic myeloid leukemia LLC5 | – | – | – | – | – | – | |
| | acute myeloid leukemia TA | – | – | – | – | – | – | |

\* Data obtained in the conditions of figure 5.
† Data obtained as described in figure 6.
‡ TNF release by CTL 82/30 after stimulation with the tumor cells as described in (11).
§ Lysis of 51 Cr labelled target by CTL 82/30 in the conditions of figure 1.
** Cells transfected with the 2.4 kb fragment of gene MAGE-1 were tested for their ability to stimulate TNF release by CTL 82/30

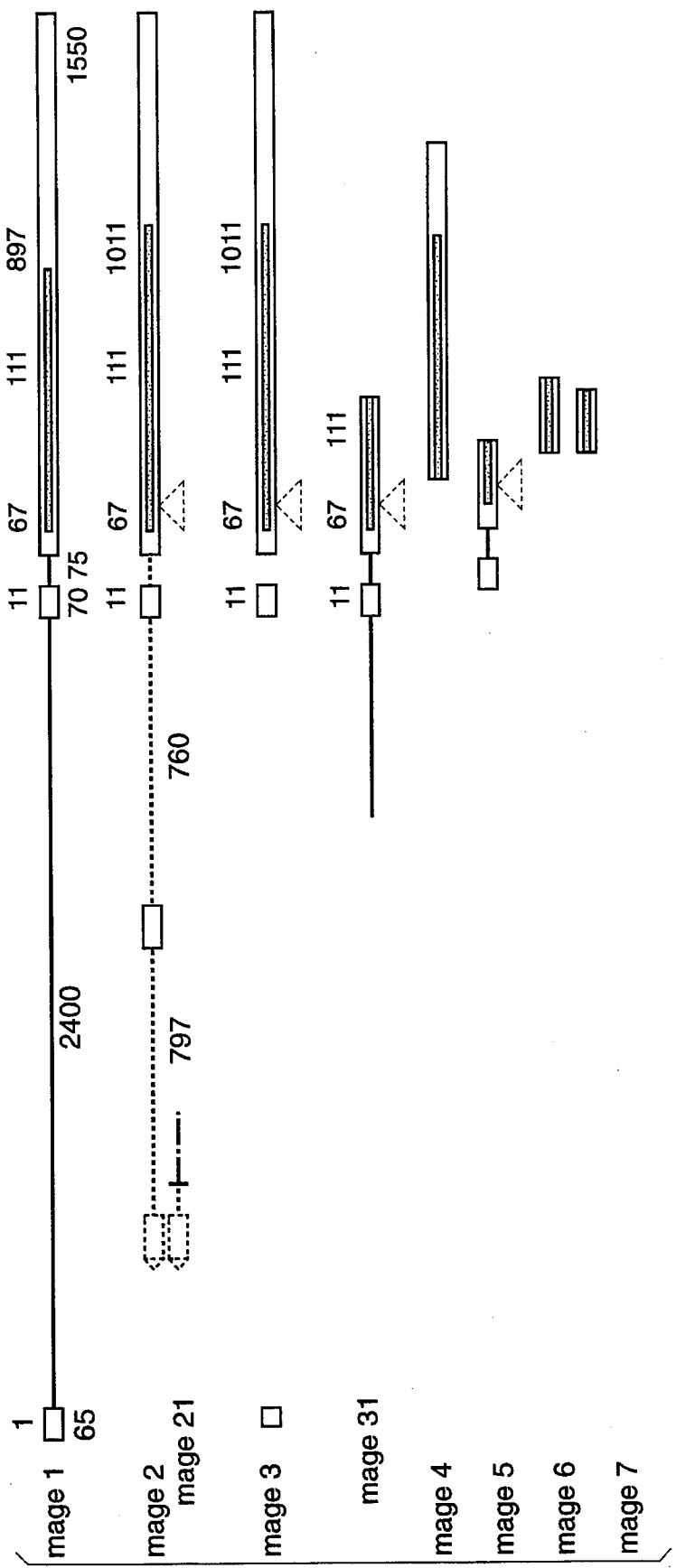

ISOLATED NUCLEIC ACID MOLECULES USEFUL IN DETERMINING EXPRESSION OF A TUMOR REJECTION ANTIGEN PRECURSOR

RELATED APPLICATION

This application is a continuation-in-part of Ser. No. 08/037,230, filed Mar. 26, 1993, which is a continuation-in-part of PCT Application PCT/US92/04354 filed on May 22, 1992 designating the United States, which is a continuation-in-part of Ser. No. 07/807,043, filed Dec. 12, 1991, now U.S. Pat. No. 5,342,774 which is a continuation-in-part of Ser. No. 07/764,364, filed Sep. 23, 1991, now U.S. Pat. No. 5,327,252, which is a continuation-in-part of Ser. No. 07/728,838, filed Jul. 9, 1991, now abandoned, which is a continuation-in-part of Ser. No. 07/705,702, filed May 23, 1991, and now abandoned.

FIELD OF THE INVENTION

This invention relates in general to the field of immunogenetics as applied to the study of oncology. More specifically, it relates to the study and analysis of mechanisms by which tumors are recognized by the organism's immune system such as through the presentation of so-called tumor rejection antigens, and the expression of what will be referred to herein as "tumor rejection antigen precursors" or "TRAPs". Most specifically, it refers to nucleic acid molecules useful in determining expression of tumor rejection antigen precursors, or "TRAPs", via amplification assays such as the polymerase chain reaction ("PCR"), or other amplification systems, and standard hybridization assays.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18:769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum⁻ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum⁻ antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See Boon et al., Proc. Natl. Acad. Sci. U.S.A. 74: 272 (1977), the disclosure of which is incorporated by reference. Many tumor types have been shown to exhibit this phenomenon. See, e.g., Frost et al., Cancer Res. 43: 125 (1983).

It appears that tum⁻ variants fail to form progressive tumors because they elicit an immune rejection process. The evidence in favor of this hypothesis includes the ability of "tum⁻" variants of tumors, i.e., those which do not normally form tumors, to do so in mice with immune systems suppressed by sublethal irradiation, Van Pel et al., Proc. Natl, Acad. Sci. U.S.A. 76: 5282–5285 (1979); and the observation that intraperitoneally injected tum⁻ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum⁻ variant, even when immunosuppressive amounts of radiation are administered with the following challenge of cells (Boon et al., Proc. Natl, Acad. Sci. U.S.A. 74: 272–275 (1977); Van Pel et al., supra; Uyttenhove et al., supra). Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearson et al., Cancer Res. 48: 2975–1980 (1988) in this regard.

A class of antigens has been recognized which are presented on the surface of tumor cells and are recognized by cytotoxic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLs, including minor histocompatibility antigens, the male specific H-Y antigens, and a class of antigens, referred to as "tum⁻" antigens, and discussed herein.

A tumor exemplary of the subject matter described supra is known as P815. See DePlaen et al., Proc. Natl. Acad. Sci. U.S.A. 85: 2274–2278 (1988); Szikora et al., EMBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum⁻ variants following mutagenesis, including variants referred to as P91A (DePlaen, supra), 35B (Szikora, supra), and P198 (Sibille, supra). In contrast to tumor rejection antigens—and this is a key distinction—the tum⁻ antigens are only present after the tumor cells are mutagenized. Tumor rejection antigens are present on cells of a given tumor without mutagenesis. Hence, with reference to the literature, a cell line can be tum⁺, such as the line referred to as "P1", and can be provoked to produce tum⁻ variants. Since the tum⁻ phenotype differs from that of the parent cell line, one expects a difference in the DNA of tum⁻ cell lines as compared to their tum⁺ parental lines, and this difference can be exploited to locate the gene of interest in tum⁻ cells. As a result, it was found that genes of tum⁻ variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum⁻ antigen are presented by the $L^d$ molecule for recognition by CTLs. P91A is presented by $L^d$, P35 by $D^d$ and P198 by $K^d$.

Prior patent applications PCT/US92/04354 and U.S. Pat. No. 5,342,774 which are incorporated by reference, describe inventions involving, inter alia, genes and other nucleic acid molecules which code for various TRAPs, which are in turn processed to tumor rejection antigens, or "TRAs".

The genes are useful as a source for the isolated and purified tumor rejection antigen precursor and the TRAs themselves, any of which can be used as an agent for treating the cancer for which the antigen is a "marker", as well as in various diagnostic and surveillance approaches to oncology, discussed infra. It is known, for example, that tum⁻ cells can be used to generate CTLs which lyse cells presenting different tum⁻ antigens as well as tum⁺ cells. See, e.g., Maryanski et al., Eur. J. Immunol 12: 401 (1982); and Van den Eynde et al., Modern Trends in Leukemia IX (June 1990), the disclosures of which are incorporated by reference. The tumor rejection antigen precursor may be expressed in cells transfected by the gene, and then used to generate an immune response against a tumor of interest.

In the parallel case of human neoplasms, it has been observed that autologous mixed lymphocyte-tumor cell cultures ("MLTC" hereafter) frequently generate responder lymphocytes which lyse autologous tumor cells and do not lyse natural killer targets, autologous EBV-transformed B cells, or autologous fibroblasts (see Anichini et al., Immunol. Today 8: 385–389 (1987)). This response has been particularly well studied for melanomas, and MLTC based assays have been carried out either with peripheral blood cells or with tumor infiltrating lymphocytes. Examples of the literature in this area including Knuth et al., Proc. Natl. Acad. Sci. U.S.A. 86: 2804–2802 (1984); Mukherji et al., J. Exp. Med. 158:240 (1983); Hérin et all, Int. J. Canc. 39: 390–396 (1987); Topalian et al, J. Clin. Oncol 6: 839–853 (1988). Stable cytotoxic T cell clones ("CTLs" hereafter) have been derived from MLTC responder cells, and these clones are specific for the tumor cells. See Mukherji et al., supra, Hérin et all, supra, Knuth et al., supra. The antigens recognized on tumor cells by these autologous CTLs do not appear to represent a cultural artifact, since they are found on fresh tumor cells. Topalian et al., supra; Degiovanni et al., Eur. J. Immunol. 20: 1865–1868 (1990). These observations, coupled with the techniques used herein to isolate the genes for specific murine tumor rejection antigen precursors, have led to the isolation of nucleic acid sequences coding for tumor rejection antigen precursors of TRAs presented on human tumors. It is now possible to isolate the nucleic acid sequences which code for tumor rejection antigen precursors, including, but not being limited to those most characteristic of a particular tumor, with ramifications that are described infra.

Additional work has focused upon the presentation of TRAs by the class of molecules known as human leukocyte antigens, or "HLAs". This work has resulted in several unexpected discoveries regarding the field. Specifically, in U.S. patent application Ser. No. 07/938,334, the disclosure of which is incorporated by reference, nonapeptides are taught which are presented by the HLA-A1 molecule. The reference teaches that given the known specificity of particular peptides for particular HLA molecules, one should expect a particular peptide to preferably bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 and incorporated by reference, the fact that the MAGE-1 expression product is processed to a second TRA is disclosed. This second TRA is presented by HLA-clone 10 molecules. The disclosure shows that a given TRAP can yield a plurality of TRAs.

In U.S. patent application Ser. No. 07/994,928, filed Dec. 22, 1992, and incorporated by reference herein, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

It was mentioned, supra, that different individuals possess different HLA types. It has also been found that the expression of particular MAGE genes is not always linked to particular disorders, or individuals of particular HLA types. Thus, one cannot state, e.g., that all melanoma patients will express MAGE-1 TRAP nor could one say categorically that MAGE-1 expression is limited to melanoma patients of type HLA-A1. Further, one cannot state that only one type of TRAP is expressed in individuals of a particular HLA type. No rules or guidelines can be pointed to which correlate any of these factors.

Thus, it is not expected that a second TRAP is processed to a TRA which is presented by HLA-A1 molecules. It has now been found that in addition to MAGE-1, a TRA derived from MAGE-3 TRAP is presented by HLA-A1 molecules. This is shown in examples 37–40, which follow, together with a discussion of the ramifications of this discovery.

These and various other aspects of the invention are elaborated upon in the disclosure which follows.

BRIEF DESCRIPTION OF THE FIGURES

FIG. 9 shows homology of sections of exon 3 from genes mage 1, 2 and 3.

FIG. 11 represents the data of FIG. 13 in table form.

FIG. 13 s a generalized schematic of the expression of MAGE 1, 2 and 3 genes by tumor and normal tissues.

BRIEF DESCRIPTION OF SEQUENCES

Figure 1:
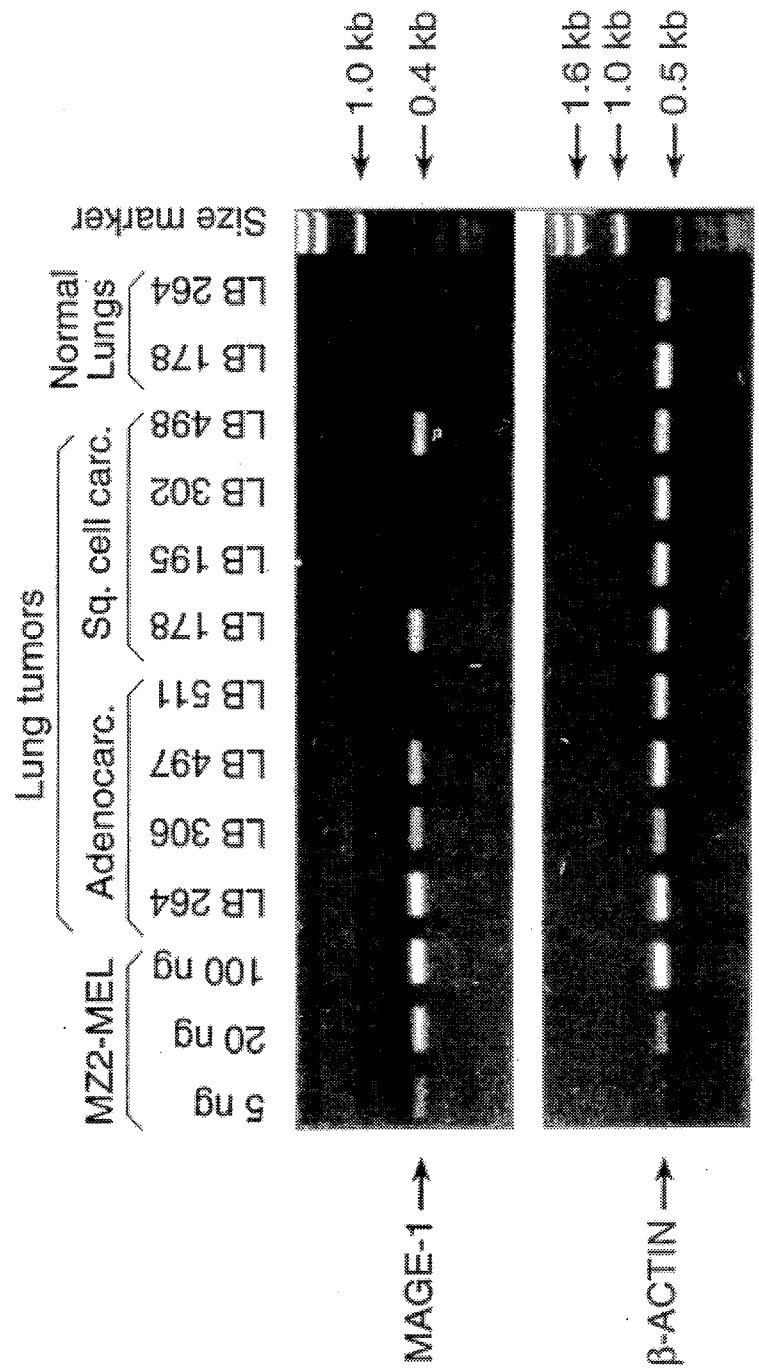
FIGS. 1A and 1B depict detection of transfectants expressing antigen P815A.

SEQ ID NO: 1 is cDNA for part of gene P1A.

SEQ ID NO: 2 presents coding region of cDNA for gene P1A.

SEQ ID NO: 3 shows non-coding DNA for P1A cDNA which is 3' to the coding region of SEQ ID NO: 2.

SEQ ID NO: 4 is the entire sequence of cDNA for P1A.

SEQ ID NO: 5 is the genomic DNA sequence for P1A.

SEQ ID NO: 6 shows the amino acid sequence for the antigenic peptides for P1A TRA. The sequence is for cells which are $A^+ B^+$, i.e., express both the A and B antigens.

SEQ ID NO: 7 is a nucleic acid sequence coding for antigen E.

SEQ ID NO: 8 is a nucleic acid sequence coding for MAGE-1.

SEQ ID NO: 9 is the gene for MAGE-2.

SEQ ID NO: 10 is the gene for MAGE 12, formerly referred to as MAGE-21. MAGE 12 is discussed by DeSmet et al., Immunogenetics 39: 121–129 (1994), incorporated by reference.

SEQ ID NO: 11 is cDNA for MAGE-3.

SEQ ID NO: 12 is the gene for MAGE-31.

SEQ ID NO: 13 is the gene for MAGE-4.

SEQ ID NO: 14 is the gene for MAGE-41.

SEQ ID NO: 15 is cDNA for MAGE-4.

SEQ ID NO: 16 is cDNA for MAGE-5.

SEQ ID NO: 17 is genomic DNA for MAGE-51.

SEQ ID NO: 18 is cDNA for MAGE-6.

SEQ ID NO: 19 is genomic DNA for MAGE-7.

SEQ ID NO: 20 is genomic DNA for MAGE-8.

SEQ ID NO: 21 is genomic DNA for MAGE-9.

SEQ ID NO: 22 is genomic DNA for MAGE-10.

SEQ ID NO: 23 is genomic DNA for MAGE-11.

SEQ ID NO: 24 is genomic DNA for smage-I.

SEQ ID NO: 25 is genomic DNA for smage-II.

SEQ ID NO: 26 is peptide MZ2-E.

SEQ ID NOS: 27–46 are primers used in the invention.

DETAILED DESCRIPTION OF PREFERRED EMBODIMENTS

Many different "MAGE" genes have been identified, as will be seen from the sequences which follow the application. The protocols described in the following examples were used to isolate these genes and cDNA sequences.

"MAGE" as used herein refers to a nucleic acid sequence isolated from human cells. The acronym "smage" is used to describe sequences of murine origin.

When "TRAP" or "TRAs" are discussed herein as being specific to a tumor type, this means that the molecule under consideration is associated with that type of tumor, although not necessarily to the exclusion of other tumor types.

EXAMPLE 1

In order to identify and isolate the gene coding for antigen P815A, gene transfection was used. This approach requires both a source of the gene, and a recipient cell line. Highly transfectable cell line P1.HTR was the starting material for the recipient, but it could not be used without further treatment, as it presents "antigen A", one of four recognized P815 tumor antigens. See Van Pel et al., Molecular Genetics 11: 467–475 (1985). Thus, screening experiments were carried out to isolate cell lines which did not express the antigen and which nonetheless possessed P1.HTR's desirable qualities.

To do this, P1.HTR was screened with CTLs which were specific for each of tumor antigens A, B, C and D. Such CTLs are described by Uyttenhove et al., J. Exp. Med. 157: 1040–1052 (1983).

To carry out the selection, $10^6$ cells of P1. HTR were mixed with $2-4\times10^6$ cells of the CTL clone in a round bottom tube in 2 ml of medium, and centrifuged for three minutes at 150×g. After four hours at 37° C., the cells were washed and resuspended in 10 ml of medium, following Maryanski et al., Eur. J. Immunol. 12: 406–412 (1982). Additional information on the CTL assay and screening protocol, in general may be found in Boon et al., J. Exp. Med. 152: 1184–1193 (1980), and Maryanski et al., Eur. J. Immunol. 12: 406–412 (1982), the disclosures of which are incorporated by reference.

When these selections were carried out, a cell line variant was found which expressed neither antigen A or B. Additional selections with CTLs specific for antigen C then yielded a variant which also lacked antigen C. Please see FIG. 2 for a summary of the results of these screenings. The variant PO.HTR is negative for antigens A, B and C, and was therefore chosen for the transfection experiments.

The cell line PO.HTR has been deposited in accordance with the Budapest Treaty at the Institute Pasteur Collection Nationale De Cultures De Microorganismes, 28, Rue de Docteur Roux, 75724 Paris France, and has accession number I-1117.

This methodology is adaptable to secure other cell lines which are variants of a cell type which normally presents at least one of the four recognized P815 tumor antigens, i.e., antigens A, B, C and D, where the variants present none of antigens A, B and C. P1.HTR is a mastocytoma cell line, so it will be seen that the protocol enables the isolation of biologically pure mastocytoma cell lines which express none of P815 antigens A, B and C, but which are highly transfectable. Other tumor types may also be screened in this fashion to secure desired, biologically pure cell lines. The resulting cell lines should be at least as transfectable with foreign DNA as is P1.HTR, and should be selected so as to not express a specific antigen.

EXAMPLE 2

Previous work reported by DePlaen et al., Proc. Natl. Acad. Sci. U.S.A. 85: 2274–2278 (1988) the disclosure of which is incorporated by reference herein had shown the efficacy of using cosmid library transfection to recover genes coding for tum⁻ antigens.

Selective plasmid and genomic DNA of P1.HTR were prepared, following Wölfel et al., Immunogenetics 26: 178–187 (1987). The transfection procedure followed Corsaro et al., Somatic Cell Molec. Genet 7: 603–616 (1981), with some modifications. Briefly, 60 µg of cellular DNA and 3 µg of DNA of plasmid pHMR272, described by Bernard et al., Exp. Cell. Biol. 158: 237–243 (1985) were mixed. This plasmid confers hygromycin resistance upon recipient cells, and therefore provides a convenient way to screen for transfectants. The mixed DNA was combined with 940 ul of 1 mM Tris-HCl (pH 7.5), 0.1 mM EDTA, and 310 ul 1M $CaCl_2$. The solution was added slowly, and under constant agitation, to 1.25 ml of 50 mM Hepes, 280 mM NaCl, 1.5 mM $Na_2HPO_4$, adjusted to pH 7.1 with NaOH. Calcium phosphate—DNA precipitates were allowed to form for 30–45 minutes at room temperature. Following this, fifteen groups of PO.HTR cells ($5\times10^6$) per group were centrifuged for 10 minutes at 400 g. Supernatants were removed, and pellets were resuspended directly into the medium containing the DNA precipitates. This mixture was incubated for 20 minutes at 37° C., after which it was added to an 80 cm² tissue culture flask containing 22.5 ml DMEM, supplemented with 10% fetal calf serum. After 24 hours, medium was replaced. Forty-eight hours after transfection, cells were collected and counted. Transfected cells were selected in mass culture using culture medium supplemented with hygromycin B (350 ug/ml). This treatment selected cells for hygromycin resistance.

For each group, two flasks were prepared, each containing $8\times10^6$ cells in 40 ml of medium. In order to estimate the number of transfectants, $1\times10^6$ cells from each group were plated in 5 ml DMEM with 10% fetal calf serum (FCS), 0.4% bactoagar, and 300 ug/ml hygromycin B. The colonies were then counted 12 days later. Two independent determinations were carried out and the average taken. This was multiplied by 5 to estimate the number of transfectants in the corresponding group. Correction had to be made for the cloning efficiency of P815 cells, known to be about 0.3.

EXAMPLE 3

Eight days after transfection as described in example 2, supra, antibiotic resistant transfectants were separated from dead cells, using density centrifugation with Ficoll-Paque. These cells were maintained in non-selective medium for 1 or 2 days. The cells were plated in 96 well microplates (round bottom), at 30 cells/microwell in 200 ul of culture medium. Anywhere from 100–400 microwells were prepared, depending on the number of transfectants prepared. Agar colony tests gave estimates of 500–3000. After 5 days, the wells contained about $6\times10^4$ cells and replicate plates were prepared by transferring 1/10 of the wells to microplates which were then incubated at 30° C. One day later, master plates were centrifuged, medium removed, and 750 CTLs against P815 antigen A (CTL-P1:5) were added to each well together with $10^6$ irradiated syngeneic feeder spleen cells in CTL culture medium containing 40 U/ml recombinant human IL-2, and HAT medium to kill stimulator cells. Six days later, plates were examined visually to identify wells where CTLs had proliferated. Where plates showed proliferating microcultures, aliquots of 100 ul of the wells were transferred to another plate containing $^{51}Cr$ labeled P1.HTR target cells ($2\times10^3$–$4\times10^3$ per well), and chromium release was measured after 4 hours. Replicate microcultures corresponding to those showing high CTL activity were expanded and cloned by limited dilution in DMEM with 10% FCS. Five days later, about 200 clones were collected and screened with the CTL-P1:5 cell line, described supra, in a visual lysisassay. See FIG. 1A for these results.

In these experiments, three of the fifteen groups of transfectants yielded a few positive microcultures. These microcultures were tested for lytic activity against P1.HTR, as described supra. Most of the microcultures where proliferation was observed showed lytic activity. This activity was well above background, as shown in FIG. 1B. This figure summarizes data wherein two groups of cells (groups "5" and "14"), 400 and 300 microwells were seeded with 30 hygromycin resistant transfected cells. Amplification and duplication of the microcultures was followed by addition of anti-A CTL P1:5. Six days later, lytic activity against P1.HTR was tested. In the figure, each point represents lytic activity of a single microculture.

Duplicate microcultures corresponding to several positive wells were subcloned, and more than 1% of the subclones were found to be lysed by anti-A CTL. Thus, three independent transfectants expressing P815A were obtained from 33,000 hygromycin resistant transfectants. One of these lines, referred to hereafter as P1A.T2 was tested further.

Figure 2:
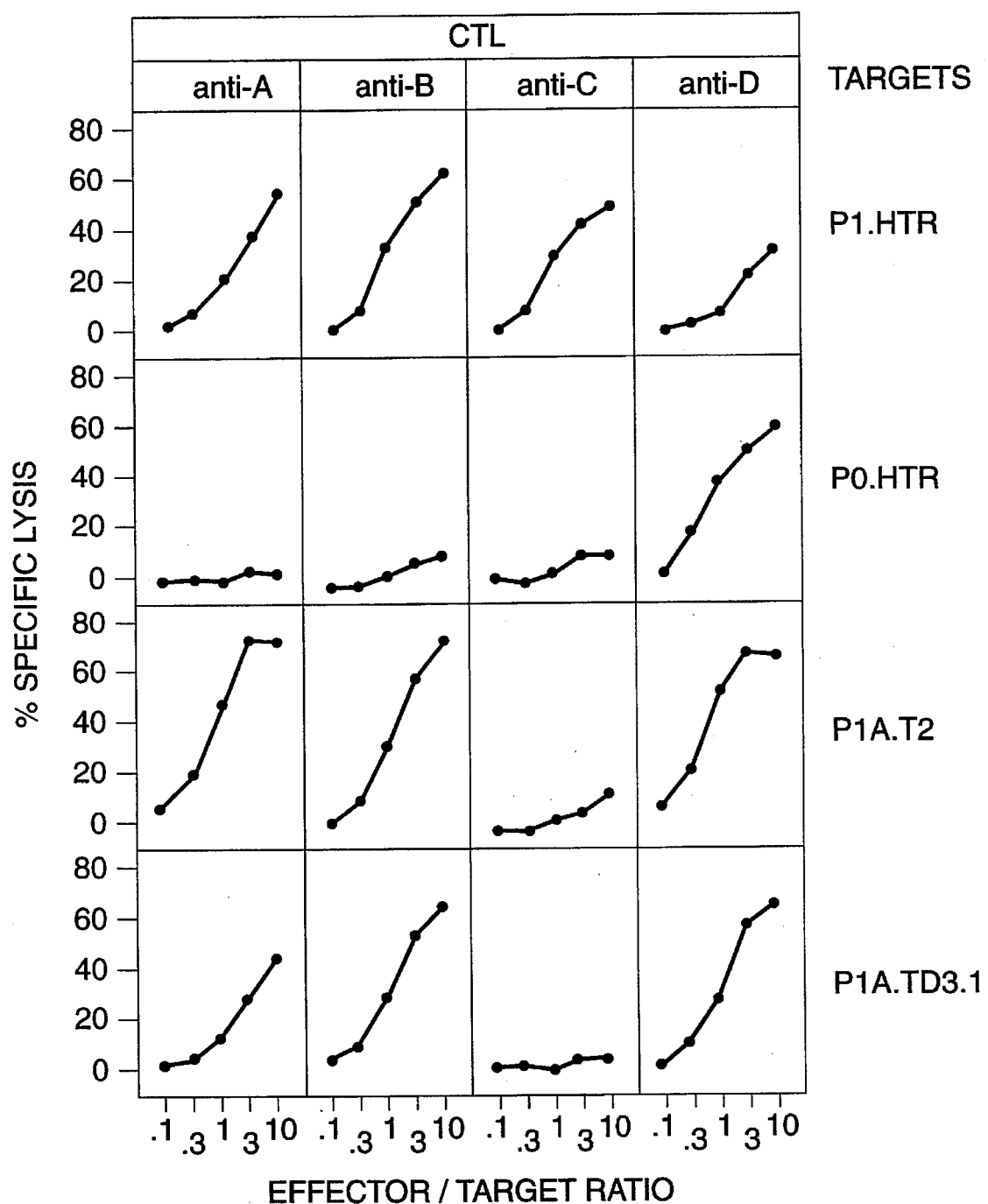
FIG. 2 shows the sensitivity of clones P1.HTR, PO.HTR, genomic transfectant P1A.T2 and cosmid transfectant P1A.TC3.1 to lysis by various CTLs, as determined by chromium release assays.

The relevant antigen profile of P1A.T2 is shown in FIG. 2, this being obtained via anti-CTL assays of the type described supra.

EXAMPLE 4

The CTL assays carried out for P1A.T2 demonstrated that it presented antigen A ("P815A"), and therefore had received the gene from P1.HTR. To that end, this cell line was used as a source for the gene for the antigen precursor in the following experiments.

Prior work had shown that genes coding for tum⁻ antigens could be recovered directly from transfectants obtained with a cosmid library. See DePlaen et al., Proc. Natl. Acad. Sci. U.S.A. 85: 2274–2278 (1988). This procedure was followed for recovery of the P815 gene.

Total genomic DNA of P1A.T2 was partially digested with restriction endonuclease Sau 3A1, and fractionated by NaCl density gradient ultracentrifugation to enrich for 35–50 kb DNA fragments, following Grosveld et al., Gene 10: 6715–6732 (1982). These fragments were ligated to cosmid arms of C2RB, described by Bates et al., Gene 26: 137–146 (1983), the disclosure of which is incorporated by reference. These cosmid arms had been obtained by cleavage with SmaI and treatment with calf intestinal phosphatase, followed by digestion with BamHI. Ligated DNA was packaged into lambda phage components, and titrated on *E. coli* ED 8767, following Grosveld et al., supra. Approximately $9\times10^5$ ampicillin resistant colonies were obtained per microgram of DNA insert.

The cosmid groups were amplified by mixing 30,000 independent cosmids with 2 ml of ED 8767 in 10 mM $MgCl_2$, incubated 20 minutes at 37° C., diluted with 20 ml of Luria Bertani ("LB") medium, followed by incubation for one hour. This suspension was titrated and used to inoculate 1 liter of LB medium in the presence of ampicillin (50 ug/ml). At a bacterial concentration of $2\times10^8$ cells/ml ($OD_{600}$=0.8), a 10 ml aliquot was frozen, and 200 ug/ml chloramphenicol was added to the culture for overnight incubation. Total cosmid DNA was isolated by alkaline lysis procedure, and purified on CsCl gradient.

In these experiments, a library of 650,000 cosmids was prepared. The amplification protocol involved the use of 21 groups of approximately 30,000 cosmids.

EXAMPLE 5

Using the twenty-one groups of cosmids alluded to supra, (60 ug) and 4 ug of pHMR272, described supra, groups of $5\times10^6$ PO.HTR cells were used as transfectant hosts. Transfection was carried out in the same manner as described in the preceding experiments. An average of 3000 transfectants per group were tested for antigen presentation, again using CTL assays as described. One group of cosmids repeatedly yielded positive transfectants, at a frequency of about 1/5,000 drug resistant transfectants. The transfectants, as with P1A.T2, also showed expression of both antigen A and B. The pattern of expression of transfectant P1A.TC3.1 is shown in FIG. 2.

EXAMPLE 6

As indicated in Example 5, supra, three independent cosmid transfected cells presenting P815A antigen were isolated. The DNA of these transfectants was isolated and packaged directly with lambda phage extracts, following DePlaen et al., Proc. Natl. Acad. Sci. U.S.A. 85: 2274–2278 (1988). The resulting product was titrated on E. coli ED 8767 with ampicillin selection, as in Example 5. Similarly, amplification of the cosmids and transfection followed Example 5, again using PO.HTR.

High frequencies of transfection were observed, as described in Table 1, which follows:

TABLE 1

| Transfer of the expression of antigen P815A by cosmids obtained by direct packaging | | |
|---|---|---|
| Transfectant obtained with the cosmid library | No. of cosmids obtained by direct packaging of 0.5 µg of DNA | No. of transfectants expressing P815A/no. of HmB$^r$ transfectants |
| TC3.1 | 32 | 87/192 |
| TC3.2 | 32000 | 49/384 |
| TC3.3 | 44 | 25/72 |

The cosmids were analyzed with restriction enzymes and it was found that directly packaged transfectant P1A.TC3.1 contained 32 cosmids, 7 of which were different. Each of these 7 cosmids was transfected into PO.HTR, in the manner described supra, and again, following the protocols described above, transfectants were studied for presentation of P815A. Four of the cosmid transfectants showed P815A presentation and, as with all experiments described herein, P815B was co-expressed.

Of the four cosmids showing presentation of the two antigens, cosmid C1A.3.1 was only 16.7 kilobases long, and was selected for further analysis as described infra.

Figure 3:
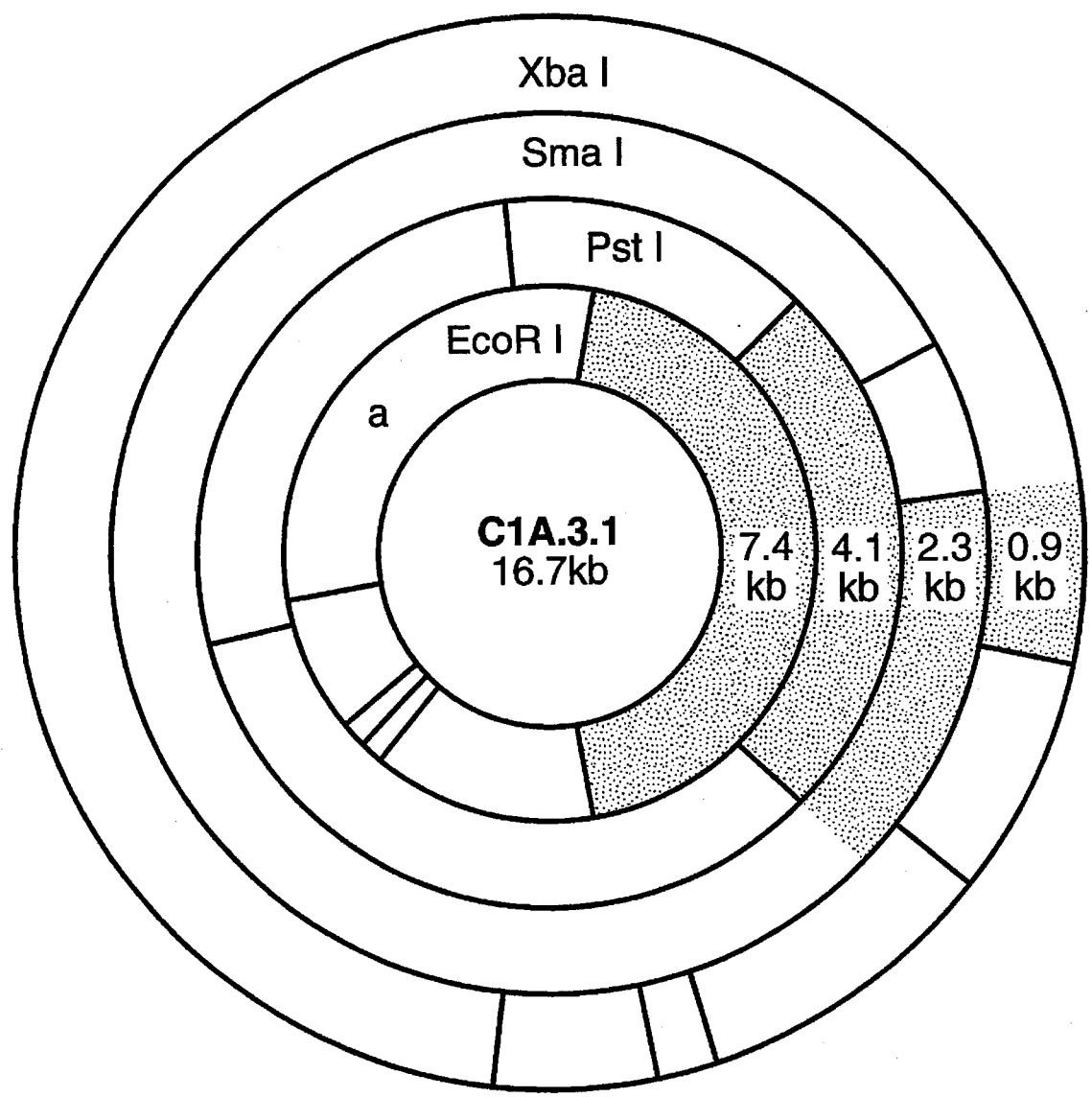
FIG. 3 is a restriction map of cosmid C1A.3.1.

The cosmid C1A.3.1 was subjected to restriction endonuclease analysis, yielding the map shown in FIG. 3.

All EcoRI fragments were transfected, again using the above described protocols, and only the 7.4 kilobase fragment produced a transfectant that anti-A CTLs could lyse. Similar experiments were carried out on the PstI fragments, and only a 4.1 kb fragment fully contained within the 7.4 kb EcoRI fragment produced lysable transfectants.

This fragment (i.e., the 4.1 kb PstI fragment), was digested with SmaI, giving a 2.3 kb fragment which also yielded host cells presenting antigens A and B after transfection. Finally, a fragment 900 bases long, secured with SmaI/XbaI, also transferred expression of the precursors of these two antigens, i.e., the transfected host cell presented both antigen A and antigen B.

EXAMPLE 7

The 900 base fragment described above was used as a probe to detect the expression of the P815A gene in parent cell line P1.HTR. To accomplish this, total cellular RNA was first isolated using the guanidine-isothiocyanate procedure of Davis et al., Basic Methods In Molecular Biology (Elseview Science Publishing Co, New York) (1986). The same reference was the source of the method used to isolate and purify polyA$^+$ mRNA using oligodT cellulose column chromatography.

Samples were then subjected to Northern Blot analysis. RNA samples were fractionated on 1% agarose gels containing 0.66M formaldehyde. The gels were treated with 10×SSC (SSC: 0.15M NaCl; 0.015M sodium citrate, pH 7.0) for 30 minutes before overnight blotting on nitrocellulose membranes. These were baked for two hours at 80° C., after which the membranes were prehybridized for 15 minutes at 60° C. in a solution containing 10% dextran sulfate, 1% SDS and 1M NaCl. Hybridization was then carried out using denatured probe (the 900 base fragment), together with 100 ug/ml salmon sperm DNA.

Figure 4:
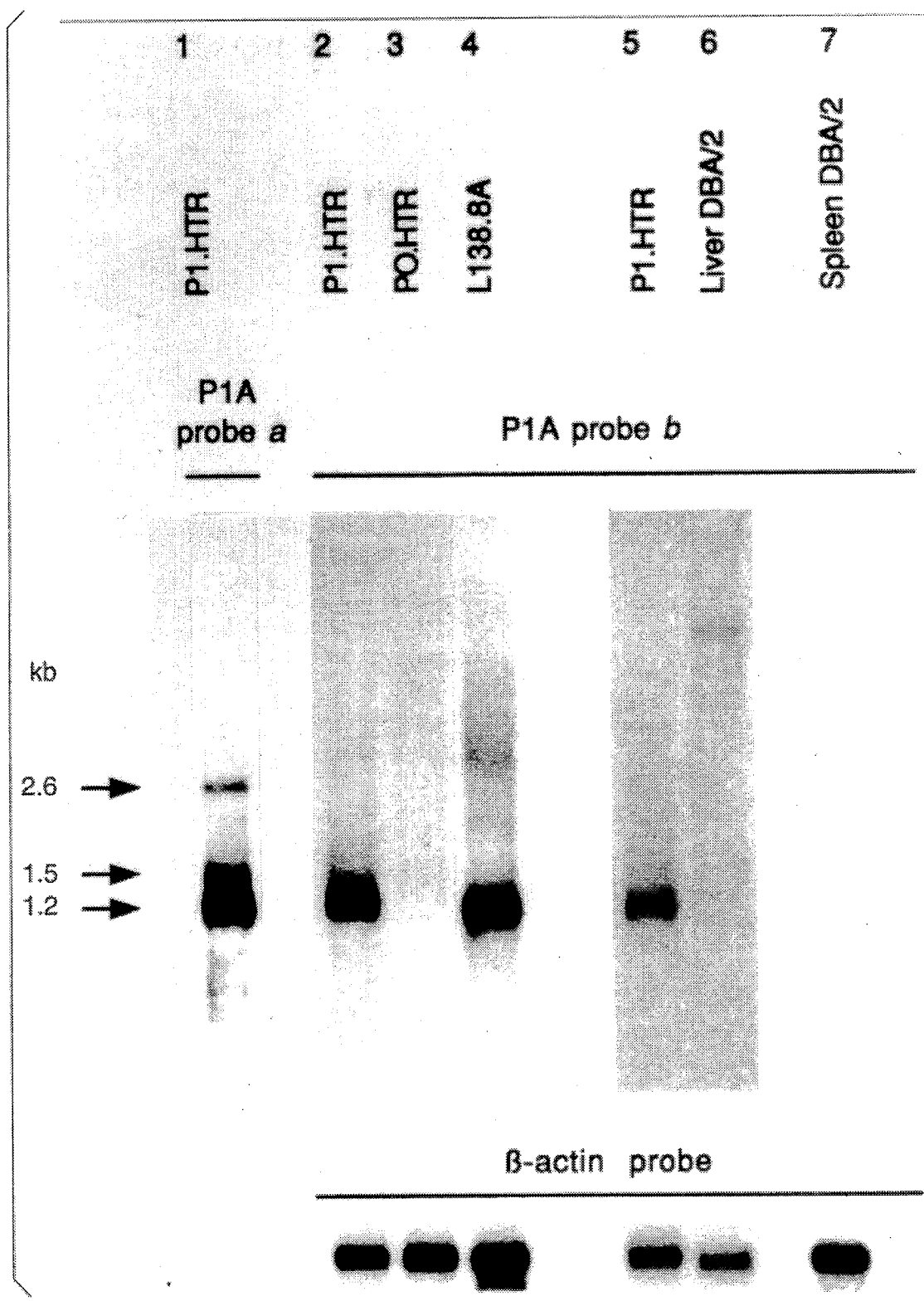
FIG. 4 shows Northern Blot analysis of expression of gene P1A.

When this protocol was carried out using P1.HTR poly A$^+$ RNA, a band of 1.2 kb and two fainter bands were identified, as shown in FIG. 4, lane 1 (6 ug of the RNA).

The same probe was used to screen a cDNA library, prepared from poly-A$^+$ RNA from the cell line. This yielded a clone with a 1 kb insert, suggesting a missing 5' end. The Northern blots for the cDNA are not shown.

Hybridization experiments in each case were carried out overnight at 60° C. The blots were washed twice at room temperature with 2×SSC and twice at 60° C. with 2×SSC supplemented with 1% SDS.

The foregoing experiments delineated the DNA expressing the P815A antigen precursor sufficiently to allow sequencing, using the well known Sanger dideoxy chain termination method. This was carried out on clones generated using a variety of restriction endonucleases and by specific priming with synthetic oligonucleotide primers. The results for exons of the gene are set forth in SEQUENCE ID NO: 4.

EXAMPLE 8

The Northern analysis described supra suggested that the 5' end of the cDNA was missing. To obtain this sequence, cDNA was prepared from P1.HTR RNA using a primer corresponding to positions 320–303. The sequence was then amplified using the polymerase chain reaction using a 3' primer corresponding to positions 286–266 and a 5' primer described by Frohman et al., Proc. Natl. Acad. Sci. U.S.A. 85: 8998–9002 (1988). A band of the expected size (270 bases) was found, which hybridized to the 900 bp SmaI/XbaI fragment described Supra on a Southern blot. Following cloning into m13tg 130 and mtg 131, the small, 270 bp fragment was sequenced. The sequence is shown in SEQUENCE ID NO: 1.

EXAMPLE 9

Following the procurement of the sequences described in Examples 7 and 8 and depicted in SEQ ID NO: 4, a 5.7 kb region of cosmid C1A.3.1 was sequenced. This fragment was known to contain the 900 base fragment which expressed P815A in transfectants. This experiment permitted delineation of introns and exons, since the cosmid is genomic in origin.

Figure 5:
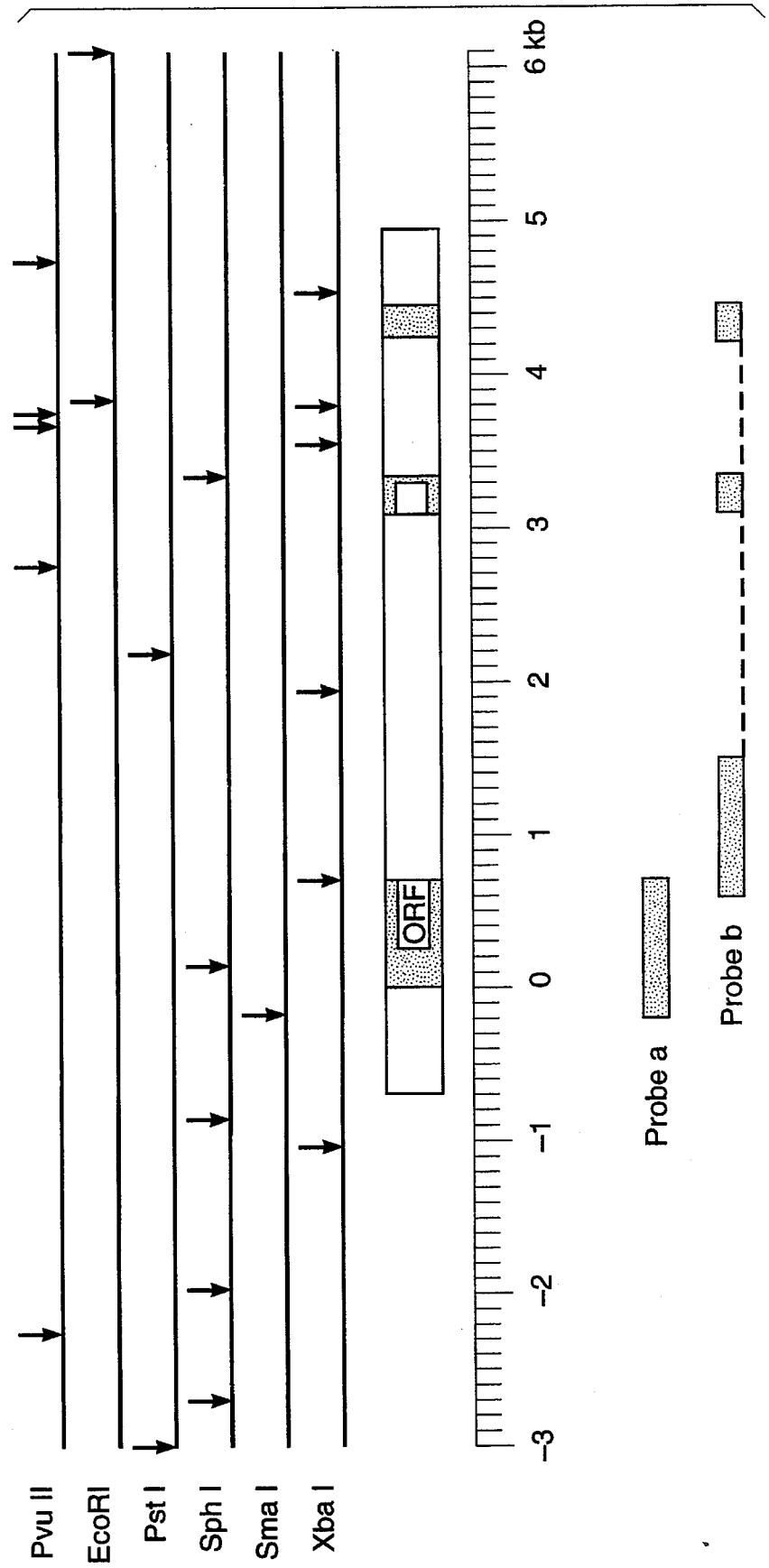
FIG. 5 sets forth the structure of gene P1A with its restriction sites.

The delineated structure of the gene is shown in FIG. 5. Together with SEQ ID NO: 4, these data show that the gene for the antigen precursor, referred to as "P1A" hereafter, is approximately 5 kilobases long and contains 3 exons. An ORF for a protein of 224 amino acids starts in exon 1, ending in exon 2. The 900 base pair fragment which transfers expression of precursors for antigens A and B only contains exon 1. The promoter region contains a CAAT box, as indicated in SEQ ID NO: 1, and an enhancer sequence. This latter feature has been observed in promoters of most MHC class I genes, as observed by Geraghty et al., J. Exp. Med 171: 1–18 (1990); Kimura et al., Cell 44: 261–272 (1986).

A computer homology search was carried out, using program FASTA with K-triple parameters of 3 and 6, as suggested by Lipman et al., Science 227: 1435–1441 (1985), and using Genbank database release 65 (October 1990). No homology was found except for a stretch of 95 bases corresponding to part of an acid region coded by exon 1 (positions 524–618), which is similar to sequences coding for acidic regions in mouse nucleolar protein NO38/B23, as described by Bourbon et al., Mol. Biol. 200: 627–638 (1988), and Schmidt-Zachmann et al., Chromosoma 96: 417–426 (1988). Fifty six of 95 bases were identical. In order to test whether these homologies were the reason for cross hybridizing, experiments were carried out using a mouse spleen cDNA library screened with the 900 base fragment. cDNA clones corresponding closely to the sizes of the cross hybridizing bands were obtained. These were partially sequenced, and the 2.6 kb cDNA was found to correspond exactly to reported cDNA sequence of mouse nucleolin, while the 1.5 kb cDNA corresponded to mouse nucleolar protein NO38/B23.

Analysis of the nucleotide sequence of the gene, referred to as "P1A" hereafter, suggests that its coded product has a molecular mass of 25 kd. Analysis of the SEQ ID NO: 4 shows a potential nuclear targeting signal at residues 5–9 (Dingwall et al., Ann. Rev. Cell Biol. 2: 367–390 (1986)), as well as a large acidic domain at positions 83–118. As indicated supra, this contains the region of homology between P1A and the two nucleolar proteins. A putative phosphorylation site can be found at position 125 (serine). Also, a second acidic domain is found close to the C-terminus as an uninterrupted stretch of 14 glutamate residues. A similar C-terminal structure has been found by Kessel et al. Proc. Natl. Acad. Sci. U.S.A. 84: 5306–5310 (1987), in a murine homeodomain protein having nuclear localization.

In studies comparing the sequence of gene P1A to the sequences for P91A, P35B and P198, no similarities were found, showing that P1A is indicative of a different class of genes and antigens.

EXAMPLE 10

With the P1A probe and sequence in hand, investigations were carried out to determine whether the gene present in normal tissue was identical to that expressed by the tumor. To do this, phage libraries were prepared, using lambda zapII 10 and genomic DNA of DBA2 murine kidney cells. P1A was used as a probe. Hybridization conditions were as described supra, and a hybridizing clone was found. The clone contained exons one and two of the P1A gene, and corresponded to positions –0.7 to 3.8 of FIG. 5. Following localization of this sequence, PCR amplification was carried out to obtain the sequence corresponding to 3.8 to 4.5 of FIG. 5.

Sequence analysis was carried out, and no differences were found between the gene from normal kidneys and the P1A gene as obtained from the P815 tumor cells.

Figure 6:
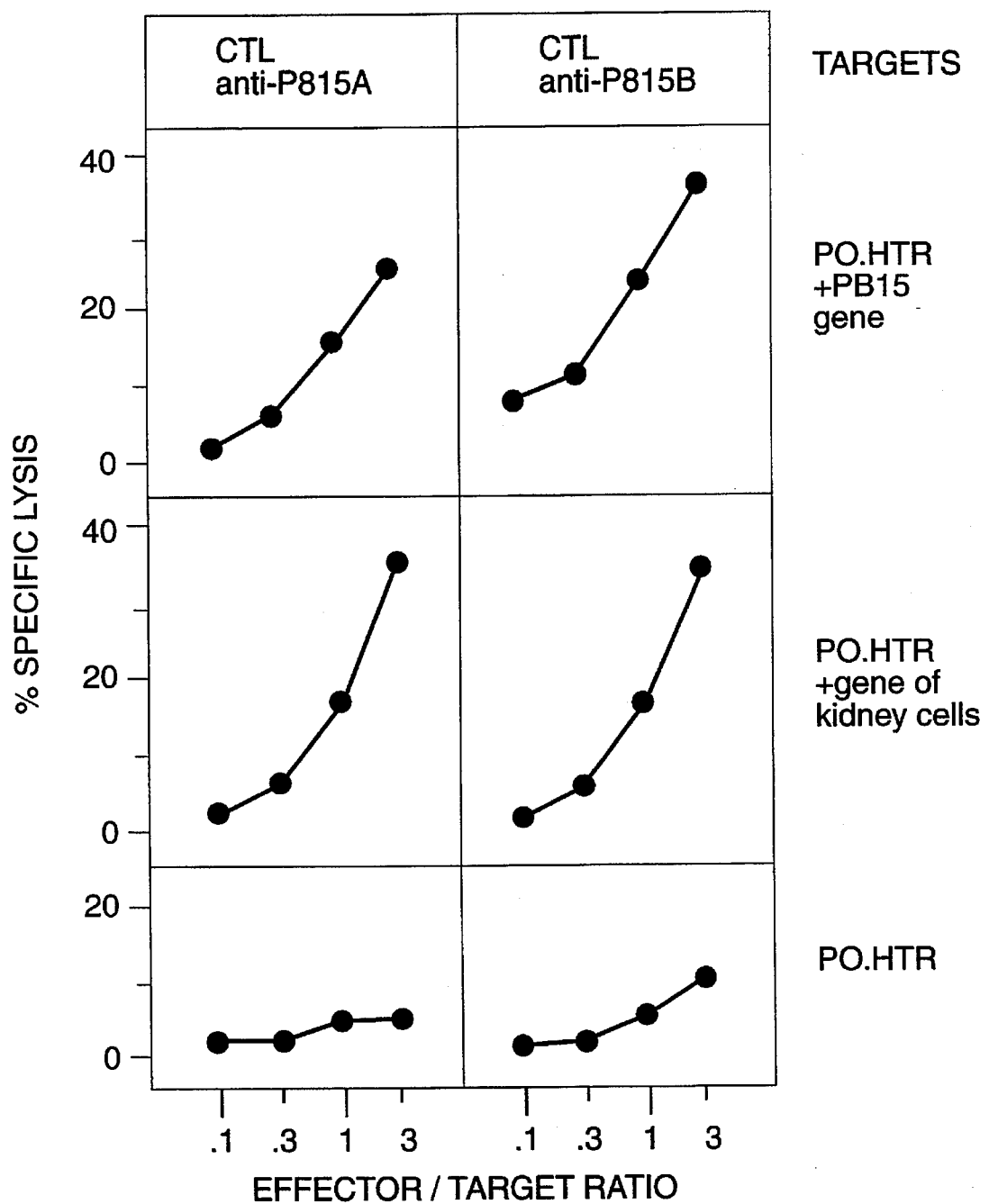
FIG. 6 shows the results obtained when cells were transfected with the gene from P1A, either isolated from P815 or normal cells and then tested with CTL lysis.

In further experiments, the gene as found in DBA/2 kidney cells was transfected into PO.HTR, as described supra. These experiments, presented pictorially in FIG. 6, showed that antigens A and B were expressed as efficiently by the kidney gene isolated from P815 cells as with the P1A gene isolated from normal kidney cells.

These experiments lead to the conclusion that the gene coding for the tumor rejection antigen precursor is a gene that does not result from a mutation; rather, it would appear that the gene is the same as one present in normal cells, but is not expressed therein. The ramifications of this finding are important, and are discussed infra. In studies not elaborated upon herein, it was found that variants of the gene were available. Some cells were "P1A$^-$B$^+$", rather than the normal "P1A". The only difference between these is a point mutation in exon 1, with the 18th triplet coding for Ala in the variant instead of Val.

EXAMPLE 11

Additional experiments were carried out with other cell types. Following the protocols described for Northern blot hybridizations supra, RNA of normal liver and spleen cells was tested to determine if a transcript of the P1A gene could be found. The Northern blot data are presented in FIG. 4 and, as can be seen, there is no evidence of expression.

The murine P815 cell line from which P1A was isolated is a mastocytoma. Therefore, mast cell lines were studied to determine if they expressed the gene. Mast cell line MC/9, described by Nabel et al., Cell 23: 19–28 (1981), and short term cultures of bone marrow derived mast cells were tested in the manner described supra (Northern blotting), but no transcript was found. In contrast when a BALB/C derived IL-3 dependent cell line L138.88A (Hültner et al., J. Immunol. 142: 3440–3446 (1989)) was tested, a strong signal was found. The mast cell work is shown in FIG. 4.

Figure 7:
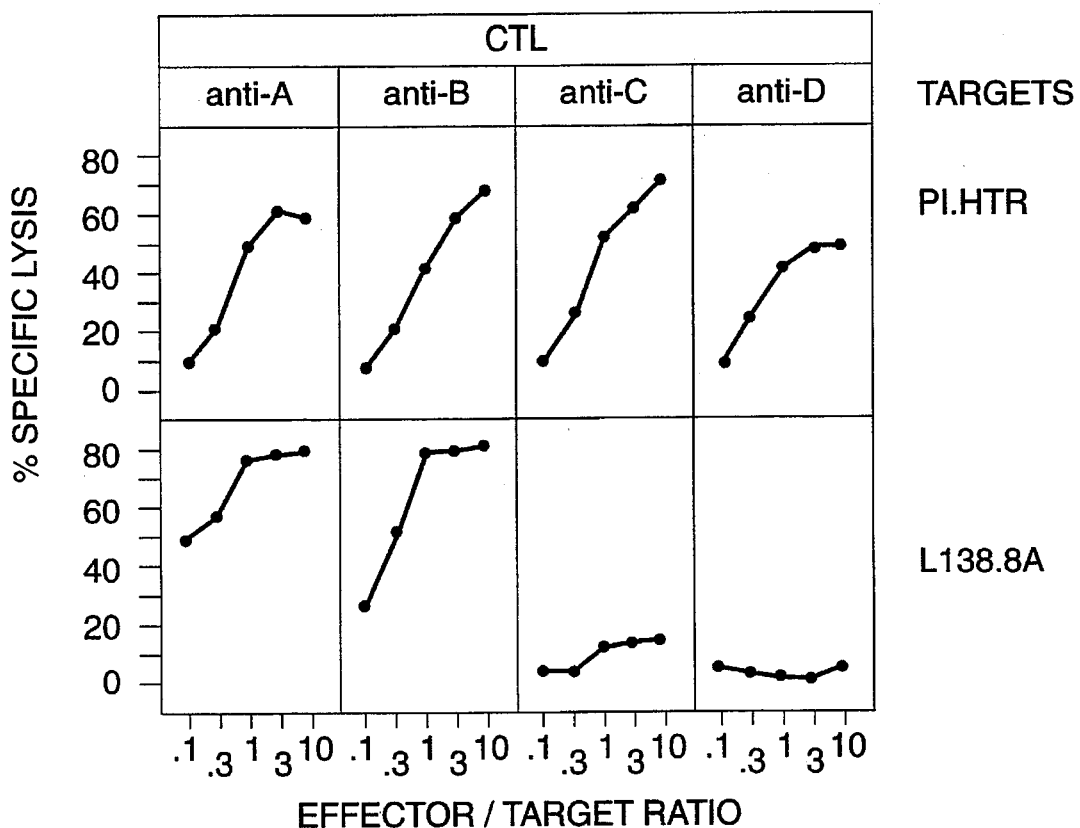
FIG. 7 shows lytic studies using mast cell line L138. 8A.

It is known that both BALB/C and DBA/2 mice share H-$2^d$ haplotype, and thus it was possible to test sensitivity to lysis using the CTLs described supra. FIG. 7 shows these results, which essentially prove that anti-A and anti-B CTLs lysed the cells strongly, whereas anti-C and anti-D lines did not.

Further tests were carried out on other murine tumor cell lines, i.e., teratocarcinoma cell line PCC4 (Boon et al., Proc. Natl. Acad. Sci. U.S.A. 74: 272–275 (1977), and leukemias LEC and WEHI-3B. Expression could not be detected in any of these samples.

EXAMPLE 12

The actual presentation of the P1A antigen by MHC molecules was of interest. To test this, cosmid C1A.3.1 was transfected into fibroblast cell line DAP, which shows phenotype H-$2^k$. The cell lines were transfected with genes expressing one of the K$^d$, D$^d$, and L$^d$ antigen. Following transfection with both the cosmid and the MHC gene, lysis with CTLs was studied, again as described supra. These studies, summarized in Table 2, show that L$^d$ is required for presentation of the P1A antigens A and B.

TABLE 2

H-2-restriction of antigens P815A and P815B

| Recipient cell* | No. of clones lysed by the CTL/no. of HmB$^r$ clones* | |
|---|---|---|
| | CTL anti-A | CTL anti-B |
| DAP (H-2$^k$) | 0/208 | 0/194 |
| DAP + K$^d$ | 0/165 | 0/162 |
| DAP + D$^d$ | 0/157 | 0/129 |
| DAP + L$^d$ | 25/33 | 15/20 |

*Cosmid C1A.3.1 containing the entire P1A gene was transfected in DAP cells previously transfected with H-2$^d$ class I genes as indicated.
*Independent drug-resistant colonies were tested by lysis by anti-A or anti-B CTL in a visual assay.

The observation that one may associate presentation of a tumor rejection antigen with a particular MHC molecule was confirmed in experiments with human cells and HLA molecules, as elaborated upon infra.

EXAMPLE 13

Using the sequence of the P1A gene as well as the amino acid sequence derivable therefrom, antigenic peptides which were A$^+$ B$^+$ (i.e., characteristic of cells which express both the A and B antigens), and those which are A$^-$B$^+$ were identified. The peptide is presented in SEQ ID NO: 26. This peptide, when administered to samples of PO.HTR cells in the presence of CTL cell lines specific to cells presenting it, led to lysis of the PO.HTR cells, lending support to the view that peptides based on the product expressed by the gone can be used as vaccines.

EXAMPLE 14

The human melanoma cell line referred to hereafter as MZ2-MEL is not a clonal cell line. It expresses four stable antigens recognized by autologous CTLs, known as antigens "D, E, F, and A". In addition, two other antigens "B" and "C" are expressed by some sublines of the tumor. CTL clones specific for these six antigens are described by Van den Eynde et al., Int. J. Canc. 44: 634–640 (1989). Among the recognized subclones of MZ2-MEL are MEL.43, MEL3.0 and MEL3.1. (Van den Eynde et al., supra). Cell line MEL3.1 expresses antigen E, as determined by CTL studies as described for P815 variants, supra, so it was chosen as a source for the nucleic acid sequence expressing the antigen precursor.

In isolating the pertinent nucleic acid sequence for a tumor rejection antigen precursor, the techniques developed supra, showed that a recipient cell is needed which fulfills two criteria: (i) the recipient cell must not express the TRAP of interest under normal conditions, and (ii) it must express the relevant class I HLA molecule. Also, the recipient cell must have a high transfection frequency, i.e., it must be a "good" recipient.

In order to secure such a cell line, the clonal subline ME3-1 was subjected to repeated selection with anti-E CTL 82/30 as described by Van den Eynde, supra. The repeated cycles of selection led to isolation of subclone MZ2-MEL-2.2 isc E$^-$. This subclone is also HPRT$^-$, (i.e., sensitive to HAT medium: 10$^{-4}$M hypoxanthine, 3.8×10$^{-7}$ aminopterine, 1.6×10$^{-5}$M 2-deoxythymidine). The subclone is referred to as "MEL-2.2" for simplicity hereafter.

EXAMPLE 15

The genomic DNA of MEL3.0 was prepared following W ölfel et al., Immunogenetics 26: 178–187 (1987), the disclosure of which is incorporated by reference. The plasmid pSVtkneoβ, as described by Nicolas et al., Cold Spring Harb., Conf. Cell Prolif. 10: 469–485 (1983) confers geneticin resistance, so it can be used as a marker for cotransfection, as it was in this experiment.

Following a procedure similar but not identical to that of Corsaro et al., Somatic Cell Molec. Genet 7: 603–616 (1981), total genomic DNA and the plasmid were cotransfected. The genomic DNA (60 μg) and plasmid DNA (6 μg) were mixed in 940 μl of 1 mM Tris.HCl (pH 7.5), 0.1 mM EDTA, after which 310 μl of 1M CaCl$_2$ was added. This solution was slowly added, under constant agitation, to 1.25 ml of 2×HBS (50 mM HEPES, 280 mM NaCl 1.5 mM Na$_2$HPO$_4$, adjusted to pH 7.1 with NaOH). The calcium phosphate DNA precipitates were allowed to form for 30–45 minutes at room temperature, after which they were applied to 80 cm$^2$ tissue culture flasks which had been seeded 24 hours previously with 3×10$^6$ MEL2.2 cells, in 22.5 ml of melanoma culture medium (Dulbecco's Modified Eagle's Medium) supplemented with 10% fetal calf serum. After 24 hours, the medium was replaced. Forty eight hours after transfection, the cells were harvested and seeded at 4×10$^6$ cells per 80 cm$^2$ flask in melanoma culture medium supplemented with 2 mg/ml of geneticin. The geneticin serves as a selection marker.

EXAMPLE 16

Thirteen days after transfection, geneticin-resistant colonies were counted, harvested, and cultured in nonselective medium for 2 or 3 days. Transfected cells were then plated in 96-well microplates at 200 cells/well in 200 ul of culture medium with 20% fetal calf serum (FCS) in order to obtain approximately 30 growing colonies per well. The number of microcultures was aimed at achieving redundancy, i.e., such that every independent transfectant should be represented at least four times.

After 10 days, wells contained approximately 6×10$^4$ cells. These cells were detached, and ⅓ of each microculture was transferred to a duplicate plate. After 6 hours, i.e., after readherence, medium was removed and 1500 anti-E CTL (CTL 82/30), were added to each well in 100 μl of CTL culture medium with 35 U/ml of IL-2. One day later, the supernatant (50 μl) was harvested and examined for TNF concentration, for reasons set forth in the following example.

EXAMPLE 17

The size of the mammalian genome is 6×10$^6$ kb. As the average amount of DNA integrated in each drug-resistant transfectant was expected to be about 200 kb, a minimum of 30,000 transfectants would need to be examined to ascertain whether antigen E had been transfected. Prior work with murine cells had shown that when a CTL stimulation assay was used, groups containing only 3% of cells expressing the antigen of interested could be identified. This should reduce the number of assays by a factor of 30. While an anti-E CTL assay, as described supra, in mixed E$^+$/E$^-$ cells was helpful, it was not sufficient in that consistent results could not be obtained.

As a result, an alternative test was devised. Stimulation of CTLs was studied by release of tumor necrosis factor ("TNF") using well known methodologies which need not be repeated here. As described in Example 15, 1500 CTL 82/30 cells had been added per well of transfectants. These CTLs were collected 6 days after stimulation. As indicated supra, after ⅓ of the cells in each well had been removed and the remaining ⅔ (4×10$^4$) had readhered, the CTLs and IL-2 were added thereto. The 50 μl of supernatant was removed 24 hours later and transferred to a microplate containing $3\times10^4$ W13 (WEHI-164 clone 13; Espevik et al., J. Immunol. Meth. 95: 99–105 (1986)) cells in 50 µl of W13 culture medium (RPMI-1640, supplemented with L-arginine (116 mg/l), L-asparagine (36 mg/l), L-glutamine (216 mg/l), and 10% FCS supplemented with 2 µg of actinomycin D at 37% in an 8% $CO_2$ atmosphere. The cell line W13 is a mouse fibrosarcoma cell line sensitive to TNF. Dilutions of recombinant TNF-β in RPMI 1640 were added to target cell controls.

The W13 cultures were evaluated after 20 hours of incubation, and dead cell percentage was measured using an adaptation of the colorimetric assay of Hansen et al., J. Immunol. Meth. 119: 203–210 (1989). This involved adding 50 ml of (3-(4,5-dimethylthiazol-2-yl)-2,5-diphenyl tetrazolium bromide at 2.5 mg/ml in PBS, followed by two hours of incubation at 37° C. Dark blue formazan crystals were dissolved by adding 100 µl of lysis solution (1 volume N,N dimethyl formamide mixed at 37° C. with two volumes of water containing 30% (w/v) sodium dodecyl sulphate, at pH 4.7 from 1.6% acetic acid and 2.5% 1N HCl). Plates were incubated at 37° C. overnight, and ODs were taken at 570 nm using 650 nm as control. Dead cell percentage was determined via the formula:

$$100\times \left[ 1 - \frac{100 - (OD_{570}\ \text{sample well})}{OD_{570}\ \text{well} + \text{medium}} \right]$$

following Espevik et al., J. Immunol. Meth. 95: 99–105 (1986). The results showed that even when the ratio of $E^+/E^-$ cells was as low as 1/45, significant production of TNF was observed, thus showing active CTLs. This led to the decision to test the drug resistant transfectants in groups of 30.

EXAMPLE 18

Cells were tested for TNF production as discussed in Example 17, supra. A total of 100 groups of $E^-$ cells ($4\times10^6$ cells/group) were tested following transfection, and $7\times10^4$ independent geneticin resistant transfectants were obtained, for an average of 700 per group. Only one group of transfected cells led to a microculture which caused anti-E antigen CTL clone 82/30 to produce TNF. Of 300 clones tested, 8 were positive. These clones were then tested for lysis by anti-E CTL, using the standard $^{51}$Cr release assay, and were found to be lysed as efficiently as the original $E^+$ cell line. The transfectant E.T1, discussed herein, had the same lysis pattern as did MEL2.2 for CTLs against antigens B,C,D and F.

The fact that only one transfectant presented the antigen out of 70,000 geneticin resistance transfectants may at first seem very low, but it is not. The work described supra for P815 showed an average frequency of 1/13,000. Human DNA recipient MEL2.2 appears to integrate 5 times less DNA than P1.HTR.

EXAMPLE 19

Once transfectant E.T1 was found, analysis had to address several questions including whether an $E^+$ contaminant of the cell population was the cause. The analysis of antigen presentation, described supra, shows that E.T1 is $B^-$ and $C^-$, just like the recipient cell MEL2.2. It was also found to be $HPRT^-$, using standard selection procedures. All $E^+$ cells used in the work described herein, however, were $HPRT^+$.

It was also possible that an $E^+$ revertant of MEL2.2 was the source for E.T1. To test this, the observation by Perucho et al., Cell 22: 309–317 (1980), that cotransfected sequences usually integrate together at a single location of recipient genome was employed. If antigen E in a transfectant results from cotransfection with pSVtkneoβ, then sequences should be linked and deletion of the antigen might also delete the neighboring pSVtkneoβ sequences. Wölfel et al., supra, has shown this to be true. If a normally $E^-$ cell is transfected with pSVtkneoβ, then sequences should be linked and deletion of the antigen might also delete the neighboring pSVtkneoβ sequences. If a normally $E^+$ cell transfected with pSVtkneoβ is E.T1, however, "co-deletion" should not take place. To test this, the transfectant E.T1 was subjected to immunoselection with 82/30, as described supra. Two antigen loss variants were obtained, which resisted lysis by this CTL. Neither of these had lost geneticin resistance; however, Southern blot analysis showed loss of several $neo^r$ sequences in the variants, showing close linkage between the E gene and $neo^r$ gene in E.T1, leading to the conclusion that E.T1 was a transfectant.

EXAMPLE 20

The $E^+$ subclone MZ2-MEL 43 was used as a source of DNA for preparation of a cosmid library. This library of nearly 700,000 cosmids was transfected into MZ2-MEL 2.2 cells, following the cosmid transfection protocols described supra.

By packaging the DNA of cosmid transfectants directly into lambda phage components, it is sometimes possible to retrieve cosmids that contain the sequences of interest. This procedure was unsuccessful here, so we rescued the transfected sequence by ligating DNA of the transfectant to appropriate restriction fragments of cosmid vector pTL6. This was tried with two transfectants and was successful with one of them. One cosmid, referred to as B3, was recovered from this experiment, and subjected to restriction endonuclease digestion via XmaI, or by BamHI digestion of a large, 12 kb XmaI transfected fragment. The fragments were cloned into vector pTZ 18R, and then transfected into MEL2.2. Again, TNF production was the measure by which successful transfection was determined. The experiments led to the determination of a gene sequence capable of transfecting antigen E on the 12 kb XmaI fragment, and then on the 2.4 kb fragment of BamHI digestion of the 12 kb segment.

Figure 12:
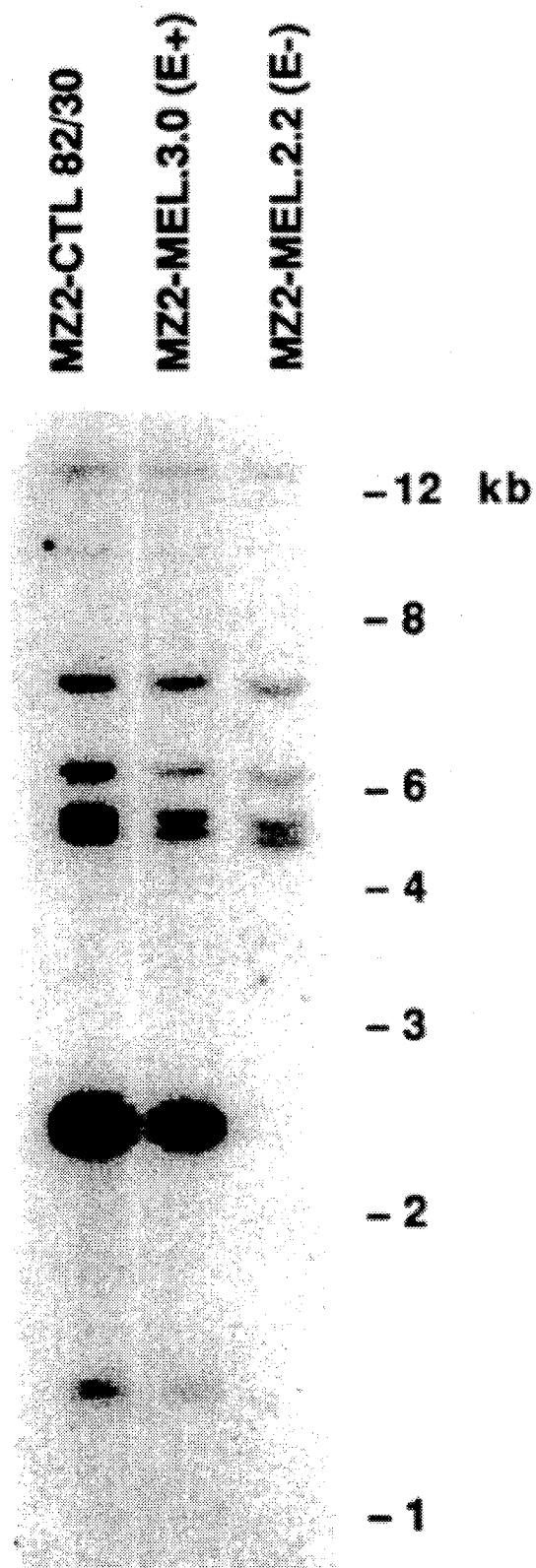
FIG. 12 shows Southern Blot experiments using the various human melanoma cell lines employed in this application.
Figure 14B:
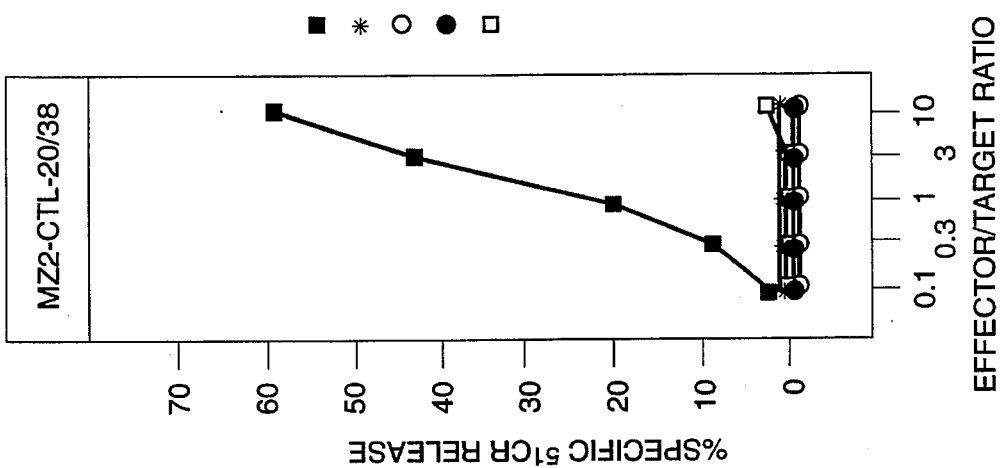
FIG. 14 shows results from a chromium release assay using CTL clone 20/38 on various cell lines.
Figure 14A:
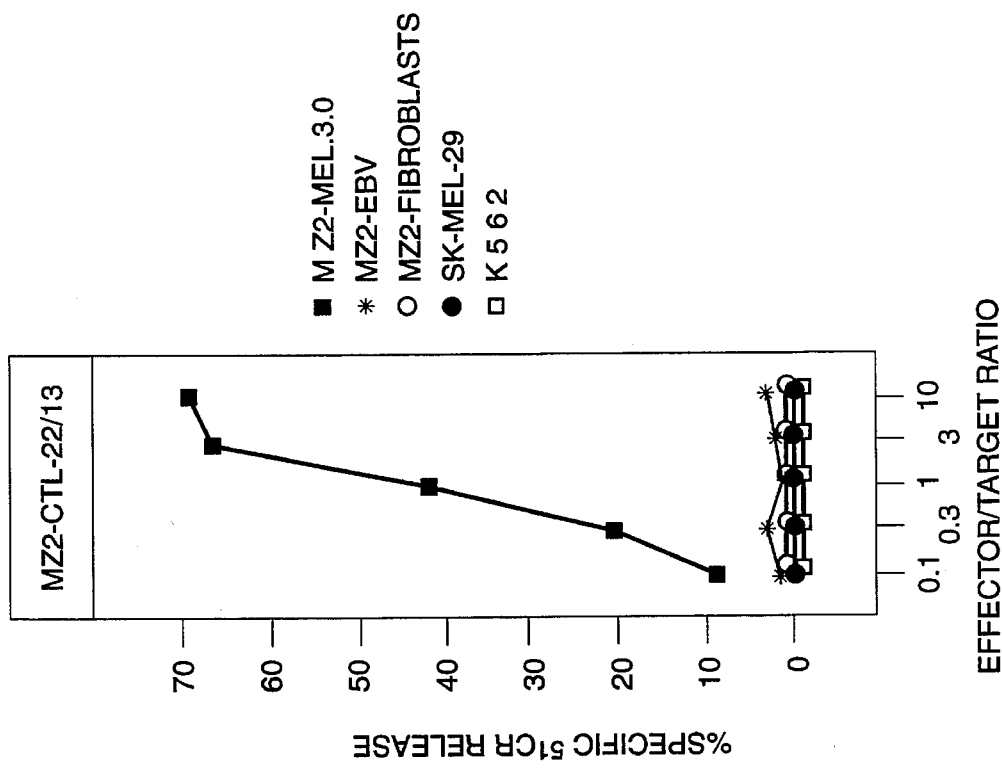
Figure 15A:
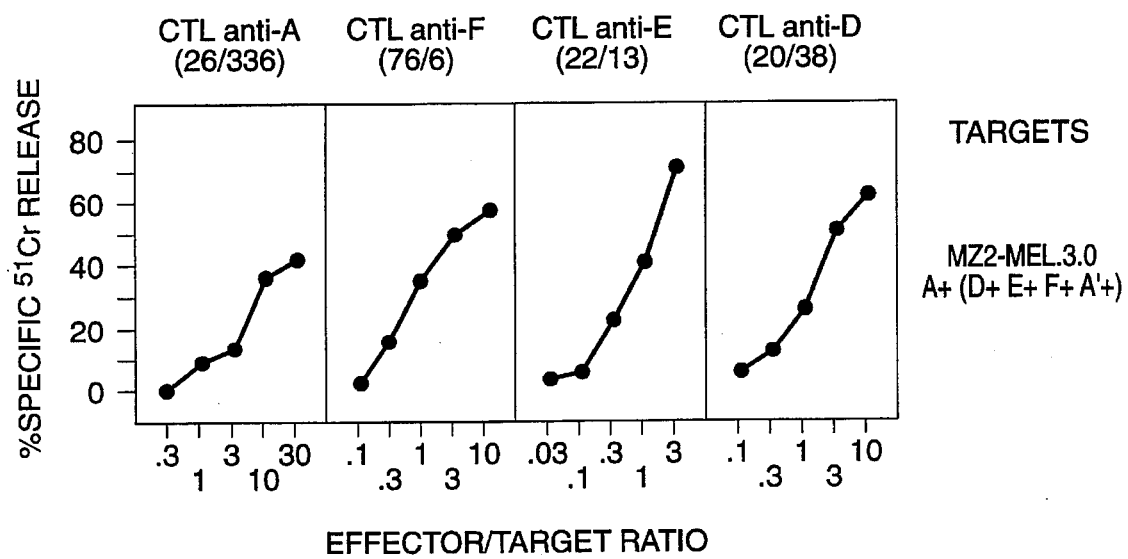
FIG. 15 presents the result of assays undertaken to determine antigenic specificity of CTL clone 20/38.
Figure 15B:
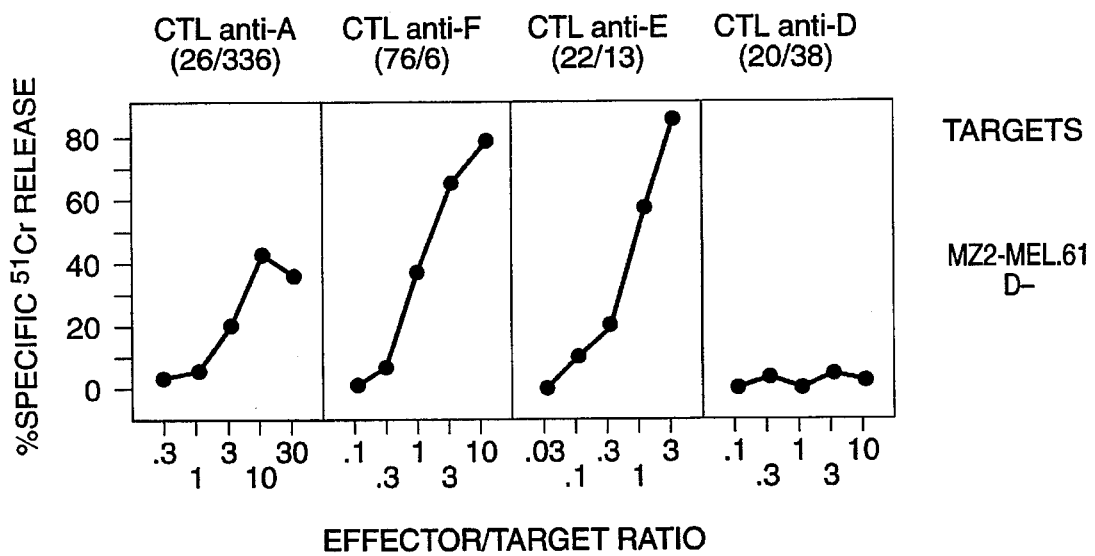
Figure 15C:
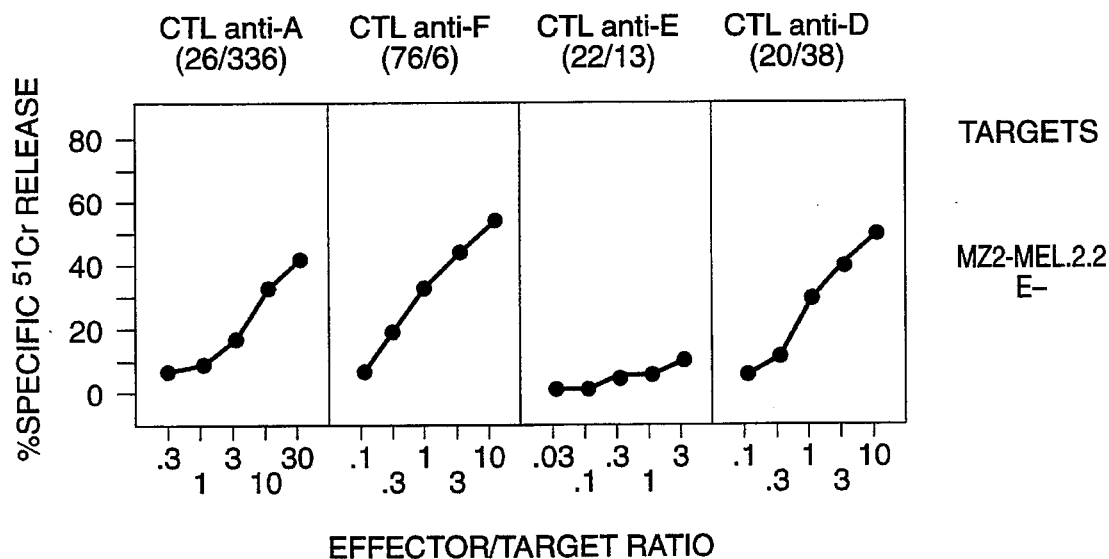
Figure 15D:
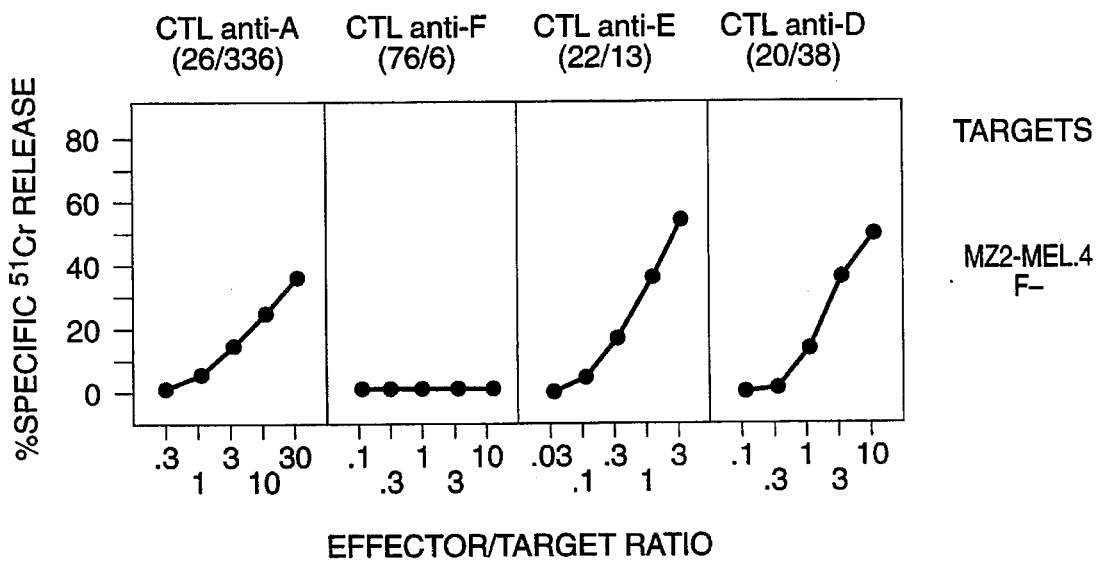

The 2.4 kb fragment hybridizes with a 2.4 kb fragment from MZ2-MEL and with a T cell clone of patient MZ-2, as determined by Southern Blots (BamHI digested DNA). The band is absent from $E^-$ antigen loss variants of MZ2-MEL, as seen in FIG. 12.

The sequence for the E antigen precursor gene has been determined, and is presented herein:

| | 10 | 20 | 30 | 40 | 50 | 60 | |
|---|---|---|---|---|---|---|---|
| 1 | GGATCCAGGC | CCTGCCAGGA | AAAATATAAG | GGCCCTGCGT | GAGAACAGAG | GGGGTCATCC | 60 |
| 61 | ACTGCATGAG | AGTGGGGATG | TCACAGAGTC | CAGCCCACCC | TCCTGGGTAGC | ACTGAGAAGC | 120 |
| 121 | CAGGGCTGTG | CTTGCGGTCT | GCACCCTGAG | GGCCCGTGGA | TTCCTCTTCC | TGGAGCTCCA | 180 |
| 181 | GGAACCAGGC | AGTGAGGCCT | TGGTCTGAGA | CAGTATCCTC | AGGTCACAGA | GCAGAGGATG | 240 |
| 241 | CACAGGGTGT | GCCAGCAGTG | AATGTTTGCC | CTGAATGCAC | ACCAAGGGCC | CCACCTGCCA | 300 |
| 301 | CAGGACACAT | AGGACTCCAC | AGAGTCTGGC | CTCACCTCCC | TACTGTCAGT | CCTGTAGAAT | 360 |
| 361 | CGACCTCTGC | TGGCCGGCTG | TACCCTGAGT | ACCCTCTCAC | TTCCTCCTTC | AGGTTTTCAG | 420 |
| 421 | GGGACAGGCC | AACCCAGAGG | ACAGGATTCC | CTGGAGGCCA | CAGAGGAGCA | CCAAGGAGAA | 480 |
| 481 | GATCGTAAG | TAGGCCTTTG | TTAGAGTCTC | CAAGGTTCAG | TTCTCAGCTG | AGGCCTCTCA | 540 |
| 541 | CACACTCCCT | CTCTCCCCAG | GCCTCTGGGT | CTTCATTGCC | CAGCTCCTGC | CCACACTCCT | 600 |
| 601 | GCCTGCTGCC | CTGACGAGAG | TCATCATGTC | TCTTGAGCAG | AGGAGTCTGC | ACTGCAAGCC | 660 |
| 661 | TGAGGAAGCC | CTTGAGGCCC | AACAAGAGGC | CCTGGGCTGG | TGTGTGTGCA | GGCTGCCACC | 720 |
| 721 | TCCTCTCCT | CCTCTCTGGT | CCTGGGCACC | GGGAGGAGG | TGCCCACTGC | TGGTCAACA | 780 |
| 781 | GATCCTCCCA | AGAGTCCTCA | GGGAGCCTCC | GCCTTTCCCA | CTACCATCAA | CTTCACTCGA | 840 |
| 841 | CAGAGGCAAC | CCAGTGAGGG | TTCCAGCAGC | CGTGAAGAG | AGGGGCCAAAG | CACCTCTTGT | 900 |
| 901 | ATCCTGGAGT | CCTTGTTCCG | AGCAGTAATC | ACTAAGAAGG | TGGCTGATTT | GGTTGGTTTT | 960 |
| 961 | CTGCTCCTCA | AATATCGAGC | CAGGGAGCCA | GTCACAAAGG | CAGAAATGCT | GGAGAGTGTC | 1020 |
| 1021 | ATCAAAAATT | ACAAGCACTG | TTTTCCTGAG | ATCTTCGGCA | AAGCCTCTGA | GTCCTTGCAG | 1080 |
| 1081 | CTGGTCTTTG | GCAATGACGT | GAAGGAAGCA | GACCCCACCG | GCCACTCCTA | TGTCCTTGTC | 1140 |
| 1141 | ACCTGCCTAG | GTCTCTCCTA | TGATGGCCTG | CTGGGTGATA | ATCAGATCAT | GCCCAAGACA | 1200 |
| 1201 | GGCTTCCTGA | TAATTGTCCT | GGTCATGATT | GCAATGGAGG | GCGGCCATGC | TCCTGAGGAG | 1260 |
| 1261 | GAAATCTGGG | AGGAGCTGAG | TGTGATGGAA | GTGTATGATG | GGAGGGAGCA | CAGTGCCTAT | 1320 |
| 1321 | GGGGAGCCCA | GGAAGCTGCT | CACCCAAGAT | TTGGTGCAGG | AAAAGTACCT | GGAGTACGGC | 1380 |
| 1381 | AGGTGCCGGA | CAGTGATCCC | GCACGCTATG | AGTTCCTGTG | GGTCCAAGG | GCCCTCGCTG | 1440 |
| 1441 | AAACCAGCTA | TGTGAAAGTC | CTTGAGTATG | TGATCAAGGT | CAGTGCAAGA | GTTCGCTTTT | 1500 |
| 1501 | TCTTCCCATC | CCTGCGTGAA | GCAGCTTTGA | GAGGAGGAA | AGAGGGAGTC | TGAGCATGAG | 1560 |
| 1561 | TTGCAGCCAA | GGCCAGTGGG | AGGGGGACTG | GGCCAGTGCA | CCTTCCAGGG | CCGCGTCCAG | 1620 |
| 1621 | CAGTTCCCCC | TGCCTCGTGT | GACATGAGGC | CCATTCTTCA | CTCTGAAGAG | AGCGGTCAGT | 1680 |
| 1681 | GTTCTCAGTA | GTAGGTTTCT | GTTCTATTGG | GTGACTTGAA | GATTTATCTT | TGTTCTCTTT | 1740 |
| 1741 | TGGAATTGTT | CAAATGTTTT | TTTTAAGGG | ATGGTTAAT | GAACTTCAGC | ATCCAAGTTT | 1800 |
| 1801 | ATGAATGACA | GCAGTCACAC | AGTTCTGTGT | ATATAGTTTA | AGGGTAAGAG | TCTTGTGTTT | 1860 |
| 1861 | TATTCAGATT | GGGAAATCCA | TTCTATTTTG | TGAATTGGGA | TAATAACAGC | AGTGAATAA | 1920 |
| 1921 | GTACTTAGAA | ATGTGAAAAA | TGAGCAGTAA | AATAGATGAG | ATAAAGAACT | AAAGAAATTA | 1980 |
| 1981 | AGAGTAGTC | AATTCCTTGCC | TTATACCTCA | GTCTATTCTG | TAAATAAATC | AAAGATATAT | 2040 |
| 2041 | GCATACCTGG | ATTTCCTTGG | CTTTCCTTGAG | AATGTAAGAG | AGCATCTGCT | TGAATAAAGA | 2100 |
| 2101 | ATTCTTCCTG | TTCACTGGCT | CTTTTCTCT | CCATGCACTG | ATACCCACCC | TTTTGGAAGG | 2160 |
| 2161 | CCCTGGGTTA | GTAGTGGAGA | TGCTAAGGTA | AGCCAGACTC | GGTGCCAAGA | ATAGGGTCGT | 2220 |
| 2221 | AGAGTCTAGG | AGCTGCAGTC | ACGTAATCGA | GGTGGACAAGA | TGTCCTCTAA | AGATTGTAGGG | 2280 |
| 2281 | AAAAGTGAGA | GAGGGGTGAG | GGTGTGGGGC | TCCGGGTGAG | AGTGGTGGAG | TGTCAATGCC | 2340 |
| 2341 | CTGAGCTGGG | GCATTTTGGG | CTTTGGGAAA | CTGGCAGTTC | TTCTGGGGGA | TGTGATTGTA | 2400 |
| 2401 | ATGATCTTGG | GTGGATCC | | | | GCTGATTGTA | 2418 |

EXAMPLE 21

Figure 8:
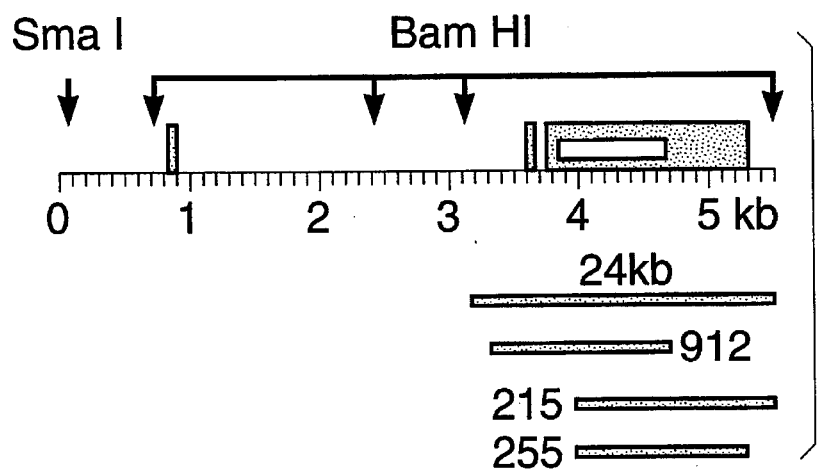
FIG. 8 is a map of subfragments of the 2.4 kb antigen E fragment which also express the antigen.

After the 2.4 kb genomic segment had been identified, studies were carried out to determine if an "E⁺" subline expressed any homologous DNA. Cell line MZ2-MEL 3.0 was used as a source, and a cDNA library was prepared from its mRNA, using art known techniques. The 2.4 kb segment was used as a probe, and mRNA of about 1.8 kb was identified as homologous, using Northern blot analysis. When cDNA was screened, clones were obtained showing almost complete identity to parts of the 2.4 kb fragment. Two exons were thus identified. An additional exon was located upstream of these, via sequencing segments of cosmid B3 located in front of the 2.4 kb BamHI fragment. The gene extends over about 4.5 kb, as shown in FIG. 8. The starting point of the transcribed region was confirmed using PCR for the 5' end of the cDNA. The three exons comprise 65, 73, and 1551 base pairs. An ATG is located at position 66 of exon 3, followed by a 927 base pair reading frame.

EXAMPLE 22

To determine if smaller segments of the 2.4 kb fragment could transfer the expression of antigen E, smaller pieces corresponding to the larger gene were prepared, using art recognized techniques, and transferred into E⁻ cells. FIG. 8 shows the boundaries of the three segments.

Transfer of antigen expression in this manner indicates that the gene codes for the antigen precursor, rather than coding for a protein which activates the antigen.

EXAMPLE 23

The probing of cDNA described supra revealed, surprisingly, two different but closely related cDNAs. These cDNAs, when tested, did not transfer expression of antigen E, but they do show substantial homology to the first cDNA segment. The three segments, appear to indicate a newly recognized family of genes, referred to as "MAGE" for "melanoma antigen". In FIG. 9, "mage-1" directs expression of the antigen from MZ2 cells. Portions of the third exon of each gene are presented in FIG. 9. The second and third sequences are more closely related to each other than the first (18.1 and 18.9% difference compared to the first; 12% with each other). Out of 9 cDNA clones obtained, three of each type were obtained, suggesting equal expression. "MAGE" as used hereafter refers to a family of molecules, and the nucleic acids coding for them. These nucleic acids share a certain degree of homology and are expressed in tumor cells including several types of human tumor cells as well as in human tumors. The family is referred to as "MAGE" because the first members were identified in human melanoma cells. As the experiments which follow indicate, however, the members of the MAGE family are not at all restricted to melanoma tumors; rather, MAGE refers to a family of tumor rejection antigen precursors and the nucleic acid sequences coding therefore. The antigens resulting therefrom are referred to herein as "MAGE TRAs" or "melanoma antigen tumor rejection antigens"

EXAMPLE 24

Experiments with mouse tumors have demonstrated that new antigens recognized by T cells can result from point mutations that modify active genes in a region that codes for the new antigenic peptide. New antigens can also arise from the activation of genes that are not expressed in most normal cells. To clarify this issue for antigen MZ2-E, the mage-1 gene present in the melanoma cells was compared to that present in normal cells of patient MZ2. Amplification by polymerase chain reaction (PCR) of DNA of phytohemagglutinin-activated blood lymphocytes using primers surrounding a 1300 bp stretch covering the first half of the 2.4 kb fragment was carried out. As expected, a PCR product was obtained whereas none was obtained with the DNA of the E⁻ variant. The sequence of this PCR product proved identical to the corresponding sequence of the gene carried by the E⁺ melanoma cells. Moreover, it was found that antigen MZ2-E was expressed by cells transfected with the cloned PCR product. This result suggests that the activation of a gene normally silent is responsible for the appearance of tumor rejection antigen MZ2-E.

EXAMPLE 25

Figure 10:
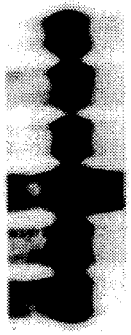
FIG. 10 shows the result of Northern blots for MAGE genes on various tissues.

In order to evaluate the expression of gens mage-1 by various normal and tumor cells, Northern blots were hybridized with a probe covering most of the third exon. In contrast with the result observed with human tumor cell line MZ2-MEL 3.0, no band was observed with RNA isolated from a CTL clone of patient MZ2 and phytohemagglutinin-activated blood lymphocytes of the same patient. Also negative were several normal tissues of other individuals (FIG. 10 and FIG. 11). Fourteen melanoma cell lines of other patients were tested. Eleven were positive with bands of varying intensities. In addition to these culture cell lines, four samples of melanoma tumor tissue were analyzed. Two samples, including a metastasis of patient MZ2 proved positive, excluding the possibility that expression of the gens represented a tissue culture artefact. A few tumors of other histological types, including lung tumors were tested. Most of these tumors were positive (FIGS. 10 and 11). These results indicated that the MAGE gens family is expressed by many melanomas and also by other tumors. However, they provided no clear indication as to which of genes mage-1, 2 or 3 were expressed by these cells, because the DNA probes corresponding to the three genes cross-hybridized to a considerable extent. To render this analysis more specific, PCR amplification and hybridization with highly specific oligonucleotide probes were used. cDNAs were obtained and amplified by PCR using oligonucleotide primers corresponding to sequences of exon 3 that were identical for the three MAGE genes discussed herein. The PCR products were then tested for their ability to hybridize to three other oligonucleotides that showed complete specificity for one of the three genes (FIG. 9). Control experiments carried out by diluting RNA of melanoma MZ2-MEL 3.0 in RNA from negative cells indicated that under the conditions used herein the intensity of the signal decreased proportionally to the dilution and that positive signals could still be detected at a dilution of $1/300$. The normal cells (lymphocytes) that were tested by PCR were confirmed to be negative for the expression of the three MAGE genes, suggesting therefore a level of expression of less than $1/300^{th}$ that of the MZ2 melanoma cell line (FIG. 11). For the panel of melanoma cell lines, the results clearly showed that some melanomas expressed MAGE genes mage 1, 2 and 3 whereas other expressed only mage-2 and 3 (FIGS. 11 and 10). Some of the other tumors also expressed all three genes whereas others expressed only mage-2 and 3 or only mage-3. It is impossible to exclude formally that some positive PCR results do not reflect the expression of one of the three characterized MAGE genes but that of yet another closely related gene that would share the sequence of the priming and hybridizing oligonucleotides. It can be concluded that the MAGE gene family is expressed by a large array of different tumors and that these genes are silent in the normal cells tested to this point.

EXAMPLE 26

The availability of a sequence that transfects at high efficiency and efficiently expresses a TRAP made it possible to search for the associated major histocompatibility complex (MHC) class I molecule. The class I specificities of patient MZ2 are HLA-A1, A29, B37, B44 and C6. Four other melanomas of patients that had A1 in common with MZ2 were cotransfected with the 2.4 kb fragment and pSVtkneoβ. Three of them yielded neo$^r$ transfectants that stimulated TNF release by anti-E CTL clone 82/30, which is CD8+ (FIG. 11). No E- transfectant was obtained with four other melanomas, some of which shared A29, B44 or C6 with MZ2. This suggests that the presenting molecule for antigen MZ2-E is HLA-A1. In confirmation, it was found that, out of 6 melanoma cell lines derived from tumors of HLA-A1 patients, two stimulated TNF release by anti-E CTL clone 82/30 of patient MZ2. One of these tumor cell lines, MI13443-MEL, also showed high sensitivity to lysis by these anti-E CTL. These two melanomas were those that expressed mage-1 gene (FIG. 11). Eight melanomas of patients with HLA haplotypes that did not include A1 were examined for their sensitivity to lysis and for their ability to stimulate TNF release by the CTL. None was found to be positive. The ability of some human anti-tumor CTL to lyse allogeneic tumors sharing an appropriate HLA specificity with the original tumor has been reported previously (Darrow, et al., J. Immunol. 142: 3329 (1989)). It is quite possible that antigenic peptides encoded by genes mage 2 and 3 can also be presented to autologous CTL by HLA-A1 or other class I molecules, especially in view of the similar results found with murine tumors, as elaborated upon supra.

EXAMPLE 27

As indicated supra, melanoma MZ2 expressed antigens F, D and A', in addition to antigen E. Following the isolation of the nucleic acid sequence coding for antigen E, similar experiments were carried out to isolate the nucleic acid sequence coding for antigen F.

To do this, cultures of cell line MZ2-MEL2.2, an E⁻ cell line described supra, were treated with anti-F CTL clone 76/6, in the same manner described for treatment with anti-E CTL clones. This resulted in the isolation of an F antigen loss variant, which was then subjected to several rounds of selection. The resulting cell line, "MZ2-MEL2.2.5" was completely resistant to lysis by anti-F CTLs, yet proved to be lysed by anti-D CTLs.

Again, following the protocols set forth for isolation of antigen −E precursor DNA, the F⁻ variant was transfected with genomic DNA from F⁺ cell line MZ2-MEL3.0. The experiments yielded 90,000 drug resistant transfectants. These were tested for MZ2-F expression by using pools of 30 cells in the TNF detection assay elaborated upon supra. One pool stimulated TNF release by anti-F CTLs, and was cloned. Five of 145 clones were found to stimulate anti-F CTLs. Lysis assays, also following protocols described supra, confirmed (i) expression of the gene coding for antigen F, and (ii) presentation of antigen F itself.

EXAMPLE 28

Following identification of F⁺ cell lines, the DNA therefrom was used to transfect cells. To do this, a cosmid library of F⁺ cell line MZ2-MEL.43 was prepared, again using the protocols described supra. The library was divided into 14 groups of about 50,000 cosmids, and DNA from each group was transfected into MZ2-MEL2.2.5. Transfectants were then tested for their ability to stimulate TNF release from anti-F CTL clone 76/6. Of 14 groups of cosmids, one produced two independent transfectants expressing antigen F; a yield of two positives out of 17,500 geniticin resistant transfectants.

EXAMPLE 29

The existence of a gene family was suggested by the pattern observed on the Southern blot (FIG. 12). To do this, the 2.4 kb BamHI fragment, which transferred the expression of antigen MZ2-E, was labelled with 32p and used as a probe on a Southern Blot of BamHI digested DNA of E+cloned subclone MZ2-MEL2.2. Hybridization conditions included 50 µl/cm² of 3.5×SSC, 1×Denhardt's solution; 25mM sodium phosphate buffer (pH 7.0), 0.5% SDS, 2 mM EDTA, where the 2.4 kb probes had been labelled with [α$^{32}$p]dCTP (2–3000 Ci/mole), at 3×10⁶ cpm/ml. Hybridization was carried out for 18 hours at 65° C. After this, the membranes were washed at 65° C. four times for one hour each in 2×SSC, 0.1% SDS, and finally for 30 minutes in 0.1×SSC, 0.1% SDS. To identify hybridization, membranes were autoradiographed using Kodak X-AR film and Kodak X-Omatic fine intensifying screens.

In the following examples, whenever "hybridization" is referred to, the stringency conditions used were similar to those described supra. "Stringent conditions" as used herein thus refers to the foregoing conditions; subject to routine, art recognized modification.

EXAMPLE 30

The cDNA coding for mage 4 was identified from a sample of the human sarcoma cell line LB23-SAR. This cell line was found to not express mage 1, 2 or 3, but the mRNA of the cell line did hybridize to the 2.4 kb sequence for mage 1. To study this further, a cDNA library was prepared from total LB23-SAR mRNA, and was then hybridized to the 2.4 kb fragment. A cDNA sequence was identified as hybridizing to this probe, and is identified hereafter as mage 4.

EXAMPLE 31

Experiments were carried out using PHA-activated lymphocytes from patient "MZ2", the source of the "MZ" cells discussed supra An oligonucleotide probe which showed homology to mage 1 but not mage 2 or 3 was hybridized with a cosmid library derived from the PHA activated cells. The size of the hybridizing BamHI cosmid fragment, however, was 4.5 kb, thus indicating that the material was not mage 1; however, on the basis of homology to mage 1–4, the fragment can be referred to as "mage 5". The sequence of MAGE 5 is presented in SEQ ID NO: 16.

EXAMPLE 32

Melanoma cell line LB-33-MEL was tested. Total mRNA from the cell line was used to prepare cDNA, which was then amplified with oligos CHO9: (ACTCAGCTCCTC-CCAGATTT) SEQ ID NO: 47, and CHO10: (GAAGAG-GAGGGGCCAAG) SEQ ID NO: 48. These oligos correspond to regions of exon 3 that are common to previously described mage 1, 2 and 3.

To do this, 1 µg of RNA was diluted to a total volume of 20 µl , using 2 µl of 10× PCR buffer, 2 µl of each of 10 mM dNTP, 1.2 µl of 25 mM MgCl₂, 1 µl of an 80 mM solution of CHO9, described supra, 20 units of RNAsin, and 200 units of M.MLV reverse transcriptase. This was followed by incubation for 40 minutes at 42° C. PCR amplification followed, using 8 µl of 10× PCR buffer, 4.8 µl of 25 mM MgCl₂, 1 µl of CHO10, 2.5 units of Thermus acquaticus ("Taq") polymerase, and water to a total volume of 100 µl. Amplification was then carried out for 30 cycles (1 minute 94° C.; 2 minutes at 52° C., 3 minutes at 72° C.). Ten µl of each reaction were then size fractionated on agarose gel, followed by nitrocellulose blotting. The product was found to hybridize with oligonucleotide probe CHO18 (TCTTG- TATCCTGGAGTCC). This probe identified mage 1 but not mage 2 or 3. However, the product did not hybridize to probe SEQ 4 (TTGCCAAGATCTCAGGAA). This probe also binds mage 1 but not 2 and 3. This indicated that the PCR product contained a sequence that differed from mage 1, 2 and 3. Sequencing of this fragment also indicated differences with respect to mage 4 and 5. These results indicate a sequence differing from previously identified mage 1, 2, 3, 4 and 5, and is named mage 6.

EXAMPLE 33

In additional experiments using cosmid libraries from PHA-activated lymphocytes of MZ2, the 2.4 kb mage 1 fragment was used as a probe and isolated a complementary fragment. This clone, however, did not bind to oligonucleotides specific for mage 1, 2, 3 or 4. The sequence obtained shows some homology to exon 3 of mage 1, and differs from mages 1–6. It is referred to as mage 7 hereafter. Additional screenings yielded mage 8–11.

EXAMPLE 34

The usefulness of the TRAPs, as well as TRAs derived therefrom, was exemplified by the following.

Exon 3 of mage 1 was shown to transfer expression of antigen E. As a result, it was decided to test whether synthetic peptides derived from this exon 3 could be used to confer sensitivity to anti-E CTL.

To do this, and using standard protocols, cells normally insensitive to anti-E/CTLs were incubated with the synthetic peptides derived from Exon 3.1. Using the CTL lytic assays described supra on P815A, and a peptide concentration of 3 mM, the peptide Glu-Ala-Asp-Pro-Thr-Gly-His-Ser-Tyr was shown to be best. The assay showed lysis of 30%, indicating conferring of sensitivity to the anti-E CTL.

EXAMPLE 35

Nucleic acid sequences referred to as "smage" were isolated from murine cells. Using the protocols described supra, a cosmid library was prepared from the DNA of normal DBA/2 kidney cells, using cosmid vector C2RB. As a probe, the 2.4 kb BamHI fragment of MAGE-1 was used. The DNA was blotted to nylon filters, and these were washed in 2×SSC at 65° C. to identify the smage material.

EXAMPLE 36

Further tissue samples were tested for the presence of MAGE genes, using the protocols discussed supra. Some of these results follow.

There was no expression of the MAGE genes in brain or kidney tumor tissue. Colon tumor tissue showed expression of MAGE 1, 2, 3 and 4, although not all tumors tested showed expression of all MAGE genes. This is also true for pancreatic tumor (MAGE 1); non-small cell lung (MAGE 1, 2, 3 and 4), prostate (MAGE 1), sarcomas (MAGE 1, 2, 3 and 4), breast (MAGE 1, 2 and 3), and larynx (MAGE 1 and 4).

EXAMPLE 37

A cytolytic CTL clone "20/38" was obtained from peripheral blood lymphocytes of melanoma patient MZ2. This clone is described by Van den Eynde et al., Int. J. Cancer 44: 634–640 (1989), the disclosure of which is incorporated by reference. The CTL clone has been isolated following Herin et al., Int. J. Cancer 39: 390–396 (1987), which is incorporated by reference. The assay is described herein, however. Autologous melanoma cells were grown in vitro, and then resuspended at $10^7$ cells/ml in DMEM, supplemented with 10 mM HEPES and 30% FCS, and incubated for 45 minutes at 37° C. with 200 µCi/ml of Na($^{51}$Cr)O$_4$. Labelled cells were washed three times with DMEM, supplemented with 10 mM HEPES. These were then resuspended in DMEM supplemented with 10 mM HEPES and 10% FCS, after which 100 µl aliquots containing $10^3$ cells, were distributed into 96 well microplates. Samples of the CTL clone were added in 100 ul of the same medium, and assays were carried out in duplicate. Plates were centrifuged for four minutes at 100 g, and incubated for four hours at 37° C. in a 5.5% CO$_2$ atmosphere.

Plates were centrifuged again, and 100 ul aliquots of supernatant were collected and counted. Percentage of $^{51}$Cr release was calculated as follows:

$$\%\ ^{51}\text{Cr release} = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology.

The same method was used to test target K562 cells. When EBV-B cells were used, the only change was the replacement of DMEM medium by Hank's medium, supplemented with 5% FCS.

These experiments led to isolation of CTL clone 20/38.

Figure 1B:
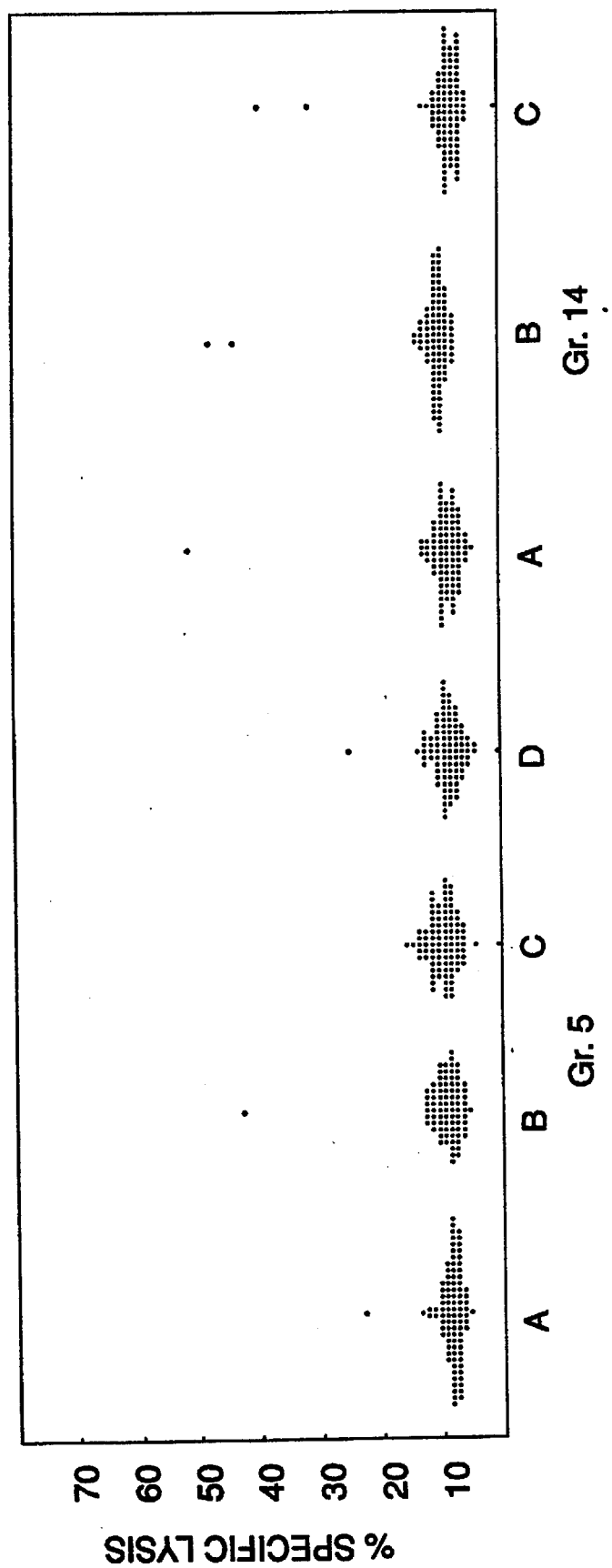

FIG. 1 presents the results of these assays. Specifically, it will be seen that the CTL clone lysed autologous melanoma cell line MZ2-MEL.3.0, but did not lyse EBV-B cell lines, fibroblasts, K562 or non-autologous melanoma cell line SK-MEL-29.

EXAMPLE 38

Once the CTL clone was recognized as being specific for the autologous cell line, it was tested for antigenic specificity. To do this, antigen loss variants derived from Melanoma cell line MEL MZ2 were tested in the same type of chromium release assay described above. These target lines were MZ2-MEL 3.0, which is D$^+$, E$^+$, F$^+$, A$^+$, MZ2-MEL.61, which is D$^-$, MZ2-MEL 2.2, which is E$^-$, and MZ2-MEL.4, which is F$^-$. In addition to CTL clone 20/38, clones which are known to be anti-A (CTL 28/336), anti-F (CTL 76/6), and anti-E (CTL 22/13) were tested.

These results are set forth in FIG. 15. It will be seen that CTL clone 20/38 lysed all the cell lines leading to chromium release except D$^-$ cell line MZ2-MEL.61, thus indicating that the CTL clone is anti-D. This result was confirmed, in experiments not included herein, by experiments where TNF release by the CTL clone was observed only in the presence of melanoma lines presenting antigen D.

EXAMPLE 39

Once antigen D was identified as the target molecule, studies were carried out to determine the HLA type which presented it. The experiments described in example 38 showed that antigen D was presented by MZ2-MEL, and this cell line's HLA specificity is known (i.e., A1, A29, B37, B44, Cw6, C.cl.10). It was also known, however, that a variant of MZ2-MEL which had lost HLA molecules A29, B44 and C.cl.10 still expressed antigen D, so these could be eliminated from consideration. Studies were not carried out on lines expressing B37, as none could be found.

In all, 13 allogeneic lines were tested, which expressed either HLA-A1 (10 of 13), or Cw6 (3 of 13). The cell lines were tested for their ability to stimulate release of TNF by CTL clone 20/38, using the method of Traversari et al., Immunogenetics 35: 145–152 (1992), the disclosure of which is incorporated by reference. This assay measures TNF release via testing toxicity of supernatants on WEHI 164–13 cells.

In the assays, cell samples (3000, 10,000 or 30,000 cells) from the allogeneic lines were cultured in the presence of 1500 cells of the CTL clone, and 25 u/ml of IL-2. Twenty-four hours later, the supernatant from the culture was tested against the WEHI cells for toxicity. The results are presented in Table 3, which follows.

Eight cell lines were found to stimulate TNF release from the CTL clone 20/38. All of these lines were HLA-A1. None of the Cw6 presenting lines did so.

The cell lines were also assayed to determine MAGE expression. All eight of the lines which stimulated TNF release expressed MAGE-3, whereas the two HLA-A1 lines which were negative did not.

TABLE 3

| Melanoma | Number of Cells | TNF pg/ml Exp 1 | +CTL 20/38 | TNF pg/ml Exp 2 | +CTL 20/38 | Expression of Mage-3 | Expression of HLA-A-1 |
|---|---|---|---|---|---|---|---|
| MZ2-MEL.61.2 | 50000 | | 1 | | 4 | +++ | + |
| MZ2-MEL-ET1 | 50000 | | >120 | | >120 | +++ | + |
| | 1666 | | 66 | | >120 | | |
| LY-1-MEL | 30000 | 1 | >120 | 1 | >120 | +++ | + |
| | 10000 | 1 | >120 | 1 | >120 | | |
| | 3000 | <1 | 114 | 2 | >120 | | . |
| MI-10221 | 30000 | <1 | >120 | | | +++ | + |
| | 10000 | <1 | 71 | | | | |
| | 3000 | <1 | 74 | | | | |
| LY-2-MEL | 30000 | 1 | 57 | | | +++ | + |
| | 10000 | 1 | 86 | | | | |
| | 3000 | 1 | 91 | | | | |
| LY-4-MEL | 30000 | 1 | >120 | | | +++ | + |
| | 10000 | 1 | >120 | | | | |
| | 3000 | 1 | >120 | | | | |
| SK23-MEL | 30000 | 1 | 112 | | | +++ | + |
| | 10000 | 1 | 116 | | | | |
| | 3000 | 1 | 105 | | | | |
| MI-665/2-MEL | 30000 | 1 | 3 | 2 | 4 | – | + |
| | 10000 | 1 | 2 | 2 | 5 | | |
| | 3000 | 1 | 5,2 | 1 | 5 | | |
| LB34-MEL | 30000 | 1 | >120 | | | +++ | + |
| | 10000 | 1 | >120 | | | | |
| | 3000 | 1 | >120 | | | | |
| LB45-MEL | 30000 | 1 | 11 | 1 | 30 | – | + |
| | 10000 | 1 | 6 | 1 | 12 | | |
| | 3000 | 1 | 2 | <1 | 7 | | |
| NA-6-MEL | 30000 | 1 | 77 | 5 | 98 | +++ | + |
| | 10000 | 1 | 104 | 5 | >120 | | |
| | 3000 | 1 | 110 | 4 | >120 | | |
| MI-13443-MEL | 30000 | 1 | >120 | | | +++ | + |
| | 10000 | 1 | >120 | | | | |
| | 3000 | 1 | >120 | | | | |
| LB5-MEL | 30000 | 1 | 8 | 4 | 9 | + | – |
| | 10000 | <1 | 5 | 4 | 11 | | |
| | 3000 | <1 | 5 | 1 | 5 | | |
| SK64-MEL | 30000 | 1 | 4 | 2 | 5 | ? | – |
| | 10000 | 1 | 2 | 1 | 5 | | |
| | 3000 | 1 | 1 | 1 | 4 | | |
| LB33-MEL | 30000 | | | 1 | 3,5 | +++ | – |
| | 10000 | | | 1 | 4 | | |
| | 3000 | | | 1 | 3 | | |
| LB73-MEL | 50000 | | 16 | | | – | – |

1500 CTL 20/38 and 25μ/ml IL2 were mixed with the indicated number of cell of the different allogeneic melanomas. 24 hours later, the amount of TNF present in the supernatant was assayed by testing its cytotoxicity for WEHI-164-13 cells.

EXAMPLE 40

In view of the results set forth in example 39, experiments were carried out to determine if antigen D was in fact a tumor rejection antigen derived from MAGE-3. To do this, recipient COS7 cells were transfected with 100 ng of the gene for HLA-A1 cloned into pcDNA I/Amp, and 100 ng of one of (a) cDNA for MAGE-1 cloned into pcDNA I/Amp, (b) cDNA for MAGE-2 cloned into pcDSRα, or (c) cDNA for MAGE-3 cloned into pcDSRα. The transfecting sequences were ligated into the plasmids in accordance with manufacturer's instructions. Samples of COS-7 cells were seeded, at 15,000 cells/well into tissue culture flat bottom microwells, in Dulbeco's modified Eagles Medium ("DMEM") supplemented with 10% fetal calf serum. The cells were incubated overnight at 37° C., medium was removed and then replaced by 30 μl/well of DMEM medium containing 10% Nu serum, 400 μg/ml DEAE-dextran, 100 μM chloroquine, and the plasmids described above. Following four hours of incubation at 37° C., the medium was removed, and replaced by 50 μl of PBS containing 10% DMSO. This medium was removed after two minutes and replaced by 200 μl of DMEM supplemented with 10% of FCS.

Figure 16:
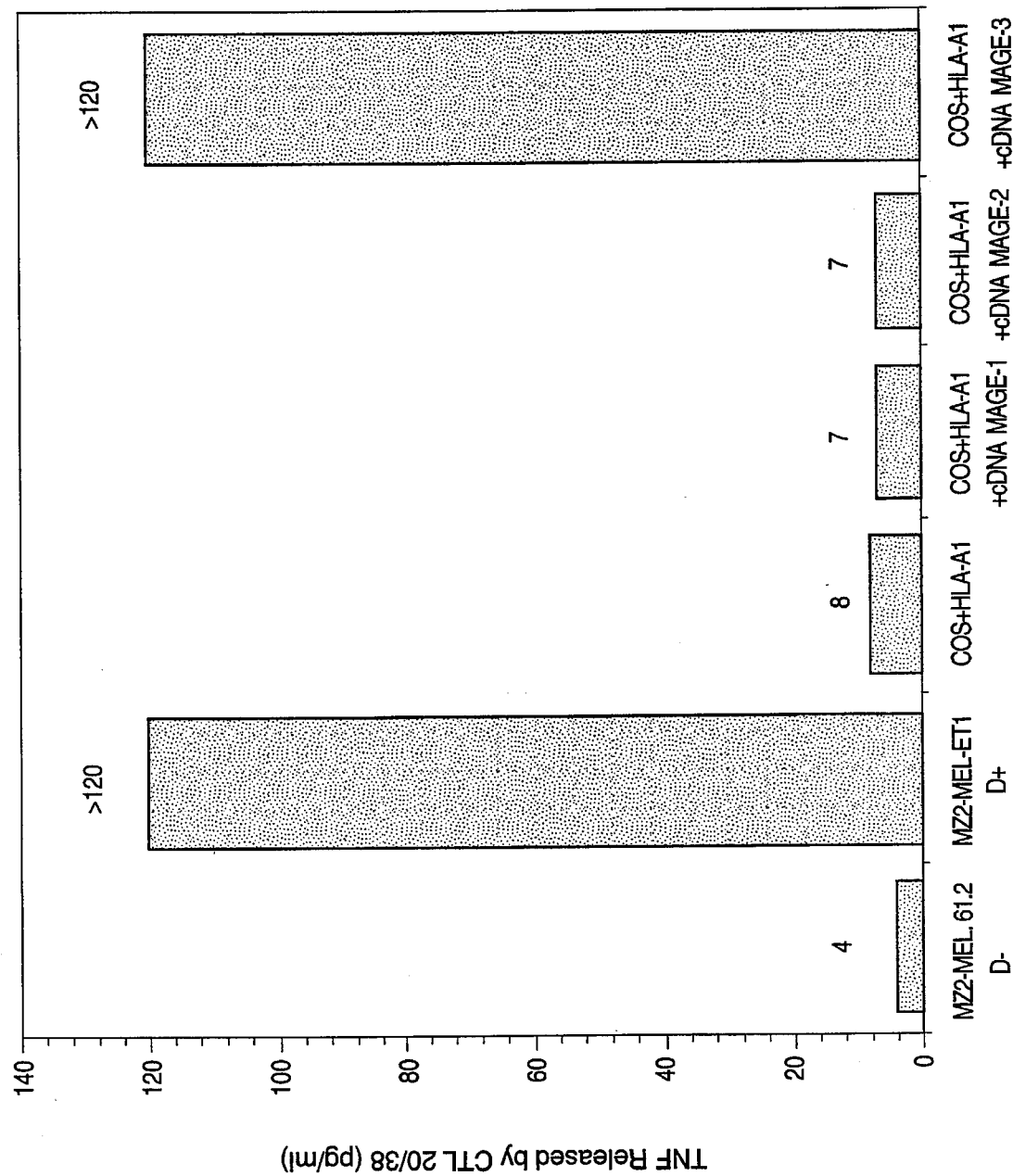
FIG. 16 shows the results obtained when a TNF release assay was carried out on various transfected cells.

Following this change in medium, COS cells were incubated for 24 hours at 37° C. Medium was then discarded, and 1500 cells of CTL clone 20/38 were added, in 100 μl of Iscove is medium containing 10% pooled human serum, supplemented with 25 u/ml of IL-2. Supernatant was removed after 24 hours, and TNF content was determined in an assay on WEHI cells, as described by Traversari et al., Immunogenetics 35: 145–152 (1992), the disclosure of which is incorporated by reference. These results are shown in FIG. 16.

It will be seen that the CTL clone was strongly stimulated by COS7 cells transfected with HLA-A1 and MAGE-3, but not by the cells transfected with the other mage genes. This leads to the conclusion that antigen D is a tumor rejection antigen derived from the tumor rejection antigen precursor coded by gene MAGE-3, and that this TRA is presented by HLA-A1 molecules.

EXAMPLE 41

It is well known that different alleles of genes may produce different proteins. This principle should extend to the MAGE family of genes as well, and is an important consideration in view of diagnostic and therapeutic ramifications. Thus, polymorphism in the MAGE family was studied.

To address the issue of polymorphism, blood lymphocytes of ten individuals were collected, and genomic DNA extracted. This DNA was subjected to Southern blotting in accordance with James et al., Canc. Res. 48: 5546–5551 (1988), incorporated by reference. Briefly, the labelled 2.4 kb genomic DNA fragment of MAGE-1, containing the last two exons of MAGE-1, described supra, was hybridized with the filter carrying the digested DNA, at 42° C. for at least 16 hours, in 50% formamide, 5% dextran sulfate, 6×SSC, 1% SDS and 0.1 mg/ml heterologous DNA. The hybridization filters were washed, consecutively, in 2×SSC, 0.1% SDS (room temperature, 15 minutes), and twice in 0.1×SSC, 0.1% SDS at 67° C. for 30 minutes, each wash. Autoradiography was carried out at −70° C. for 7–10 days, using standard film.

A pattern of 13 hybridizing bands was observed, which was conserved over all individuals. One individual did show an additional band, but also showed the 13 band pattern.

EXAMPLE 42

It was of interest to determine which chromosome or chromosomes bear the MAGE genes. To ascertain this, a panel of hamster/human somatic cell hybrids was used. The hybrids were obtained either from the Human Genetic Mutant Cell Repository ("GM" prefix), or from Johns Hopkins University ("$A_3$" prefix) Each hybrid was cytogenetically studied to determine human chromosome content.

Total genomic DNA of the hybrids was probed in the same manner described in Example 41, supra (the conditions of stringency used prevented cross hybridization with hamster DNA).

Table 4, which follows, summarizes the result of the probe work. Analysis of the data led to the conclusion that the pattern of hybridization was only concordant with location of MAGE-1 on the X chromosome.

TABLE 4

Segregation of MAGE −1 with human chromosomes in human — hamster hybrid cell DNA

| Hybrid | Human chromosome MAGE −1 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y |
|---|---|---|---|---|---|---|---|---|---|---|---|---|---|---|---|---|---|---|---|---|---|---|---|---|---|
| GM06317 | − | − | − | − | − | − | − | − | − | − | − | − | − | − | − | − | − | − | − | − | − | − | − | − | − | + |
| GM06318B | + | − | − | − | − | − | − | − | − | − | − | − | − | − | − | − | − | − | − | − | − | − | − | − | + | − |
| GM07300 | + | − | − | − | − | − | − | + | − | + | − | − | + | − | − | − | − | − | − | − | − | − | − | − | + | − |
| GM07301 | + | − | − | − | − | − | − | − | − | − | − | − | + | − | − | − | − | − | − | − | − | − | − | − | + | − |
| GM08854 | − | − | − | − | − | − | − | − | − | − | − | − | − | − | − | − | − | − | − | − | − | + | − | − | − | − |
| GM09142 | − | − | − | + | − | + | − | − | − | − | − | − | − | − | − | − | − | − | − | − | − | 1 | − | 2 | − |
| GM10095 | + | − | − | − | − | − | − | − | − | 3 | − | − | − | − | − | − | − | − | − | − | − | − | − | − | 4 | − |
| GM10115 | − | − | − | − | + | − | − | − | − | − | − | − | − | − | − | − | − | − | − | − | − | − | − | − | − | − |
| GM10156B | − | − | − | − | − | − | − | + | − | − | − | − | − | − | − | − | − | − | − | − | − | − | − | − | − | − |
| GM10253 | − | − | − | + | − | − | − | − | − | − | − | − | − | − | − | − | − | − | − | − | − | − | − | − | − | − |
| GM10322 | − | − | − | − | − | − | − | − | − | − | − | − | − | − | − | − | − | − | − | − | − | − | + | + | − | − |
| GM10478 | − | − | − | − | + | − | − | − | − | − | − | − | − | − | − | − | − | − | − | − | + | − | − | − | − | − |
| GM10479 | − | − | − | − | − | − | − | − | − | − | − | − | − | − | + | − | − | − | − | − | − | − | − | − | − | − |
| GM10498 | − | − | − | − | − | − | − | − | − | − | − | − | − | − | − | − | − | + | − | − | − | − | − | − | − | − |
| GM10567 | − | − | − | − | − | − | − | − | − | − | − | − | − | − | − | − | + | − | − | − | − | − | − | − | − | − |
| GM10611 | − | − | − | − | − | − | − | − | − | + | − | − | − | − | − | − | − | − | − | − | − | − | − | − | − | − |
| GM10612 | − | − | − | − | − | − | − | − | − | − | − | − | − | − | − | − | − | − | − | + | − | − | − | − | − | − |
| GM10629 | − | − | − | − | − | − | + | − | − | − | − | − | − | − | − | − | − | − | − | − | − | − | − | − | − | − |
| GM10791 | − | − | − | − | − | − | − | + | − | − | − | − | − | − | − | − | − | − | − | − | − | − | − | − | − | − |
| GM10880 | − | + | − | − | − | − | − | − | − | − | − | − | − | + | + | − | − | − | − | − | − | − | − | − | − | − |
| GM10888 | − | − | − | − | − | − | − | − | − | − | − | − | − | − | − | − | − | − | − | − | − | − | − | + | − | − |
| $A_3$ADA ID12 | − | + | − | + | + | + | − | − | + | − | − | − | + | + | + | − | + | − | − | − | + | + | − | − | − | + |
| $A_3$ADA6F5 | + | + | + | − | − | + | + | + | + | − | − | − | + | + | + | + | − | + | + | + | − | + | + | + | + | + |
| $A_3$ADA13 | + | + | − | + | + | − | − | + | + | − | − | + | + | + | + | + | ± | − | − | + | − | + | − | + | + | + |
| $A_3$ADA14 | − | − | − | + | + | + | − | − | + | − | + | + | + | + | + | ± | − | − | − | − | + | + | + | − | + |
| $A_3$G1 | + | − | − | + | + | − | 6 | − | ± | + | + | − | − | − | − | ± | − | + | − | ± | + | − | ± | + | + |
| $A_3$HR20 | − | − | − | + | + | + | + | − | − | + | − | − | − | + | − | + | − | − | − | − | − | − | ± | − | − |
| PgMe4 | + | − | 5 | + | − | − | + | + | + | − | − | + | + | + | + | − | + | − | − | ± | + | − | ± | + |
| Number of concordant hybrids | (+/+) | 2 | 1 | 3 | 2 | 1 | 3 | 3 | 4 | 2 | 1 | 3 | 4 | 3 | 3 | 3 | 0 | 3 | 1 | 2 | 1 | 3 | 1 | 8 | 4 |
| | (−/−) | 17 | 19 | 14 | 14 | 15 | 18 | 18 | 16 | 17 | 18 | 17 | 17 | 16 | 14 | 18 | 17 | 17 | 19 | 18 | 16 | 14 | 15 | 18 | 17 |
| Number of | (+/−) | 6 | 6 | 5 | 6 | 7 | 3 | 5 | 3 | 6 | 7 | 5 | 4 | 5 | 5 | 4 | 7 | 5 | 7 | 5 | 6 | 5 | 6 | 0 | 4 |

TABLE 4-continued

Segregation of MAGE −1 with human chromosomes in human — hamster hybrid cell DNA

| Hybrid | Human chromosome MAGE −1 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y |
|---|---|---|---|---|---|---|---|---|---|---|---|---|---|---|---|---|---|---|---|---|---|---|---|---|---|
| discordant hybrids | (−/+) | 2 | 0 | 5 | 5 | 4 | 2 | 1 | 3 | 2 | 1 | 2 | 2 | 3 | 5 | 0 | 2 | 2 | 0 | 1 | 3 | 5 | 3 | 0 | 2 |
| Percent discordancy | | 22 | 23 | 38 | 37 | 41 | 24 | 22 | 23 | 30 | 30 | 26 | 22 | 30 | 37 | 16 | 33 | 26 | 27 | 23 | 35 | 37 | 36 | 0 | 26 |

+ = chromosome present;
− = chromosome absent;
± = very faint bands, indicating that only a small percentage of the cells contained the chromosome (not included in calculation of percent discordancy)
1,2 — GM09142 contains only part of chromosomes X and 21, der 21 t(X;21)(p21;p12)
3,4 — GM10095 contains only part of chromosomes X and 9, der 9 t(X;9)(q13;q34)
5 — PgMe4 contains a deleted chromosome 2 and is missing 2p23–p24
6 — A₃G1 contains only the q arm of chromosome 6

EXAMPLE 43

In this experiment, a study was carried out to determine if all twelve known MAGE genes were located on the X chromosome. This was accomplished Via the use of polymerase chain reaction ("PCR") technology.

RNA purification and cDNA synthesis were first carried out, in accordance with Weynants et al., Int. J. Cancer 56: 826–829 (1994), incorporated by reference herein. Next, 1/20 of the cDNA produced from 2 ug of total RNA was supplemented with 5 ul of PCR buffer (500 mM KCl, 100 mM Tris pH 8.3), 1 ul each of 10 mM dNTPs, 25 pmoles of each primer (see below), 3 ul of 25 mM MgCl₂, and 1.25 units of Taq polymerase, with water added to final volume of 50 ul.

The primers were as follows:
MAGE-3: 5'-TGGAGGACCAGAGGCCCCC, 5-GGAC-GATTATCAGGAGGCCTGC (725 bp) (SEQ ID NOS: 27 and 28)
MAGE-4: 5'-GAGCAGACAGGCCAACCG, 5'-AAG-GACTCTGCGTCAGGC (446 bp) (SEQ ID NOS: 29 and 30)
MAGE-5: 5'-CTAGAGGAGCACCAAAGGAGAAG, 5'-TGCTCGGAACACAGACTCTGG (413 bp) (SEQ ID NOS: 31 and 32)
MAGE-6: 5'-TGGAGGACCAGAGGCCCCC, 5'-CAG-GATGATTATCAGGAAGCCTGT (727 bp) (SEQ ID NOS: 33 and 34)
MAGE-7: 5'-CAGAGGAGCACCGAAGGAGAA, 5'-CAGGTGAGCGGGGTGTGTC (405 bp) (SEQ ID NO: 35 and 36)
MAGE-8: 5'-CCCCAGAGAAGCACTGAAGAAG, 5'-(399 bp) (SEQ ID NOS: 37 and 38)
MAGE-9: 5'-CCCCAGAGCAGCACTGACG, 5'-CAGCT-GAGCTGGGTCGACC (391 bp) (SEQ ID NOS: 39 and 40)
MAGE-10: 5'-CACAGAGCAGCAGCACTGAAGGAG, 5'-CTGGGTAAAGACTCACTGTCTGG (485 bp) (SEQ ID NOS: 41 and 42)
MAGE-11: 5'-GAGAACCCAGAGGATCACTGGA, 5'-GGGAAAAGGACTCAGGGTCTATC (422 bp) (SEQ ID NOS: 43 and 44)
MAGE-12: 5'-GGTGGAAGTGGTCCGCATCG, 540 -GC-CCTCCACTGATCTTTAGCAA (392 bp) (SEQ ID NOS: 45 and 46)

Amplification was carried out for 30 cycles (MAGE-3, 4, 6, 12) or 32 cycles (MAGE-5, 7–11), where a cycle was one minute at 94° C. followed by two minutes at 65° C. for MAGE-5, 7–12, or two minutes at 68° C. (MAGE-4), or two minutes at 71° C. (MAGE-3 and MAGE-6); followed by three minutes at 72° C. (MAGE-3, 5–12), or two minutes at 72° C. (MAGE-4). The analysis was carried out on hybrid cell line GM 10868, which contains human chromosome 12, and GM 07301, which contains chromosome 12 and the X-chromosome. All assays were negative with the human GM 10868 line, and all were positive with the GM 07301 cell line, which indicated that all 12 genes are found on the X-chromosome.

EXAMPLE 44

The sizes of mRNAs for the different MAGE genes are similar, and thus Northern blot analysis cannot be used to determine expression of the various MAGE genes in different tissues, both normal and tumor. PCR analysis, along the lines of the study in example 43, supra, however, was believed to be useful.

To this end, a series of various tumors and normal tissues were tested for expression of MAGE genes.

Total RNA of the cells tested was extracted, and was then oligo dT primed, following art known techniques. The resulting material was then subjected to PCR, following the protocols of example 43, supra. For MAGE-1 and MAGE-2, the protocols of Brasseur et al., Int. J. Cancer. 52: 839–841 (1992), and DeSmet et al., Immunogenetics 39: 121–120 (1994), both of which are incorporated by reference, were used.

Table 5, which follows, elaborates these results, with a representative but by no means exhaustive listing of tissues tested. Each of MAGE 1–4, 6 and 12 showed significant expression in a number of tumors of varied tissue types. MAGE-5 and 8–11 were expressed very weakly in all tissues tested, whereas MAGE-7 RNA was not detectable at all. With respect to normal tissues, including tissues taken from a >20 week fetus, all were negative for MAGE RNA but for testis and placenta. Testis expressed all MAGE genes but MAGE-7, while placenta expressed MAGE-3, 4, and 8–11.

TABLE 5

Expression of MAGE-1, 2, 3, 4, 6 and -12 by tumors and normal tissues

|  | MAGE 1 | MAGE 2 | MAGE 3 | MAGE 4 | MAGE 6 | MAGE 12 |
|---|---|---|---|---|---|---|
| COLON CARCINOMAS | | | | | | |
| MZ-CO-2 ¶ | ++ | ++ | + | − | − | + |
| SK-CO-11 ¶ | − | ++ | +++ | − | + | ++ |
| LB150** | − | − | − | + | − | − |
| HSR 320 ¶ | − | +++ | +++ | + | ++ | +++ |
| LEUKEMIAS | | | | | | |
| K562 ¶ | − | ++ | +++ | − | ++ | +++ |
| MELANOMAS | | | | | | |
| MI10221 ¶ | − | +++ | +++ | +++ | +++ | +++ |
| MZ2-MEL 3.0 ¶ | +++ | +++ | +++ | − | +++ | + |
| LB265** | − | ++ | − | − | − | + |
| LG7** | − | ++ | − | − | − | − |
| LG11** | ++ | ++ | ++ | − | − | +++ |
| LB271** | − | ++ | +++ | − | ++ | +++ |
| LUNG CANCERS | | | | | | |
| LB178 (NSCLC)** | ++ | − | − | +++ | − | − |
| LB175 (NSCLC)** | − | ++ | +++ | +++ | − | +++ |
| LB11 (SCLC) ¶ | ++ | +++ | +++ | − | − | +++ |
| LB12 (SCLC) ¶ | − | +++ | +++ | − | − | +++ |
| SARCOMAS | | | | | | |
| LB23 ¶ | − | − | − | ++ | − | − |
| LB408** | − | − | − | ++ | − | − |
| LB258** | + | ++ | + | − | − | ++ |
| BREAST CARCINOMAS | | | | | | |
| LB280** | ++ | − | ++ | − | − | + |
| LB284** | ++ | ++ | ++ | + | − | ++ |
| Stomach | − | − | − | − | − | − |
| Lung | − | − | − | − | − | − |
| Breast | − | − | − | − | − | − |
| Colon | − | − | − | − | − | − |
| Skin | − | − | − | − | − | − |
| Uterus | − | − | − | − | − | − |
| Testis | ++ | ++ | ++ | ++ | ++ | ++ |
| Thymocytes | − | − | − | − | − | − |
| EBV-lymphocytes | − | − | − | − | − | − |
| Foetal liver | − | − | − | − | − | − |
| Foetal brain | − | − | − | − | − | − |
| Placenta LB694 | − | − | + | +++ | − | − |

RNA from tumor cell lines (¶), tumor samples (**) and normal tissues were tested by RT-PCR for the expression of MAGE genes. PCR primers were chosen as indicated in methods. For MAGE-12, PCR amplification of RNA in the absence of reverse transcription indicated that in our conditions the contamination by genomic DNA was negligible. The level of expression evaluated by band intensity of PCR products fractionated in agarose gels is represented by +++, ++, +. Absence of product is indicated by −.

The foregoing disclosure, including the examples, places many tools of extreme value in the hands of the skilled artisan. To begin, the examples identify and provide a methodology for isolating nucleic acid molecules which code for tumor rejection antigen precursors as well as the nucleic acid molecules complementary thereto. It is known that DNA exists in double stranded form, and that each of the two strands is complementary to the other. Nucleic acid hybridization technology has developed to the point where, given a strand of DNA, the skilled artisan can isolate its complement, or synthesize it.

"Nucleic acid molecule" as used herein refers to all species of DNA and RNA which possess the properties discussed supra. Genomic and complementary DNA, or "cDNA" both code for particular proteins, and as the examples directed to isolation of MAGE coding sequences show, this disclosure teaches the artisan how to secure both of these.

Similarly, RNA molecules, such as mRNA can be secured. Again, with reference to the skilled artisan, once one has a coding sequence in hand, mRNA can be isolated or synthesized.

Complementary sequences which do not code for TRAP, such as "antisense DNA" or mRNA are useful, e.g., in probing for the coding sequence as well as in methodologies for blocking its expression.

It will also be clear that the examples show the manufacture of biologically pure cultures of cell lines which have been transfected with nucleic acid sequences which code for or express the TRAP molecules. Such cultures can be used as a source for tumor rejection antigens, e.g., or as therapeutics. This aspect of the invention is discussed infra.

Cells transfected with the TRAF coding sequences may also be transfected with other coding sequences. Examples of other coding sequences include cytokine genes, such as interleukins (e.g., IL-2 or IL-4), or major histocompatibility complex (MHC) or human leukocyte antigen (HLA) molecules. Cytokine gene transfection is of value because expression of these is expected to enhance the therapeutic efficacy of the biologically pure culture of the cells in vivo. The art is well aware of therapies where interleukin transfectants have been administered to subjects for treating cancerous conditions. In a particularly preferred embodiment, cells are transfected with sequences coding for each of (i) a TRAP molecule, (ii) an HLA/MHC molecule, and (iii) a cytokine.

Transfection with an MHC/HLA coding sequence is desirable because certain of the TRAs may be preferentially or specifically presented only by particular MHC/HLA molecules. Thus, where a recipient cell already expresses the MHC/HLA molecule associated with presentation of a TRA, additional transfection may not be necessary although further transformation could be used to cause over-expression of the antigen. On the other hand, it may be desirable to transfect with a second sequence when the recipient cell does not normally express the relevant MHC/HLA molecule. It is to be understood, of course, that transfection with one additional sequence does not preclude further transfection with other sequences.

The term "biologically pure" as used in connection with the cell line described herein simply means that these are essentially free of other cells. Strictly speaking, a "cell line" by definition is "biologically pure" but the recitation will establish this fully.

Transfection of cells requires that an appropriate vector be used. Thus, the invention encompasses expression vectors where a coding sequence for the TRAP of interest is operably linked to a promoter. The promoter may be a strong promoter, such as those well known to the art, or a differential promoter, i.e., one which is operative only in specific cell types. The expression vectors may also contain all or a part of a viral or bacterial genome, such as vaccinia virus or BCG. Such vectors are especially useful in preparing vaccines.

The expression vectors may incorporate several coding sequences, as long as the TRAP sequence is contained therein. The cytokine and/or MHC/HLA genes discussed supra may be included in a single vector with the TRAP sequence. Where this is not desired, then an expression system may be provided, where two or more separate vectors are used where each coding sequence is operably linked to a promoter. Again, the promoter may be a strong or differential promoter. Co-transfection is a well known technique, and the artisan in this field is expected to have this technology available for utilization. The vectors may be constructed so that they code for the TRA molecule directly, rather than the TRAP molecule. This eliminates the need for post-translational processing.

As the foregoing discussion makes clear, the sequences code for "tumor rejection antigen precursors" ("TRAPs") which, in turn, are processed into tumor rejection antigens ("TRAs"). Isolated forms of both of these categories are described herein, including specific examples of each. Perhaps their most noteworthy aspect is as vaccines for treating various cancerous conditions. The evidence points to presentation of TRAs on tumor cells, followed by the development of an immune response and deletion of the cells. The examples show that when various TRAs are administered to cells, a CTL response is mounted and presenting cells are deleted. This is behavior characteristic of vaccines, and hence TRAPs, which are processed into TRAs, and the TRAs themselves may be used, either alone or in pharmaceutically appropriate compositions, as vaccines. Similarly, presenting cells may be used in the same manner, either alone or as combined with ingredients to yield pharmaceutical compositions. Additional materials which may be used as vaccines include isolated cells which present the TRA molecule on their surface, as well as TRAP fragments, mutated viruses, especially etiolated forms, and transfected bacteria. "Fragments" as used herein refers to peptides which are smaller than the TRA, but which possess the properties required of a vaccine, as discussed supra. Another vaccine comprises or consists of complexes of TRA and HLA molecule. Vaccines of the type described herein may be used preventively, i.e., via administration to a subject in an amount sufficient to prevent onset of a cancerous condition.

The generation of an immune response, be it T-cell or B-cell related, is characteristic of the effect of the presented tumor rejection antigen. With respect to the B-cell response, this involves, inter alia, the generation of antibodies to the TRA, i.e., which specifically bind thereto. In addition, the TRAP molecules are of sufficient size to render them immunogenic, and antibodies which specifically bind thereto are a part of this invention. These antibodies may be polyclonal or monoclonal, the latter being prepared by any of the well recognized methodologies for their preparation which need not be repeated here. For example, mAbs may be prepared using an animal model, e.g., a Balb/C mouse or in a test tube, using, e.g., EBV transformants. In addition, antiserum may be isolated from a subject afflicted with a cancerous condition where certain cells present a TRA. Such antibodies may also be generated to epitopes defined by the interaction of TRA and HLA/MHC molecules.

Review of the foregoing disclosure will show that there are a number of facets to the system which may be referred to as "tumor rejection antigen presentation and recognition". Recognition of these phenomena has diagnostic consequences. For example, the existence of specific CTL clones, or antibodies to the TRA makes it possible to diagnose or monitor cancerous conditions (explained infra), by monitoring the CTLs in a sample from a subject, binding of antibodies to TRAs, or the activity of anti-TRA CTLs in connection with subject samples. Similarly, the expression of nucleic acid molecules for TRAPs can be monitored via amplification (e.g., "polymerase chain reaction"), anti-sense hybridization, probe technologies, and so forth. Various subject samples, including body fluids (blood, serum, and other exudates, e.g.), tissues and tumors may be so assayed.

A particular manner of diagnosis is to use an adaptation of the standard "tuberculin test" currently used for diagnosis of tuberculosis. This standard skin test administers a stable form of "purified protein derivative" or "PPD" as a diagnostic aid. In a parallel fashion, TRAs in accordance with this invention may be used in such a skin test as a diagnostic aid or monitoring method.

The term "cancerous condition" is used herein to embrace all physiological events that commence with the initiation of the cancer and result in final clinical manifestation. Tumors do not spring up "ab initio" as visible tumors; rather there are various events associated with the transformation of a normal cell to malignancy, followed by development of a growth of biomass, such as a tumor, metastasis, etc. In addition, remission may be conceived of as part of "a cancerous condition" as tumors seldom spontaneously disappear. The diagnostic aspects of this invention include all events involved in carcinogenesis, from the first transformation to malignancy of a single cell, through tumor development and metastasis, as well as remission. All are embraced herein.

Where "subject" is used, the term embraces any species which can be afflicted with a cancerous condition. This includes humans and non-humans, such as domesticated animals, breeding stock, and so forth.

There are therapeutic aspects of this invention as well. The efficacy of administration of effective amounts of TRAPs and TRAs as vaccines has already been discussed supra. Similarly, one may develop the specific CTLs in vitro and then administer these to the subject. Antibodies may be administered, either polyclonal or monoclonal, which specifically bind to cells presenting the TRA of interest. These antibodies may be coupled to specific antitumor agents, including, but not being limited to, methotrexate radioiodinated compounds, toxins such as ricin, other cytostatic or cytolytic drugs, and so forth. Thus, "targeted" antibody therapy is included herein, as is the application of deletion of the cancerous cells by the use of CTLs.

The data from examples 37–40 show that a tumor rejection antigen derived from MAGE-3 is presented by HLA-A1 molecules. As such, in addition to the nucleic acid molecules coding for this TRAP, the TRAP itself as coded for by the sequences, vectors, cell lines, etcetera which incorporate this nucleic acid molecule, the invention also encompasses combination of the molecules coding for the MAGE-3 TRAP and HLA-A1. Thus, co-transfectants, vectors containing coding sequences for both, expression systems such as kits, or separate vectors, and so forth, are all embraced by the invention. Similarly, the vaccines discussed supra can be made by incorporating the TRAP from MAGE-3 and an adjuvant.

It is to be understood that a given TRAP may yield more than one TRA. In the case of MAGE-3, it has been shown that antigen D, as the term is used herein, derives therefrom, and one aspect of the invention is this isolated tumor rejection antigen. Another is isolated complexes of the TRA and its presenting molecule, i.e., HLA-A1.

The identification of MAGE-3 derived TRAs as being presented by HLA-A1 molecules suggests various therapeutic and diagnostic approaches. In a therapeutic context, e.g., the treatment of a disorder characterized by MAGE-3 expression may be treated in a number of ways, "disorder" being used to refer to any pathological condition where MAGE-3 TRAP is expressed, such as cancer (e.g., melanoma).

Therapeutic approaches based upon the disclosure are premised on a response by a subject's immune system, leading to lysis of TRA presenting cells, such as HLA-A1 cells. One such approach is the administration of CTLs specific to the complex to a subject with abnormal cells of the phenotype at issue. it is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917 (1986); Reddel et al., Science 257: 238 (Jul. 10, 1992); Lynch et al., Eur. J. Immunol. 21: 1403–1410 (1991); Kast et al., Cell 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the HLA/TRA complex. This can be determined very easily, as the art is very familiar with methods for identifying cells which present a particular HLA molecule, as well as how to identify cells expressing DNA containing the indicated sequences. Once isolated, such cells can be used with a sample of a subject's abnormal cells to determine lysis in vitro. If lysis is observed, then the use of specific CTLs in such a therapy may alleviate the condition associated with the abnormal cells. A less involved methodology examines the abnormal cells for HLA phenotyping, using standard assays, and determines expression via amplification using, e.g., PCR.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. U.S.A. 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into HLA-A1 presenting cells which present the HLA molecule of interest. The TRAP is processed to yield the peptide partner of the HLA molecule while the TRA is presented without the need for further processing. Thus, one may treat disorders where a MAGE-3 derived TRA is presented by HLA-A1 molecules, or by any HLA molecule.

In a diagnostic context, one may determine a disorder, as the term is used herein, by assaying for expression of the TRAP. This can be done directly (via, e.g., a PCR assay for TRAP sequences), or indirectly, via assaying for a MAGE-3 derived TRA, as the TRA's presence means that the TRAP is or was expressed.

It will be noted that two nucleic acid molecules are presented herein, i.e., MAGE-3 and MAGE-31, each of which code for TRAP MAGE-3. It is to be understood that when the expression "nucleic acid molecule which codes for MAGE-3 TRAP" is used, all molecules are covered which yield this molecule upon expression. Any number of variations, such as those showing codon degeneracy within the coding region, or variation within the introns, are covered by the invention.

Examples 41–44 provide information which permits the skilled artisan to identify when certain of the members of the MAGE gene family are expressed. In particular, various primers are taught which are useful in determining expression of MAGE genes. These primers are an additional feature of the invention, as is their use in assays such as amplification assays (e.g., polymerase chain reaction, ligase chain reaction), and so forth. They can also be used in standard hybridization assays, alone or in combinations. They can be combined in reagent kits, for example, where one or more pair of primers are presented, in appropriate containers, optionally with other reagents, such as nucleotide polymerases. Such kits are, of course, useful in the types of assays described herein.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated nucleic acid molecule selected from the group consisting of: SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 46.

2. Kit useful in determining expression of a MAGE gene, said kit comprising at least one pair of primers selected from the group consisting:
  (b) SEQ ID NO: 29 and SEQ ID NO: 30
  (c) SEQ ID NO: 31 and SEQ ID NO: 32
  (d) SEQ ID NO: 33 and SEQ ID NO: 34
  (e) SEQ ID NO: 35 and SEQ ID NO: 36
  (f) SEQ ID NO: 37 and SEQ ID NO: 38
  (g) SEQ ID NO: 39 and SEQ ID NO: 40
  (h) SEQ ID NO: 41 and SEQ ID NO: 42
  (i) SEQ ID NO: 43 and SEQ ID NO: 44 and
  (j) SEQ ID NO: 45 and SEQ ID NO: 46.

3. Method for determining expression of a MAGE gene of interest, comprising contacting a nucleic acid containing sample with at least one pair of primers selected from the group consisting:
  (b) SEQ ID NO: 29 and SEQ ID NO: 30
  (c) SEQ ID NO: 31 and SEQ ID NO: 32
  (d) SEQ ID NO: 33 and SEQ ID NO: 34
  (e) SEQ ID NO: 35 and SEQ ID NO: 36
  (f) SEQ ID NO: 37 and SEQ ID NO: 38
  (g) SEQ ID NO: 39 and SEQ ID NO: 40
  (h) SEQ ID NO: 41 and SEQ ID NO: 42
  (i) SEQ ID NO: 43 and SEQ ID NO: 44 and
  (j) SEQ ID NO: 45 and SEQ ID NO: 46, subjecting said nucleic acid containing sample and pair of primers to a reverse transcriptase-polymerase chain reaction, and determining any amplification product as a determination of expression of said MAGE gene.

* * * * *

UNITED STATES PATENT AND TRADEMARK OFFICE
CERTIFICATE OF CORRECTION

PATENT NO. : 5,612,201
DATED : March 18, 1997
INVENTOR(S) : Etienne De Plaen et al.

It is certified that error appears in the above-indentified patent and that said Letters Patent is hereby corrected as shown below:

Column 29, line 54: change "5'-CACAGAGCAGCAGCACTGAAGGAG" to --5'-CACAGAGCAGCACTGAAGGAG--.

Signed and Sealed this

Fifth Day of May, 1998

Attest:

BRUCE LEHMAN

Attesting Officer      Commissioner of Patents and Trademarks

SEQUENCE LISTING ( 1 ) GENERAL INFORMATION:

( i i i ) NUMBER OF SEQUENCES: 48

( 2 ) INFORMATION FOR SEQ ID NO: 1:

( i ) SEQUENCE CHARACTERISTICS:
        ( A ) LENGTH: 462 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 1:

```
ACCACAGGAG  AATGAAAAGA  ACCCGGGACT  CCCAAAGACG  CTAGATGTGT  GAAGATCCTG    60
ATCACTCATT  GGGTGTCTGA  GTTCTGCGAT  ATTCATCCCT  CAGCCAATGA  GCTTACTGTT   120
CTCGTGGGGG  GTTTGTGAGC  CTTGGGTAGG  AAGTTTTGCA  AGTTCCGCCT  ACAGCTCTAG   180
CTTGTGAATT  TGTACCCTTT  CACGTAAAAA  AGTAGTCCAG  AGTTACTAC   ACCCTCCCTC   240
CCCCCTCCCA  CCTCGTGCTG  TGCTGAGTTT  AGAAGTCTTC  CTTATAGAAG  TCTTCCGTAT   300
AGAACTCTTC  CGGAGGAAGG  AGGGAGGACC  CCCCCCCTTT  GCTCTCCCAG  CATGCATTGT   360
GTCAACGCCA  TTGCACTGAG  CTGGTCGAAG  AAGTAAGCCG  CTAGCTTGCG  ACTCTACTCT   420
TATCTTAACT  TAGCTCGGCT  TCCTGCTGGT  ACCCTTTGTG  CC                       462
```

( 2 ) INFORMATION FOR SEQ ID NO: 2:

( i ) SEQUENCE CHARACTERISTICS:
        ( A ) LENGTH: 675 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 2:

```
ATG  TCT  GAT  AAC  AAG  AAA  CCA  GAC  AAA  GCC  CAC  AGT  GGC  TCA  GGT  GGT     48
Met  Ser  Asp  Asn  Lys  Lys  Pro  Asp  Lys  Ala  His  Ser  Gly  Ser  Gly  Gly
                    5                   10                      15

GAC  GGT  GAT  GGG  AAT  AGG  TGC  AAT  TTA  TTG  CAC  CGG  TAC  TCC  CTG  GAA     96
Asp  Gly  Asp  Gly  Asn  Arg  Cys  Asn  Leu  Leu  His  Arg  Tyr  Ser  Leu  Glu
               20                   25                      30

GAA  ATT  CTG  CCT  TAT  CTA  GGG  TGG  CTG  GTC  TTC  GCT  GTT  GTC  ACA  ACA    144
Glu  Ile  Leu  Pro  Tyr  Leu  Gly  Trp  Leu  Val  Phe  Ala  Val  Val  Thr  Thr
          35                        40                  45

AGT  TTT  CTG  GCG  CTC  CAG  ATG  TTC  ATA  GAC  GCC  CTT  TAT  GAG  GAG  CAG    192
Ser  Phe  Leu  Ala  Leu  Gln  Met  Phe  Ile  Asp  Ala  Leu  Tyr  Glu  Glu  Gln
     50                        55                      60

TAT  GAA  AGG  GAT  GTG  GCC  TGG  ATA  GCC  AGG  CAA  AGC  AAG  CGC  ATG  TCC    240
Tyr  Glu  Arg  Asp  Val  Ala  Trp  Ile  Ala  Arg  Gln  Ser  Lys  Arg  Met  Ser
65                       70                  75                        80

TCT  GTC  GAT  GAG  GAT  GAA  GAC  GAT  GAG  GAT  GAG  GAT  GAC  TAC  TAC         288
Ser  Val  Asp  Glu  Asp  Glu  Asp  Asp  Glu  Asp  Glu  Asp  Asp  Tyr  Tyr
                    85                  90                      95

GAC  GAC  GAG  GAC  GAC  GAC  GAC  GAT  GCC  TTC  TAT  GAT  GAT  GAG  GAT  GAT    336
Asp  Asp  Glu  Asp  Asp  Asp  Asp  Ala  Phe  Tyr  Asp  Asp  Glu  Asp  Asp
                   100                 105                     110

GAG  GAA  GAA  GAA  TTG  GAG  AAC  CTG  ATG  GAT  GAT  GAA  TCA  GAA  GAT  GAG    384
Glu  Glu  Glu  Glu  Leu  Glu  Asn  Leu  Met  Asp  Asp  Glu  Ser  Glu  Asp  Glu
              115                      120                 125
```

| | | | | | | | | | | | | | | | | |
|---|---|---|---|---|---|---|---|---|---|---|---|---|---|---|---|---|
|GCC|GAA|GAA|GAG|ATG|AGC|GTG|GAA|ATG|GGT|GCC|GGA|GCT|GAG|GAA|ATG|432|
|Ala|Glu|Glu|Glu|Met|Ser|Val|Glu|Met|Gly|Ala|Gly|Ala|Glu|Glu|Met||
||130||||135||||140|||||||
|GGT|GCT|GGC|GCT|AAC|TGT|GCC|TGT|GTT|CCT|GGC|CAT|CAT|TTA|AGG|AAG|480|
|Gly|Ala|Gly|Ala|Asn|Cys|Ala|Cys|Val|Pro|Gly|His|His|Leu|Arg|Lys||
|145||||150|||||155|||||160||
|AAT|GAA|GTG|AAG|TGT|AGG|ATG|ATT|TAT|TTC|TTC|CAC|GAC|CCT|AAT|TTC|528|
|Asn|Glu|Val|Lys|Cys|Arg|Met|Ile|Tyr|Phe|Phe|His|Asp|Pro|Asn|Phe||
|||| |165||||170|||||175|||
|CTG|GTG|TCT|ATA|CCA|GTG|AAC|CCT|AAG|GAA|CAA|ATG|GAG|TGT|AGG|TGT|576|
|Leu|Val|Ser|Ile|Pro|Val|Asn|Pro|Lys|Glu|Gln|Met|Glu|Cys|Arg|Cys||
|||180|||||185|||||190|||
|GAA|AAT|GCT|GAT|GAA|GAG|GTT|GCA|ATG|GAA|GAG|GAA|GAA|GAA|GAA|GAG|624|
|Glu|Asn|Ala|Asp|Glu|Glu|Val|Ala|Met|Glu|Glu|Glu|Glu|Glu|Glu|Glu||
|||195|||||200||||210||||
|GAG|GAG|GAG|GAG|GAA|GAG|GAA|ATG|GGA|AAC|CCG|GAT|GGC|TTC|TCA|CCT|672|
|Glu|Glu|Glu|Glu|Glu|Glu|Glu|Met|Gly|Asn|Pro|Asp|Gly|Phe|Ser|Pro||
|220||||225||||230|||||235||
|TAG| | | | | | | | | | | | | | |675|

( 2 ) INFORMATION FOR SEQ ID NO: 3:

( i ) SEQUENCE CHARACTERISTICS:
  ( A ) LENGTH: 228 base pairs
  ( B ) TYPE: nucleic acid
  ( C ) STRANDEDNESS: single
  ( D ) TOPOLOGY: linear ( i i ) MOLECULE TYPE: genomic DNA ( x i ) SEQUENCE DESCRIPTION: SEQ ID NO: 3:

| | | | | |
|---|---|---|---|---|
|GCATGCAGTT|GCAAAGCCCA|GAAGAAAGAA|ATGGACAGCG|GAAGAAGTGG|TTGTTTTTTT|60|
|TTCCCCTTCA|TTAATTTTCT|AGTTTTAGT|AATCCAGAAA|ATTTGATTTT|GTTCTAAAGT|120|
|TCATTATGCA|AAGATGTCAC|CAACAGACTT|CTGACTGCAT|GGTGAACTTT|CATATGATAC|180|
|ATAGGATTAC|ACTTGTACCT|GTTAAAAATA|AAGTTTGAC|TTGCATAC||228|

( 2 ) INFORMATION FOR SEQ ID NO: 4:

( i ) SEQUENCE CHARACTERISTICS:
  ( A ) LENGTH: 1365 base pairs
  ( B ) TYPE: nucleic acid
  ( C ) STRANDEDNESS: single
  ( D ) TOPOLOGY: linear ( i i ) MOLECULE TYPE: genomic DNA ( x i ) SEQUENCE DESCRIPTION: SEQ ID NO: 4:

| | | | | | |
|---|---|---|---|---|---|
|ACCACAGGAG|AATGAAAAGA|ACCCGGGACT|CCCAAAGACG|CTAGATGTGT|50|
|GAAGATCCTG|ATCACTCATT|GGGTGTCTGA|GTTCTGCGAT|ATTCATCCCT|100|
|CAGCCAATGA|GCTTACTGTT|CTCGTGGGGG|GTTTGTGAGC|CTTGGGTAGG|150|
|AAGTTTTGCA|AGTTCCGCCT|ACAGCTCTAG|CTTGTGAATT|TGTACCCTTT|200|
|CACGTAAAAA|AGTAGTCCAG|AGTTTACTAC|ACCCTCCCTC|CCCCCTCCCA|250|
|CCTCGTGCTG|TGCTGAGTTT|AGAAGTCTTC|CTTATAGAAG|TCTTCCGTAT|300|
|AGAACTCTTC|CGGAGGAAGG|AGGGAGGACC|CCCCCCCTTT|GCTCTCCCAG|350|
|CATGCATTGT|GTCAACGCCA|TTGCACTGAG|CTGGTCGAAG|AAGTAAGCCG|400|
|CTAGCTTGCG|ACTCTACTCT|TATCTTAACT|TAGCTCGGCT|TCCTGCTGGT|450|
|ACCCTTTGTG|CC| | | |462|

| | |
|---|---|
| ATG TCT GAT AAC AAG AAA CCA GAC AAA GCC CAC AGT GGC TCA | 504 |
| GGT GGT GAC GGT GAT GGG AAT AGG TGC AAT TTA TTG CAC CGG | 546 |
| TAC TCC CTG GAA GAA ATT CTG CCT TAT CTA GGG TGG CTG GTC | 588 |
| TTC GCT GTT GTC ACA ACA AGT TTT CTG GCG CTC CAG ATG TTC | 630 |
| ATA GAC GCC CTT TAT GAG GAG CAG TAT GAA AGG GAT GTG GCC | 672 |
| TGG ATA GCC AGG CAA AGC AAG CGC ATG TCC TCT GTC GAT GAG | 714 |
| GAT GAA GAC GAT GAG GAT GAT GAG GAT GAC TAC TAC GAC GAC | 756 |
| GAG GAC GAC GAC GAC GAT GCC TTC TAT GAT GAT GAG GAT GAT | 798 |
| GAG GAA GAA GAA TTG GAG AAC CTG ATG GAT GAT GAA TCA GAA | 840 |
| GAT GAG GCC GAA GAA GAG ATG AGC GTG GAA ATG GGT GCC GGA | 882 |
| GCT GAG GAA ATG GGT GCT GGC GCT AAC TGT GCC TGT GTT CCT | 924 |
| GGC CAT CAT TTA AGG AAG AAT GAA GTG AAG TGT AGG ATG ATT | 966 |
| TAT TTC TTC CAC GAC CCT AAT TTC CTG GTG TCT ATA CCA GTG | 1008 |
| AAC CCT AAG GAA CAA ATG GAG TGT AGG TGT GAA AAT GCT GAT | 1050 |
| GAA GAG GTT GCA ATG GAA GAG GAA GAA GAA GAA GAG GAG GAG | 1092 |
| GAG GAG GAA GAG GAA ATG GGA AAC CCG GAT GGC TTC TCA CCT | 1134 |
| TAG | 1137 |
| GCATGCAGTT GCAAAGCCCA GAAGAAAGAA ATGGACAGCG GAAGAAGTGG | 1187 |
| TTGTTTTTTT TTCCCCTTCA TTAATTTTCT AGTTTTAGT AATCCAGAAA | 1237 |
| ATTTGATTTT GTTCTAAAGT TCATTATGCA AAGATGTCAC CAACAGACTT | 1287 |
| CTGACTGCAT GGTGAACTTT CATATGATAC ATAGGATTAC ACTTGTACCT | 1337 |
| GTTAAAAATA AAGTTTGAC TTGCATAC | 1365 |

( 2 ) INFORMATION FOR SEQ ID NO: 5:

( i ) SEQUENCE CHARACTERISTICS:
        ( A ) LENGTH: 4698 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 5:

| | |
|---|---|
| ACCACAGGAG AATGAAAAGA ACCCGGGACT CCCAAGACG CTAGATGTGT | 50 |
| GAAGATCCTG ATCACTCATT GGGTGTCTGA GTTCTGCGAT ATTCATCCCT | 100 |
| CAGCCAATGA GCTTACTGTT CTCGTGGGGG GTTTGTGAGC CTTGGGTAGG | 150 |
| AAGTTTTGCA AGTTCCGCCT ACAGCTCTAG CTTGTGAATT TGTACCCTTT | 200 |
| CACGTAAAAA AGTAGTCCAG AGTTACTAC ACCCTCCCTC CCCCCTCCCA | 250 |
| CCTCGTGCTG TGCTGAGTTT AGAAGTCTTC CTTATAGAAG TCTTCCGTAT | 300 |
| AGAACTCTTC CGGAGGAAGG AGGGAGGACC CCCCCCCTTT GCTCTCCCAG | 350 |
| CATGCATTGT GTCAACGCCA TTGCACTGAG CTGGTCGAAG AAGTAAGCCG | 400 |
| CTAGCTTGCG ACTCTACTCT TATCTTAACT TAGCTCGGCT TCCTGCTGGT | 450 |
| ACCCTTTGTG CC | 462 |
| ATG TCT GAT AAC AAG AAA CCA GAC AAA GCC CAC AGT GGC TCA | 504 |

-continued

```
GGT GGT GAC GGT GAT GGG AAT AGG TGC AAT TTA TTG CAC CGG       546
TAC TCC CTG GAA GAA ATT CTG CCT TAT CTA GGG TGG CTG GTC       588
TTC GCT GTT GTC ACA ACA AGT TTT CTG GCG CTC CAG ATG TTC       630
ATA GAC GCC CTT TAT GAG GAG CAG TAT GAA AGG GAT GTG GCC       672
TGG ATA GCC AGG CAA AGC AAG CGC ATG TCC TCT GTC GAT GAG       714
GAT GAA GAC GAT GAG GAT GAT GAG GAT GAC TAC TAC GAC GAC       756
GAG GAC GAC GAC GAC GAT GCC TTC TAT GAT GAT GAG GAT GAT       798
GAG GAA GAA GAA TTG GAG AAC CTG ATG GAT GAT GAA TCA GAA       840
GAT GAG GCC GAA GAA GAG ATG AGC GTG AAA ATG GGT GCC GGA       882
GCT GAG GAA ATG GGT GCT GGC GCT AAC TGT GCC T                 916
GTGAGTAACC CGTGGTCTTT ACTCTAGATT CAGGTGGGGT GCATTCTTTA         966
CTCTTGCCCA CATCTGTAGT AAAGACCACA TTTTGGTTGG GGGTCATTGC        1016
TGGAGCCATT CCTGGCTCTC CTGTCCACGC CTATCCCCGC TCCTCCCATC        1066
CCCCACTCCT TGCTCCGCTC TCTTTCCTTT TCCACCTTG CCTCTGGAGC         1116
TTCAGTCCAT CCTGCTCTGC TCCCTTTCCC CTTTGCTCTC CTTGCTCCCC        1166
TCCCCCTCGG CTCAACTTTT CGTGCCTTCT GCTCTCTGAT CCCCACCCTC        1216
TTCAGGCTTC CCCATTTGCT CCTCTCCCGA AACCCTCCCC TTCCTGTTCC        1266
CCTTTTCGCG CCTTTTCTTT CCTGCTCCCC TCCCCCTCCC TATTTACCTT        1316
TCACCAGCTT TGCTCTCCCT GCTCCCCTCC CCCTTTTGCA CCTTTTCTTT        1366
TCCTGCTCCC CTCCCCCTCC CCTCCCTGTT TACCCTTCAC CGCTTTTCCT        1416
CTACCTGCTT CCCTCCCCCT TGCTGCTCCC TCCCTATTTG CATTTTCGGG        1466
TGCTCCTCCC TCCCCCTCCC CCTCCCTCCC TATTTGCATT TTCGGGTGCT        1516
CCTCCCTCCC CCTCCCCAGG CCTTTTTTTT TTTTTTTTT TTTTTTTTT          1566
TTGGTTTTTC GAGACAGGGT TTCTCTTTGT ATCCCTGGCT GTCCTGGCAC        1616
TCACTCTGTA GACCAGGCTG GCCTCAAACT CAGAAATCTG CCTGCCTCTG        1666
CCTCCCAAAT GCTGGGATTA AAGGCTTGCA CCAGGACTGC CCCAGTGCAG        1716
GCCTTTCTTT TTTCTCCTCT CTGGTCTCCC TAATCCCTTT CTGCATGTT         1766
AACTCCCCTT TTGGCACCTT TCCTTTACAG GACCCCCTCC CCCTCCCTGT        1816
TTCCCTTCCG GCACCCTTCC TAGCCCTGCT CTGTTCCCTC TCCCTGCTCC        1866
CCTCCCCCTC TTTGCTCGAC TTTTAGCAGC CTTACCTCTC CCTGCTTTCT        1916
GCCCCGTTCC CCTTTTTTGT GCCTTTCCTC CTGGCTCCCC TCCACCTTCC        1966
AGCTCACCTT TTTGTTTGTT TGGTTGTTTG GTTGTTGGT TGCTTTTTT          2016
TTTTTTTTTT GCACCTTGTT TTCCAAGATC CCCTCCCCC TCCGGCTTCC         2066
CCTCTGTGTG CCTTTCCTGT TCCCTCCCCC TCGCTGGCTC CCCCTCCCTT        2116
TCTGCCTTTC CTGTCCCTGC TCCCTTCTCT GCTAACCTTT TAATGCCTTT        2166
CTTTTCTAGA CTCCCCCCTC CAGGCTTGCT GTTTGCTTCT GTGCACTTTT        2216
CCTGACCCTG CTCCCCTTCC CCTCCCAGCT CCCCCCTCTT TTCCCACCTC        2266
CCTTTCTCCA GCCTGTCACC CCTCCTTCTC TCCTCTCTGT TTCTCCCACT        2316
TCCTGCTTCC TTTACCCCTT CCCTCTCCCT ACTCTCCTCC CTGCCTGCTG        2366
GACTTCCTCT CCAGCCGCCC AGTTCCCTGC AGTCCTGGAG TCTTTCCTGC        2416
```

| | | | | |
|---|---|---|---|---|
| CTCTCTGTCC | ATCACTTCCC | CCTAGTTTCA | CTTCCCTTTC | ACTCTCCCCT | 2466
| ATGTGTCTCT | CTTCCTATCT | ATCCCTTCCT | TTCTGTCCCC | TCTCCTCTGT | 2516
| CCATCACCTC | TCTCCTCCCT | TCCCTTTCCT | CTCTCTTCCA | TTTTCTTCCA | 2566
| CCTGCTTCTT | TACCCTGCCT | CTCCCATTGC | CCTCTTACCT | TTATGCCCAT | 2616
| TCCATGTCCC | CTCTCAATTC | CCTGTCCCAT | TGTGCTCCCT | CACATCTTCC | 2666
| ATTTCCCTCT | TTCTCCCTTA | GCCTCTTCTT | CCTCTTCTCT | TGTATCTCCC | 2716
| TTCCCTTTGC | TTCTCCCTCC | TCCTTTCCCC | TTCCCTATG  | CCCTCTACTC | 2766
| TACTTGATCT | TCTCTCCTCT | CCACATACCC | TTTTTCCTTT | CCACCCTGCC | 2816
| CTTTGTCCCC | AGACCCTACA | GTATCCTGTG | CACAGGAAGT | GGGAGGTGCC | 2866
| ATCAACAACA | AGGAGGCAAG | AAACAGAGCA | AAATCCCAAA | ATCAGCAGGA | 2916
| AAGGCTGGAT | GAAAATAAGG | CCAGGTTCTG | AGGACAGCTG | GAATCTAGCC | 2966
| AAGTGGCTCC | TATAACCCTA | AGTACCAAGG | GAGAAAGTGA | TGGTGAAGTT | 3016
| CTTGATCCTT | GCTGCTTCTT | TTACATATGT | TGGCACATCT | TTCTCAAATG | 3066
| CAGGCCATGC | TCCATGCTTG | GCGCTTGCTC | AGCGTGGTTA | AGTAATGGGA | 3116
| GAATCTGAAA | ACTAGGGGCC | AGTGGTTTGT | TTTGGGGACA | AATTAGCACG | 3166
| TAGTGATATT | TCCCCCTAAA | AATTATAACA | AACAGATTCA | TGATTTGAGA | 3216
| TCCTTCTACA | GGTGAGAAGT | GGAAAAATTG | TCACTATGAA | GTTCTTTTA  | 3266
| GGCTAAAGAT | ACTTGGAACC | ATAGAAGCGT | TGTTAAAATA | CTGCTTTCTT | 3316
| TTGCTAAAAT | ATTCTTTCTC | ACATATTCAT | ATTCTCCAG  |            | 3355

| | | | | | | | | | | | | | |
|---|---|---|---|---|---|---|---|---|---|---|---|---|---|
| GT | GTT | CCT | GGC | CAT | CAT | TTA | AGG | AAG | AAT | GAA | GTG | AAG | TGT | 3396
| AGG | ATG | ATT | TAT | TTC | TTC | CAC | GAC | CCT | AAT | TTC | CTG | GTG | TCT | 3438
| ATA | CCA | GTG | AAC | CCT | AAG | GAA | CAA | ATG | GAG | TGT | AGG | TGT | GAA | 3480
| AAT | GCT | GAT | GAA | GAG | GTT | GCA | ATG | GAA | GAG | GAA | GAA | GAA | GAA | 3522
| GAG | GAG | GAG | GAG | GAG | GAA | GAG | GAA | ATG | GGA | AAC | CCG | GAT | GGC | 3564
| TTC | TCA | CCT | TAG | | | | | | | | | | | 3576

| | | | | |
|---|---|---|---|---|
| GCATGCAGGT | ACTGGCTTCA | CTAACCAACC | ATTCCTAACA | TATGCCTGTA | 3626
| GCTAAGAGCA | TCTTTTTAAA | AAATATTATT | GGTAAACTAA | ACAATTGTTA | 3676
| TCTTTTTACA | TTAATAAGTA | TTAAATTAAT | CCAGTATACA | GTTTAAGAA  | 3726
| CCCTAAGTTA | AACAGAAGTC | AATGATGTCT | AGATGCCTGT | TCTTTAGATT | 3776
| GTAGTGAGAC | TACTTACTAC | AGATGAGAAG | TTGTTAGACT | CGGGAGTAGA | 3826
| GACCAGTAAA | AGATCATGCA | GTGAAATGTG | GCCATGGAAA | TCGCATATTG | 3876
| TTCTTATAGT | ACCTTTGAGA | CAGCTGATAA | CAGCTGACAA | AAATAAGTGT | 3926
| TTCAAGAAAG | ATCACACGCC | ATGGTTCACA | TGCAAATTAT | TATTTGTCG  | 3976
| TTCTGATTTT | TTTCATTTCT | AGACCTGTGG | TTTTAAAGAG | ATGAAAATCT | 4026
| CTTAAAATTT | CCTTCATCTT | TAATTTTCCT | TAACTTAGT  | TTTTTTCACT | 4076
| TAGAATTCAA | TTCAAATTCT | TAATTCAATC | TTAATTTTA  | GATTTCTTAA | 4126
| AATGTTTTTT | AAAAAAAATG | CAAATCTCAT | TTTTAAGAGA | TGAAAGCAGA | 4176
| GTAACTGGGG | GGCTTAGGGA | ATCTGTAGGG | TTGCGGTATA | GCAATAGGGA | 4226
| GTTCTGGTCT | CTGAGAAGCA | GTCAGAGAGA | ATGGAAAACC | AGGCCCTTGC | 4276
| CAGTAGGTTA | GTGAGGTTGA | TATGATCAGA | TTATGGACAC | TCTCCAAATC | 4326

| | | | | | |
|---|---|---|---|---|---|
| ATAAATACTC | TAACAGCTAA | GGATCTCTGA | GGGAAACACA | ACAGGGAAAT | 4376 |
| ATTTTAGTTT | CTCCTTGAGA | AACAATGACA | AGACATAAAA | TTGGCAAGAA | 4426 |
| AGTCAGGAGT | GTATTCTAAT | AAGTGTTGCT | TATCTCTTAT | TTTCTTCTAC | 4476 |
| AGTTGCAAAG | CCCAGAAGAA | AGAAATGGAC | AGCGGAAGAA | GTGGTTGTTT | 4526 |
| TTTTTTCCCC | TTCATTAATT | TTCTAGTTTT | TAGTAATCCA | GAAAATTTGA | 4576 |
| TTTTGTTCTA | AAGTTCATTA | TGCAAAGATG | TCACCAACAG | ACTTCTGACT | 4626 |
| GCATGGTGAA | CTTTCATATG | ATACATAGGA | TTACACTTGT | ACCTGTTAAA | 4676 |
| AATAAAAGTT | TGACTTGCAT | AC | | | 4698 |

(2) INFORMATION FOR SEQ ID NO: 6:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO: 6:

Leu Pro Tyr Leu Gly Trp Leu Val Phe
                5

(2) INFORMATION FOR SEQ ID NO: 7:

(i) SEQUENCE CHARACTERISTICS:
        (A) LENGTH: 2419 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 7:

| | | | | | |
|---|---|---|---|---|---|
| GGATCCAGGC | CCTGCCAGGA | AAAATATAAG | GGCCCTGCGT | GAGAACAGAG | 50 |
| GGGGTCATCC | ACTGCATGAG | AGTGGGGATG | TCACAGAGTC | CAGCCCACCC | 100 |
| TCCTGGTAGC | ACTGAGAAGC | CAGGGCTGTG | CTTGCGGTCT | GCACCCTGAG | 150 |
| GGCCCGTGGA | TTCCTCTTCC | TGGAGCTCCA | GGAACCAGGC | AGTGAGGCCT | 200 |
| TGGTCTGAGA | CAGTATCCTC | AGGTCACAGA | GCAGAGGATG | CACAGGGTGT | 250 |
| GCCAGCAGTG | AATGTTTGCC | CTGAATGCAC | ACCAAGGGCC | CCACCTGCCA | 300 |
| CAGGACACAT | AGGACTCCAC | AGAGTCTGGC | CTCACCTCCC | TACTGTCAGT | 350 |
| CCTGTAGAAT | CGACCTCTGC | TGGCCGGCTG | TACCCTGAGT | ACCCTCTCAC | 400 |
| TTCCTCCTTC | AGGTTTTCAG | GGGACAGGCC | AACCCAGAGG | ACAGGATTCC | 450 |
| CTGGAGGCCA | CAGAGGAGCA | CCAAGGAGAA | GATCTGTAAG | TAGGCCTTTG | 500 |
| TTAGAGTCTC | CAAGGTTCAG | TTCTCAGCTG | AGGCCTCTCA | CACACTCCCT | 550 |
| CTCTCCCCAG | GCCTGTGGGT | CTTCATTGCC | CAGCTCCTGC | CCACACTCCT | 600 |
| GCCTGCTGCC | CTGACGAGAG | TCATCATGTC | TCTTGAGCAG | AGGAGTCTGC | 650 |
| ACTGCAAGCC | TGAGGAAGCC | CTTGAGGCCC | AACAAGAGGC | CCTGGGCCTG | 700 |
| GTGTGTGTGC | AGGCTGCCAC | CTCCTCCTCC | TCTCCTCTGG | TCCTGGGCAC | 750 |
| CCTGGAGGAG | GTGCCCACTG | CTGGGTCAAC | AGATCCTCCC | CAGAGTCCTC | 800 |
| AGGGAGCCTC | CGCCTTTCCC | ACTACCATCA | ACTTCACTCG | ACAGAGGCAA | 850 |
| CCCAGTGAGG | GTTCCAGCAG | CCGTGAAGAG | GAGGGGCCAA | GCACCTCTTG | 900 |

| | | | | |
|---|---|---|---|---|
| TATCCTGGAG | TCCTTGTTCC | GAGCAGTAAT | CACTAAGAAG | GTGGCTGATT | 950 |
| TGGTTGGTTT | TCTGCTCCTC | AAATATCGAG | CCAGGGAGCC | AGTCACAAAG | 1000 |
| GCAGAAATGC | TGGAGAGTGT | CATCAAAAAT | TACAAGCACT | GTTTTCCTGA | 1050 |
| GATCTTCGGC | AAAGCCTCTG | AGTCCTTGCA | GCTGGTCTTT | GGCATTGACG | 1100 |
| TGAAGGAAGC | AGACCCCACC | GGCCACTCCT | ATGTCCTTGT | CACCTGCCTA | 1150 |
| GGTCTCTCCT | ATGATGGCCT | GCTGGGTGAT | AATCAGATCA | TGCCCAAGAC | 1200 |
| AGGCTTCCTG | ATAATTGTCC | TGGTCATGAT | TGCAATGGAG | GGCGGCCATG | 1250 |
| CTCCTGAGGA | GGAAATCTGG | GAGGAGCTGA | GTGTGATGGA | GGTGTATGAT | 1300 |
| GGGAGGGAGC | ACAGTGCCTA | TGGGGAGCCC | AGGAAGCTGC | TCACCCAAGA | 1350 |
| TTTGGTGCAG | GAAAAGTACC | TGGAGTACGG | CAGGTGCCGG | ACAGTGATCC | 1400 |
| CGCACGCTAT | GAGTTCCTGT | GGGGTCCAAG | GGCCCTCGCT | GAAACCAGCT | 1450 |
| ATGTGAAAGT | CCTTGAGTAT | GTGATCAAGG | TCAGTGCAAG | AGTTCGCTTT | 1500 |
| TTCTTCCCAT | CCCTGCGTGA | AGCAGCTTTG | AGAGGAGG | AAGAGGGAGT | 1550 |
| CTGAGCATGA | GTTGCAGCCA | AGGCCAGTGG | GAGGGGACT | GGGCCAGTGC | 1600 |
| ACCTTCCAGG | GCCGCGTCCA | GCAGCTTCCC | CTGCCTCGTG | TGACATGAGG | 1650 |
| CCCATTCTTC | ACTCTGAAGA | GAGCGGTCAG | TGTTCTCAGT | AGTAGGTTTC | 1700 |
| TGTTCTATTG | GGTGACTTGG | AGATTTATCT | TTGTTCTCTT | TTGGAATTGT | 1750 |
| TCAAATGTTT | TTTTTAAGG | GATGGTTGAA | TGAACTTCAG | CATCCAAGTT | 1800 |
| TATGAATGAC | AGCAGTCACA | CAGTTCTGTG | TATATAGTTT | AAGGGTAAGA | 1850 |
| GTCTTGTGTT | TTATTCAGAT | TGGGAAATCC | ATTCTATTTT | GTGAATTGGG | 1900 |
| ATAATAACAG | CAGTGGAATA | AGTACTTAGA | AATGTGAAAA | ATGAGCAGTA | 1950 |
| AAATAGATGA | GATAAAGAAC | TAAAGAAATT | AAGAGATAGT | CAATTCTTGC | 2000 |
| CTTATACCTC | AGTCTATTCT | GTAAAATTTT | TAAAGATATA | TGCATACCTG | 2050 |
| GATTTCCTTG | GCTTCTTTGA | GAATGTAAGA | GAAATTAAAT | CTGAATAAAG | 2100 |
| AATTCTTCCT | GTTCACTGGC | TCTTTTCTTC | TCCATGCACT | GAGCATCTGC | 2150 |
| TTTTTGGAAG | GCCCTGGGTT | AGTAGTGGAG | ATGCTAAGGT | AAGCCAGACT | 2200 |
| CATACCCACC | CATAGGGTCG | TAGAGTCTAG | GAGCTGCAGT | CACGTAATCG | 2250 |
| AGGTGGCAAG | ATGTCCTCTA | AAGATGTAGG | GAAAAGTGAG | AGAGGGGTGA | 2300 |
| GGGTGTGGGG | CTCCGGGTGA | GAGTGGTGGA | GTGTCAATGC | CCTGAGCTGG | 2350 |
| GGCATTTTGG | GCTTTGGGAA | ACTGCAGTTC | CTTCTGGGGG | AGCTGATTGT | 2400 |
| AATGATCTTG | GGTGGATCC | | | | 2419 |

( 2 ) INFORMATION FOR SEQ ID NO: 8:

( i ) SEQUENCE CHARACTERISTICS:
        ( A ) LENGTH: 5674 base pairs
        ( B ) TYPE: nucleic acid
        ( C ) STRANDEDNESS: single
        ( D ) TOPOLOGY: linear ( i i ) MOLECULE TYPE: genomic DNA ( i x ) FEATURE:
        ( A ) NAME/KEY: MAGE-1 gene ( x i ) SEQUENCE DESCRIPTION: SEQ ID NO: 8:

| | | | | |
|---|---|---|---|---|
| CCCGGGGCAC | CACTGGCATC | CCTCCCCCTA | CCACCCCCAA | TCCCTCCCTT | 50 |

| | | | | |
|---|---|---|---|---|
| TACGCCACCC | ATCCAAACAT | CTTCACGCTC | ACCCCCAGCC | CAAGCCAGGC | 100 |
| AGAATCCGGT | TCCACCCCTG | CTCTCAACCC | AGGGAAGCCC | AGGTGCCCAG | 150 |
| ATGTGACGCC | ACTGACTTGA | GCATTAGTGG | TTAGAGAGAA | GCGAGGTTTT | 200 |
| CGGTCTGAGG | GGCGGCTTGA | GATCGGTGGA | GGGAAGCGGG | CCCAGCTCTG | 250 |
| TAAGGAGGCA | AGGTGACATG | CTGAGGGAGG | ACTGAGGACC | CACTTACCCC | 300 |
| AGATAGAGGA | CCCCAAATAA | TCCCTTCATG | CCAGTCCTGG | ACCATCTGGT | 350 |
| GGTGGACTTC | TCAGGCTGGG | CCACCCCCAG | CCCCCTTGCT | GCTTAAACCA | 400 |
| CTGGGACTC | GAAGTCAGAG | CTCCGTGTGA | TCAGGGAAGG | GCTGCTTAGG | 450 |
| AGAGGGCAGC | GTCCAGGCTC | TGCCAGACAT | CATGCTCAGG | ATTCTCAAGG | 500 |
| AGGGCTGAGG | GTCCCTAAGA | CCCCACTCCC | GTGACCCAAC | CCCCACTCCA | 550 |
| ATGCTCACTC | CCGTGACCCA | ACCCCTCTT | CATTGTCATT | CCAACCCCCA | 600 |
| CCCCACATCC | CCCACCCCAT | CCCTCAACCC | TGATGCCCAT | CCGCCCAGCC | 650 |
| ATTCCACCCT | CACCCCCACC | CCCACCCCCA | CGCCCACTCC | CACCCCCACC | 700 |
| CAGGCAGGAT | CCGGTTCCCG | CCAGGAAACA | TCCGGGTGCC | CGGATGTGAC | 750 |
| GCCACTGACT | TGCGCATTGT | GGGGCAGAGA | GAAGCGAGGT | TTCCATTCTG | 800 |
| AGGGACGGCG | TAGAGTTCGG | CCGAAGGAAC | CTGACCCAGG | CTCTGTGAGG | 850 |
| AGGCAAGGTG | AGAGGCTGAG | GGAGGACTGA | GGACCCCGCC | ACTCCAAATA | 900 |
| GAGAGCCCCA | AATATTCCAG | CCCCGCCCTT | GCTGCCAGCC | CTGGCCCACC | 950 |
| CGCGGGAAGA | CGTCTCAGCC | TGGGCTGCCC | CCAGACCCCT | GCTCCAAAAG | 1000 |
| CCTTGAGAGA | CACCAGGTTC | TTCTCCCCAA | GCTCTGGAAT | CAGAGGTTGC | 1050 |
| TGTGACCAGG | GCAGGACTGG | TTAGGAGAGG | GCAGGGCACA | GGCTCTGCCA | 1100 |
| GGCATCAAGA | TCAGCACCCA | AGAGGGAGGG | CTGTGGGCCC | CCAAGACTGC | 1150 |
| ACTCCAATCC | CCACTCCCAC | CCCATTCGCA | TTCCCATTCC | CCACCCAACC | 1200 |
| CCCATCTCCT | CAGCTACACC | TCCACCCCCA | TCCCTACTCC | TACTCCGTCA | 1250 |
| CCTGACCACC | ACCCTCCAGC | CCCAGCACCA | GCCCAACCC | TTCTGCCACC | 1300 |
| TCACCCTCAC | TGCCCCCAAC | CCCACCCTCA | TCTCTCTCAT | GTGCCCCACT | 1350 |
| CCCATCGCCT | CCCCCATTCT | GGCAGAATCC | GGTTTGCCCC | TGCTCTCAAC | 1400 |
| CCAGGGAAGC | CCTGGTAGGC | CCGATGTGAA | ACCACTGACT | TGAACCTCAC | 1450 |
| AGATCTGAGA | GAAGCCAGGT | TCATTTAATG | GTTCTGAGGG | GCGGCTTGAG | 1500 |
| ATCCACTGAG | GGGAGTGGTT | TTAGGCTCTG | TGAGGAGGCA | AGGTGAGATG | 1550 |
| CTGAGGGAGG | ACTGAGGAGG | CACACACCCC | AGGTAGATGG | CCCCAAAATG | 1600 |
| ATCCAGTACC | ACCCCTGCTG | CCAGCCCTGG | ACCACCGGC | CAGGACAGAT | 1650 |
| GTCTCAGCTG | GACCACCCCC | CGTCCCGTCC | CACTGCCACT | TAACCCACAG | 1700 |
| GGCAATCTGT | AGTCATAGCT | TATGTGACCG | GGGCAGGGTT | GGTCAGGAGA | 1750 |
| GGCAGGGCCC | AGGCATCAAG | GTCCAGCATC | CGCCCGGCAT | TAGGGTCAGG | 1800 |
| ACCCTGGGAG | GGAACTGAGG | GTTCCCCACC | CACACCTGTC | TCCTCATCTC | 1850 |
| CACCGCCACC | CCACTCACAT | TCCCATACCT | ACCCCTACC | CCCAACCTCA | 1900 |
| TCTTGTCAGA | ATCCCTGCTG | TCAACCCACG | GAAGCCACGG | GAATGGCGGC | 1950 |
| CAGGCACTCG | GATCTTGACG | TCCCCATCCA | GGGTCTGATG | GAGGGAAGGG | 2000 |
| GCTTGAACAG | GGCCTCAGGG | GAGCAGAGGG | AGGGCCCTAC | TGCGAGATGA | 2050 |

```
GGGAGGCCTC AGAGGACCCA GCACCCTAGG ACACCGCACC CCTGTCTGAG          2100
ACTGAGGCTG CCACTTCTGG CCTCAAGAAT CAGAACGATG GGGACTCAGA          2150
TTGCATGGGG GTGGGACCCA GGCCTGCAAG GCTTACGCGG AGGAAGAGGA          2200
GGGAGGACTC AGGGGACCTT GGAATCCAGA TCAGTGTGGA CCTCGGCCCT          2250
GAGAGGTCCA GGGCACGGTG GCCACATATG GCCCATATTT CCTGCATCTT          2300
TGAGGTGACA GGACAGAGCT GTGGTCTGAG AAGTGGGGCC TCAGGTCAAC          2350
AGAGGGAGGA GTTCCAGGAT CCATATGGCC CAAGATGTGC CCCCTTCATG          2400
AGGACTGGGG ATATCCCCGG CTCAGAAAGA AGGGACTCCA CACAGTCTGG          2450
CTGTCCCCTT TTAGTAGCTC TAGGGGGACC AGATCAGGGA TGGCGGTATG          2500
TTCCATTCTC ACTTGTACCA CAGGCAGGAA GTTGGGGGGC CCTCAGGGAG          2550
ATGGGGTCTT GGGGTAAAGG GGGGATGTCT ACTCATGTCA GGGAATTGGG          2600
GGTTGAGGAA GCACAGGCGC TGGCAGGAAT AAAGATGAGT GAGACAGACA          2650
AGGCTATTGG AATCCACACC CCAGAACCAA AGGGGTCAGC CCTGGACACC          2700
TCACCCAGGA TGTGGCTTCT TTTTCACTCC TGTTTCCAGA TCTGGGGCAG          2750
GTGAGGACCT CATTCTCAGA GGGTGACTCA GGTCAACGTA GGGACCCCCA          2800
TCTGGTCTAA AGACAGAGCG GTCCCAGGAT CTGCCATGCG TTCGGGTGAG          2850
GAACATGAGG GAGGACTGAG GGTACCCCAG GACCAGAACA CTGAGGGAGA          2900
CTGCACAGAA ATCAGCCCTG CCCCTGCTGT CACCCCAGAG AGCATGGGCT          2950
GGGCCGTCTG CCGAGGTCCT TCCGTTATCC TGGGATCATT GATGTCAGGG          3000
ACGGGGAGGC CTTGGTCTGA GAAGGCTGCG CTCAGGTCAG TAGAGGGAGC          3050
GTCCCAGGCC CTGCCAGGAG TCAAGGTGAG GACCAAGCGG GCACCTCACC          3100
CAGGACACAT TAATTCCAAT GAATTTGAT  ATCTCTTGCT GCCCTTCCCC          3150
AAGGACCTAG GCACGTGTGG CCAGATGTTT GTCCCTCCT  GTCCTTCCAT          3200
TCCTTATCAT GGATGTGAAC TCTTGATTTG GATTTCTCAG ACCAGCAAAA          3250
GGGCAGGATC CAGGCCCTGC CAGGAAAAAT ATAAGGGCCC TGCGTGAGAA          3300
CAGAGGGGGT CATCCACTGC ATGAGAGTGG GGATGTCACA GAGTCCAGCC          3350
CACCCTCCTG GTAGCACTGA GAAGCCAGGG CTGTGCTTGC GGTCTGCACC          3400
CTGAGGGCCC GTGGATTCCT CTTCCTGGAG CTCCAGGAAC CAGGCAGTGA          3450
GGCCTTGGTC TGAGACAGTA TCCTCAGGTC ACAGAGCAGA GGATGCACAG          3500
GGTGTGCCAG CAGTGAATGT TTGCCCTGAA TGCACACCAA GGGCCCCACC          3550
TGCCACAGGA CACATAGGAC TCCACAGAGT CTGGCCTCAC CTCCCTACTG          3600
TCAGTCCTGT AGAATCGACC TCTGCTGGCC GGCTGTACCC TGAGTACCCT          3650
CTCACTTCCT CCTTCAGGTT TTCAGGGAC  AGGCCAACCC AGAGGACAGG          3700
ATTCCCTGGA GGCCACAGAG GAGCACCAAG GAGAAGATCT GTAAGTAGGC          3750
CTTTGTTAGA GTCTCCAAGG TTCAGTTCTC AGCTGAGGCC TCTCACACAC          3800
TCCCTCTCTC CCCAGGCCTG TGGGTCTTCA TTGCCCAGCT CCTGCCCACA          3850
CTCCTGCCTG CTGCCCTGAC GAGAGTCATC                               3880
ATG TCT CTT GAG CAG AGG AGT CTG CAC TGC AAG CCT GAG GAA        3922
GCC CTT GAG GCC CAA CAA GAG GCC CTG GGC CTG GTG TGT GTG        3964
CAG GCT GCC ACC TCC TCC TCC TCT CCT CTG GTC CTG GGC ACC        4006
```

| | | | | | | | | | | | | | |
|---|---|---|---|---|---|---|---|---|---|---|---|---|---|
| CTG | GAG | GAG | GTG | CCC | ACT | GCT | GGG | TCA | ACA | GAT | CCT | CCC | CAG | 4048 |
| AGT | CCT | CAG | GGA | GCC | TCC | GCC | TTT | CCC | ACT | ACC | ATC | AAC | TTC | 4090 |
| ACT | CGA | CAG | AGG | CAA | CCC | AGT | GAG | GGT | TCC | AGC | AGC | CGT | GAA | 4132 |
| GAG | GAG | GGG | CCA | AGC | ACC | TCT | TGT | ATC | CTG | GAG | TCC | TTG | TTC | 4174 |
| CGA | GCA | GTA | ATC | ACT | AAG | AAG | GTG | GCT | GAT | TTG | GTT | GGT | TTT | 4216 |
| CTG | CTC | CTC | AAA | TAT | CGA | GCC | AGG | GAG | CCA | GTC | ACA | AAG | GCA | 4258 |
| GAA | ATG | CTG | GAG | AGT | GTC | ATC | AAA | AAT | TAC | AAG | CAC | TGT | TTT | 4300 |
| CCT | GAG | ATC | TTC | GGC | AAA | GCC | TCT | GAG | TCC | TTG | CAG | CTG | GTC | 4342 |
| TTT | GGC | ATT | GAC | GTG | AAG | GAA | GCA | GAC | CCC | ACC | GGC | CAC | TCC | 4384 |
| TAT | GTC | CTT | GTC | ACC | TGC | CTA | GGT | CTC | TCC | TAT | GAT | GGC | CTG | 4426 |
| CTG | GGT | GAT | AAT | CAG | ATC | ATG | CCC | AAG | ACA | GGC | TTC | CTG | ATA | 4468 |
| ATT | GTC | CTG | GTC | ATG | ATT | GCA | ATG | GAG | GGC | GGC | CAT | GCT | CCT | 4510 |
| GAG | GAG | GAA | ATC | TGG | GAG | GAG | CTG | AGT | GTG | ATG | GAG | GTG | TAT | 4552 |
| GAT | GGG | AGG | GAG | CAC | AGT | GCC | TAT | GGG | GAG | CCC | AGG | AAG | CTG | 4594 |
| CTC | ACC | CAA | GAT | TTG | GTG | CAG | GAA | AAG | TAC | CTG | GAG | TAC | GGC | 4636 |
| AGG | TGC | CGG | ACA | GTG | ATC | CCG | CAC | GCT | ATG | AGT | TCC | TGT | GGG | 4678 |
| GTC | CAA | GGG | CCC | TCG | CTG | AAA | CCA | GCT | ATG | TGA | | | | 4711 |

| | | | | |
|---|---|---|---|---|
| AAGTCCTTGA | GTATGTGATC | AAGGTCAGTG | CAAGAGTTC | 4750 |
| GCTTTTTCTT | CCCATCCCTG | CGTGAAGCAG | CTTTGAGAGA | GGAGGAAGAG | 4800 |
| GGAGTCTGAG | CATGAGTTGC | AGCCAAGGCC | AGTGGGAGGG | GGACTGGGCC | 4850 |
| AGTGCACCTT | CCAGGGCCGC | GTCCAGCAGC | TTCCCCTGCC | TCGTGTGACA | 4900 |
| TGAGGCCCAT | TCTTCACTCT | GAAGAGAGCG | GTCAGTGTTC | TCAGTAGTAG | 4950 |
| GTTTCTGTTC | TATTGGGTGA | CTTGGAGATT | TATCTTTGTT | CTCTTTTGGA | 5000 |
| ATTGTTCAAA | TGTTTTTTTT | TAAGGGATGG | TTGAATGAAC | TTCAGCATCC | 5050 |
| AAGTTTATGA | ATGACAGCAG | TCACACAGTT | CTGTGTATAT | AGTTTAAGGG | 5100 |
| TAAGAGTCTT | GTGTTTATT | CAGATTGGGA | AATCCATTCT | ATTTTGTGAA | 5150 |
| TTGGGATAAT | AACAGCAGTG | GAATAAGTAC | TTAGAAATGT | GAAAAATGAG | 5200 |
| CAGTAAAATA | GATGAGATAA | AGAACTAAAG | AAATTAAGAG | ATAGTCAATT | 5250 |
| CTTGCCTTAT | ACCTCAGTCT | ATTCTGTAAA | ATTTTAAAG | ATATATGCAT | 5300 |
| ACCTGGATTT | CCTTGGCTTC | TTTGAGAATG | TAAGAGAAAT | TAAATCTGAA | 5350 |
| TAAAGAATTC | TTCCTGTTCA | CTGGCTCTTT | TCTTCTCCAT | GCACTGAGCA | 5400 |
| TCTGCTTTTT | GGAAGGCCCT | GGGTTAGTAG | TGGAGATGCT | AAGGTAAGCC | 5450 |
| AGACTCATAC | CCACCCATAG | GGTCGTAGAG | TCTAGGAGCT | GCAGTCACGT | 5500 |
| AATCGAGGTG | GCAAGATGTC | CTCTAAAGAT | GTAGGGAAAA | GTGAGAGAGG | 5550 |
| GGTGAGGGTG | TGGGGCTCCG | GGTGAGAGTG | GTGGAGTGTC | AATGCCCTGA | 5600 |
| GCTGGGGCAT | TTTGGGCTTT | GGGAAACTGC | AGTTCCTTCT | GGGGGAGCTG | 5650 |
| ATTGTAATGA | TCTTGGGTGG | ATCC | | | 5674 |

( 2 ) INFORMATION FOR SEQ ID NO: 9:

( i ) SEQUENCE CHARACTERISTICS:
        ( A ) LENGTH: 4157 base pairs
        ( B ) TYPE: nucleic acid ( C ) STRANDEDNESS: single
( D ) TOPOLOGY: linear ( i i ) MOLECULE TYPE: genomic DNA ( i x ) FEATURE:
( A ) NAME/KEY: MAGE-2 gene ( x i ) SEQUENCE DESCRIPTION: SEQ ID NO: 9:

| | | | | | |
|---|---|---|---|---|---|
| CCCATCCAGA | TCCCCATCCG | GGCAGAATCC | GGTTCCACCC | TTGCCGTGAA | 50 |
| CCCAGGGAAG | TCACGGGCCC | GGATGTGACG | CCACTGACTT | GCACATTGGA | 100 |
| GGTCAGAGGA | CAGCGAGATT | CTCGCCCTGA | GCAACGGCCT | GACGTCGGCG | 150 |
| GAGGGAAGCA | GGCGCAGGCT | CCGTGAGGAG | GCAAGGTAAG | ACGCCGAGGG | 200 |
| AGGACTGAGG | CGGGCCTCAC | CCCAGACAGA | GGGCCCCAA | TTAATCCAGC | 250 |
| GCTGCCTCTG | CTGCCGGGCC | TGGACCACCC | TGCAGGGGAA | GACTTCTCAG | 300 |
| GCTCAGTCGC | CACCACCTCA | CCCCGCCACC | CCCGCCGCT | TTAACCGCAG | 350 |
| GGAACTCTGG | CGTAAGAGCT | TTGTGTGACC | AGGGCAGGGC | TGGTTAGAAG | 400 |
| TGCTCAGGGC | CCAGACTCAG | CCAGGAATCA | AGGTCAGGAC | CCCAAGAGGG | 450 |
| GACTGAGGGC | AACCCACCCC | CTACCCTCAC | TACCAATCCC | ATCCCCAAC | 500 |
| ACCAACCCCA | CCCCCATCCC | TCAAACACCA | ACCCCACCCC | CAAACCCCAT | 550 |
| TCCCATCTCC | TCCCCCACCA | CCATCCTGGC | AGAATCCGGC | TTTGCCCCTG | 600 |
| CAATCAACCC | ACGGAAGCTC | CGGGAATGGC | GGCCAAGCAC | GCGGATCCTG | 650 |
| ACGTTCACAT | GTACGGCTAA | GGGAGGGAAG | GGGTTGGGTC | TCGTGAGTAT | 700 |
| GGCCTTTGGG | ATGCAGAGGA | AGGGCCCAGG | CCTCCTGGAA | GACAGTGGAG | 750 |
| TCCTTAGGGG | ACCCAGCATG | CCAGGACAGG | GGGCCCACTG | TACCCCTGTC | 800 |
| TCAAACTGAG | CCACCTTTTC | ATTCAGCCGA | GGGAATCCTA | GGGATGCAGA | 850 |
| CCCACTTCAG | GGGGTTGGGG | CCCAGCCTGC | GAGGAGTCAA | GGGGAGGAAG | 900 |
| AAGAGGGAGG | ACTGAGGGGA | CCTTGGAGTC | CAGATCAGTG | GCAACCTTGG | 950 |
| GCTGGGGGAT | CCTGGGCACA | GTGGCCGAAT | GTGCCCCGTG | CTCATTGCAC | 1000 |
| CTTCAGGGTG | ACAGAGAGTT | GAGGGCTGTG | GTCTGAGGGC | TGGGACTTCA | 1050 |
| GGTCAGCAGA | GGGAGGAATC | CCAGGATCTG | CCGGACCCAA | GGTGTGCCCC | 1100 |
| CTTCATGAGG | ACTCCCCATA | CCCCGGCCC | AGAAAGAAGG | GATGCCACAG | 1150 |
| AGTCTGGAAG | TAAATTGTTC | TTAGCTCTGG | GGGAACCTGA | TCAGGGATGG | 1200 |
| CCCTAAGTGA | CAATCTCATT | TGTACCACAG | GCAGGAGGTT | GGGGAACCCT | 1250 |
| CAGGGAGATA | AGGTGTTGGT | GTAAAGAGGA | GCTGTCTGCT | CATTTCAGGG | 1300 |
| GGTTCCCCCT | TGAGAAAGGG | CAGTCCCTGG | CAGGAGTAAA | GATGAGTAAC | 1350 |
| CCACAGGAGG | CCATCATAAC | GTTCACCCTA | GAACCAAAGG | GGTCAGCCCT | 1400 |
| GGACAACGCA | CGTGGGGTAA | CAGGATGTGG | CCCCTCCTCA | CTTGTCTTTC | 1450 |
| CAGATCTCAG | GGAGTTGATG | ACCTTGTTTT | CAGAAGGTGA | CTCAGTCAAC | 1500 |
| ACAGGGGCCC | CTCTGGTCGA | CAGATGCAGT | GGTTCTAGGA | TCTGCCAAGC | 1550 |
| ATCCAGGTGG | AGAGCCTGAG | GTAGGATTGA | GGGTACCCCT | GGGCCAGAAT | 1600 |
| GCAGCAAGGG | GGCCCCATAG | AAATCTGCCC | TGCCCCTGCG | GTTACTTCAG | 1650 |
| AGACCCTGGG | CAGGGCTGTC | AGCTGAAGTC | CCTCCATTAT | CTGGGATCTT | 1700 |
| TGATGTCAGG | GAAGGGGAGG | CCTTGGTCTG | AAGGGGCTGG | AGTCAGGTCA | 1750 |

| | | | | |
|---|---|---|---|---|
| GTAGAGGGAG | GGTCTCAGGC | CCTGCCAGGA | GTGGACGTGA | GGACCAAGCG | 1800 |
| GACTCGTCAC | CCAGGACACC | TGGACTCCAA | TGAATTTGAC | ATCTCTCGTT | 1850 |
| GTCCTTCGCG | GAGGACCTGG | TCACGTATGG | CCAGATGTGG | GTCCCTCTA | 1900 |
| TCTCCTTCTG | TACCATATCA | GGGATGTGAG | TTCTTGACAT | GAGAGATTCT | 1950 |
| CAAGCCAGCA | AAAGGGTGGG | ATTAGGCCCT | ACAAGGAGAA | AGGTGAGGGC | 2000 |
| CCTGAGTGAG | CACAGAGGGG | ACCCTCCACC | CAAGTAGAGT | GGGGACCTCA | 2050 |
| CGGAGTCTGG | CCAACCCTGC | TGAGACTTCT | GGGAATCCGT | GGCTGTGCTT | 2100 |
| GCAGTCTGCA | CACTGAAGGC | CCGTGCATTC | CTCTCCCAGG | AATCAGGAGC | 2150 |
| TCCAGGAACC | AGGCAGTGAG | GCCTTGGTCT | GAGTCAGTGC | CTCAGGTCAC | 2200 |
| AGAGCAGAGG | GGACGCAGAC | AGTGCCAACA | CTGAAGGTTT | GCCTGGAATG | 2250 |
| CACACCAAGG | GCCCCACCCG | CCCAGAACAA | ATGGGACTCC | AGAGGGCCTG | 2300 |
| GCCTCACCCT | CCCTATTCTC | AGTCCTGCAG | CCTGAGCATG | TGCTGGCCGG | 2350 |
| CTGTACCCTG | AGGTGCCCTC | CCACTTCCTC | CTTCAGGTTC | TGAGGGGAC | 2400 |
| AGGCTGACAA | GTAGGACCCG | AGGCACTGGA | GGAGCATTGA | AGGAGAAGAT | 2450 |
| CTGTAAGTAA | GCCTTTGTCA | GAGCCTCCAA | GGTTCAGTTC | AGTTCTCACC | 2500 |
| TAAGGCCTCA | CACACGCTCC | TTCTCTCCCC | AGGCCTGTGG | GTCTTCATTG | 2550 |
| CCCAGCTCCT | GCCCGCACTC | CTGCCTGCTG | CCCTGACCAG | AGTCATC | 2597 |
| ATG CCT CTT GAG CAG AGG AGT CAG CAC TGC AAG CCT GAA GAA | | | | | 2639 |
| GGC CTT GAG GCC CGA GGA GAG GCC CTG GGC CTG GTG GGT GCG | | | | | 2681 |
| CAG GCT CCT GCT ACT GAG GAG CAG CAG ACC GCT TCT TCC TCT | | | | | 2723 |
| TCT ACT CTA GTG GAA GTT ACC CTG GGG GAG GTG CCT GCT GCC | | | | | 2765 |
| GAC TCA CCG AGT CCT CCC CAC AGT CCT CAG GGA GCC TCC AGC | | | | | 2807 |
| TTC TCG ACT ACC ATC AAC TAC ACT CTT TGG AGA CAA TCC GAT | | | | | 2849 |
| GAG GGC TCC AGC AAC CAA GAA GAG GAG GGG CCA AGA ATG TTT | | | | | 2891 |
| CCC GAC CTG GAG TCC GAG TTC CAA GCA GCA ATC AGT AGG AAG | | | | | 2933 |
| ATG GTT GAG TTG GTT CAT TTT CTG CTC CTC AAG TAT CGA GCC | | | | | 2975 |
| AGG GAG CCG GTC ACA AAG GCA GAA ATG CTG GAG AGT GTC CTC | | | | | 3017 |
| AGA AAT GCC AGG ACT TCT TTT CCC GTG ATC TTC AGC AAA GCC | | | | | 3059 |
| TCC GAG TAC TTG CAG CTG GTC TTT GGC ATC GAG GTG GTG GAA | | | | | 3101 |
| GTG GTC CCC ATC AGC CAC TTG TAC ATC CTT GTC ACC TGC CTG | | | | | 3143 |
| GGC CTC TCC TAC GAT GGC CTG CTG GGC GAC AAT CAG GTC ATG | | | | | 3185 |
| CCC AAG ACA GGC CTC CTG ATA ATC GTC CTG GCC ATA ATC GCA | | | | | 3227 |
| ATA GAG GGC GAC TGT GCC CCT GAG GAG AAA ATC TGG GAG GAG | | | | | 3269 |
| CTG AGT ATG TTG GAG GTG TTT GAG GGG AGG GAG GAC AGT GTC | | | | | 3311 |
| TTC GCA CAT CCC AGG AAG CTG CTC ATG CAA GAT CTG GTG CAG | | | | | 3353 |
| GAA AAC TAC CTG GAG TAC CGG CAG GTG CCC GGC AGT GAT CCT | | | | | 3395 |
| GCA TGC TAC GAG TTC CTG TGG GGT CCA AGG GCC CTC ATT GAA | | | | | 3437 |
| ACC AGC TAT GTG AAA GTC CTG CAC CAT ACA CTA AAG ATC GGT | | | | | 3479 |
| GGA GAA CCT CAC ATT TCC TAC CCA CCC CTG CAT GAA CGG GCT | | | | | 3521 |
| TTG AGA GAG GGA GAA GAG TGA | | | | | 3542 |

|                     |            |            |            |      |
|---------------------|------------|------------|------------|------|
| GTCTCAGCAC ATGTTGCAGC | CAGGGCCAGT | GGGAGGGGGT | CTGGGCCAGT | 3592 |
| GCACCTTCCA GGGCCCCATC | CATTAGCTTC | CACTGCCTCG | TGTGATATGA | 3642 |
| GGCCCATTCC TGCCTCTTTG | AAGAGAGCAG | TCAGCATTCT | TAGCAGTGAG | 3692 |
| TTTCTGTTCT GTTGGATGAC | TTTGAGATTT | ATCTTTCTTT | CCTGTTGGAA | 3742 |
| TTGTTCAAAT GTTCCTTTTA | ACAAATGGTT | GGATGAACTT | CAGCATCCAA | 3792 |
| GTTTATGAAT GACAGTAGTC | ACACATAGTG | CTGTTTATAT | AGTTTAGGGG | 3842 |
| TAAGAGTCCT GTTTTTTATT | CAGATTGGGA | AATCCATTCC | ATTTTGTGAG | 3892 |
| TTGTCACATA ATAACAGCAG | TGGAATATGT | ATTTGCCTAT | ATTGTGAACG | 3942 |
| AATTAGCAGT AAAATACATG | ATACAAGGAA | CTCAAAAGAT | AGTTAATTCT | 3992 |
| TGCCTTATAC CTCAGTCTAT | TATGTAAAAT | TAAAATATG  | TGTATGTTTT | 4042 |
| TGCTTCTTTG AGAATGCAAA | AGAAATTAAA | TCTGAATAAA | TTCTTCCTGT | 4092 |
| TCACTGGCTC ATTTCTTTAC | CATTCACTCA | GCATCTGCTC | TGTGGAAGGC | 4142 |
| CCTGGTAGTA GTGGG      |            |            |            | 4157 |

( 2 ) INFORMATION FOR SEQ ID NO: 10:

( i ) SEQUENCE CHARACTERISTICS:
      ( A ) LENGTH: 662 base pairs
      ( B ) TYPE: nucleic acid
      ( C ) STRANDEDNESS: single
      ( D ) TOPOLOGY: linear ( i i ) MOLECULE TYPE: genomic DNA ( i x ) FEATURE:
      ( A ) NAME/KEY: MAGE-21 gene ( x i ) SEQUENCE DESCRIPTION: SEQ ID NO: 10:

|                     |            |            |            |     |
|---------------------|------------|------------|------------|-----|
| GGATCCCCAT GGATCCAGGA | AGAATCCAGT | TCCACCCCTG | CTGTGAACCC | 50  |
| AGGGAAGTCA CGGGGCCGGA | TGTGACGCCA | CTGACTTGCG | CGTTGGAGGT | 100 |
| CAGAGAACAG CGAGATTCTC | GCCCTGAGCA | ACGGCCTGAC | GTCGGCGGAG | 150 |
| GGAAGCAGGC GCAGGCTCCG | TGAGGAGGCA | AGGTAAGATG | CCGAGGGAGG | 200 |
| ACTGAGGCGG GCCTCACCCC | AGACAGAGGG | CCCCCAATAA | TCCAGCGCTG | 250 |
| CCTCTGCTGC CAGGCCTGGA | CCACCCTGCA | GGGGAAGACT | TCTCAGGCTC | 300 |
| AGTCGCCACC ACCTCACCCC | GCCACCCCCC | GCCGCTTTAA | CCGCAGGGAA | 350 |
| CTCTGGTGTA AGAGCTTTGT | GTGACCAGGG | CAGGGCTGGT | TAGAAGTGCT | 400 |
| CAGGGCCCAG ACTCAGCCAG | GAATCAAGGT | CAGGACCCCA | AGAGGGGACT | 450 |
| GAGGGTAACC CCCCGCACC  | CCCACCACCA | TTCCCATCCC | CCAACACCAA | 500 |
| CCCCACCCCC ATCCCCAAC  | ACCAAACCCA | CCACCATCGC | TCAAACATCA | 550 |
| ACGGCACCCC CAAACCCCGA | TTCCCATCCC | CACCCATCCT | GGCAGAATCG | 600 |
| GAGCTTTGCC CCTGCAATCA | ACCCACGGAA | GCTCCGGGAA | TGGCGGCCAA | 650 |
| GCACGCGGAT CC         |            |            |            | 662 |

( 2 ) INFORMATION FOR SEQ ID NO: 11:

( i ) SEQUENCE CHARACTERISTICS:
      ( A ) LENGTH: 1640 base pairs
      ( B ) TYPE: nucleic acid
      ( C ) STRANDEDNESS: single
      ( D ) TOPOLOGY: linear ( i i ) MOLECULE TYPE: cDNA to mRNA ( i x ) FEATURE:
  ( A ) NAME/KEY: cDNA MAGE-3

( x i ) SEQUENCE DESCRIPTION: SEQ ID NO: 11:

| | | | | |
|---|---|---|---|---|
| GCCGCGAGGG | AAGCCGGCCC | AGGCTCGGTG | AGGAGGCAAG | GTTCTGAGGG | 50 |
| GACAGGCTGA | CCTGGAGGAC | CAGAGGCCCC | CGGAGGAGCA | CTGAAGGAGA | 100 |
| AGATCTGCCA | GTGGGTCTCC | ATTGCCCAGC | TCCTGCCCAC | ACTCCCGCCT | 150 |
| GTTGCCCTGA | CCAGAGTCAT C | | | | 171 |

```
ATG CCT CTT GAG CAG AGG AGT CAG CAC TGC AAG CCT GAA GAA      213
GGC CTT GAG GCC CGA GGA GAG GCC CTG GGC CTG GTG GGT GCG      255
CAG GCT CCT GCT ACT GAG GAG CAG GAG GCT GCC TCC TCC TCT      297
TCT ACT CTA GTT GAA GTC ACC CTG GGG GAG GTG CCT GCT GCC      339
GAG TCA CCA GAT CCT CCC CAG AGT CCT CAG GGA GCC TCC AGC      381
CTC CCC ACT ACC ATG AAC TAC CCT CTC TGG AGC CAA TCC TAT      423
GAG GAC TCC AGC AAC CAA GAA GAG GAG GGG CCA AGC ACC TTC      465
CCT GAC CTG GAG TCC GAG TTC CAA GCA GCA CTC AGT AGG AAG      507
GTG GCC GAG TTG GTT CAT TTT CTG CTC CTC AAG TAT CGA GCC      549
AGG GAG CCG GTC ACA AAG GCA GAA ATG CTG GGG AGT GTC GTC      591
GGA AAT TGG CAG TAT TTC TTT CCT GTG ATC TTC AGC AAA GCT      633
TCC AGT TCC TTG CAG CTG GTC TTT GGC ATC GAG CTG ATG GAA      675
GTG GAC CCC ATC GGC CAC TTG TAC ATC TTT GCC ACC TGC CTG      717
GGC CTC TCC TAC GAT GGC CTG CTG GGT GAC AAT CAG ATC ATG      759
CCC AAG GCA GGC CTC CTG ATA ATC GTC CTG GCC ATA ATC GCA      801
AGA GAG GGC GAC TGT GCC CCT GAG GAG AAA ATC TGG GAG GAG      843
CTG AGT GTG TTA GAG GTG TTT GAG GGG AGG GAA GAC AGT ATG      885
TTG GGG GAT CCC AAG AAG CTG CTC ACC CAA CAT TTC GTG CAG      927
GAA AAC TAC CTG GAG TAC CGG CAG GTC CCC GGC AGT GAT CCT      969
GCA TGT TAT GAA TTC CTG TGG GGT CCA AGG GCC CTC GTT GAA     1011
ACC AGC TAT GTG AAA GTC CTG CAC CAT ATG GTA AAG ATC AGT     1053
GGA GGA CCT CAC ATT TCC TAC CCA CCC CTG CAT GAG TGG GTT     1095
TTG AGA GAG GGG GAA GAG TGA                                  1116
```

| | | | | |
|---|---|---|---|---|
| GTCTGAGCAC | GAGTTGCAGC | CAGGGCCAGT | GGGAGGGGGT | CTGGGCCAGT | 1166 |
| GCACCTTCCG | GGGCCGCATC | CCTTAGTTTC | CACTGCCTCC | TGTGACGTGA | 1216 |
| GGCCCATTCT | TCACTCTTTG | AAGCGAGCAG | TCAGCATTCT | TAGTAGTGGG | 1266 |
| TTTCTGTTCT | GTTGGATGAC | TTTGAGATTA | TTCTTTGTTT | CCTGTTGGAG | 1316 |
| TTGTTCAAAT | GTTCCTTTTA | ACGGATGGTT | GAATGAGCGT | CAGCATCCAG | 1366 |
| GTTTATGAAT | GACAGTAGTC | ACACATAGTG | CTGTTTATAT | AGTTTAGGAG | 1416 |
| TAAGAGTCTT | GttTTTTACT | CAAATTgGGA | AATCCATTCC | ATTTGTGAA | 1466 |
| TTGTGACATA | ATAATAGCAG | TGGTAAAAGT | ATTTGCTTAA | AATTGTGAGC | 1516 |
| GAATTAGCAA | TAACATACAT | GAGATAACTC | AAGAAATCAA | AAGATAGTTG | 1566 |
| ATTCTTGCCT | TGTACCTCAA | TCTATTCTGT | AAAATTAAAC | AAATATGCAA | 1616 |

ACCAGGATTT CCTTGACTTC TTTG                                                                          1640

( 2 ) INFORMATION FOR SEQ ID NO: 12:

( i ) SEQUENCE CHARACTERISTICS:
        ( A ) LENGTH: 943 base pairs
        ( B ) TYPE: nucleic acid
        ( C ) STRANDEDNESS: single
        ( D ) TOPOLOGY: linear ( i i ) MOLECULE TYPE: genomic DNA ( i x ) FEATURE:
        ( A ) NAME/KEY: MAGE-31 gene ( x i ) SEQUENCE DESCRIPTION: SEQ ID NO: 12:

```
GGATCCTCCA  CCCCAGTAGA  GTGGGGACCT  CACAGAGTCT  GGCCAACCCT          50
CCTGACAGTT  CTGGGAATCC  GTGGCTGCGT  TTGCTGTCTG  CACATTGGGG         100
GCCCGTGGAT  TCCTCTCCCA  GGAATCAGGA  GCTCCAGGAA  CAAGGCAGTG         150
AGGACTTGGT  CTGAGGCAGT  GTCCTCAGGT  CACAGAGTAG  AGGGGgCTCA         200
GATAGTGCCA  ACGGTGAAGG  TTTGCCTTGG  ATTCAAACCA  AGGGCCCCAC         250
CTGCCCCAGA  ACACATGGAC  TCCAGAGCGC  CTGGCCTCAC  CCTCAATACT         300
TTCAGTCCTG  CAGCCTCAGC  ATGCGCTGGC  CGGATGTACC  CTGAGGTGCC         350
CTCTCACTTC  CTCCTTCAGG  TTCTGAGGGG  ACAGGCTGAC  CTGGAGGACC         400
AGAGGCCCCC  GGAGGAGCAC  TGAAGGAGAA  GATCTGTAAG  TAAGCCTTTG         450
TTAGAGCCTC  CAAGGTTCCA  TTCAGTACTC  AGCTGAGGTC  TCTCACATGC         500
TCCCTCTCTC  CCCAGGCCAG  TGGGTCTCCA  TTGCCCAGCT  CCTGCCCACA         550
CTCCCGCCTG  TTGCCCTGAC  CAGAGTCATC                                 580
```

```
ATG  CCT  CTT  GAG  CAG  AGG  AGT  CAG  CAC  TGC  AAG  CCT  GAA  GAA   622
GGC  CTT  GAG  GCC  CGA  GGA  GAg  GCC  CTG  GGC  CTG  GTG  GGT  GCG   664
CAG  GCT  CCT  GCT  ACT  GAG  GAG  CAG  GAG  GCT  GCC  TCC  TCC  TCT   706
TCT  AGT  GTA  GTT  GAA  GTC  ACC  CTG  GGG  GAG  GTG  CCT  GCT  GCC   748
GAG  TCA  CCA  GAT  CCT  CCC  CAG  AGT  CCT  CAG  GGA  GCC  TCC  AGC   790
CTC  CCC  ACT  ACC  ATG  AAC  TAC  CCT  CTC  TGG  AGC  CAA  TCC  TAT   832
GAG  GAC  TCC  AGC  AAC  CAA  GAA  GAG  GAG  GGG  CCA  AGC  ACC  TTC   874
CCT  GAC  CTG  GAG  TCT  GAG  TTC  CAA  GCA  GCA  CTC  AGT  AGG  AAG   916
GTG  GCC  AAG  TTG  GTT  CAT  TTT  CTG  CTC                            943
```

( 2 ) INFORMATION FOR SEQ ID NO: 13:

( i ) SEQUENCE CHARACTERISTICS:
        ( A ) LENGTH: 2531 base pairs
        ( B ) TYPE: nucleic acid
        ( C ) STRANDEDNESS: single
        ( D ) TOPOLOGY: linear ( i i ) MOLECULE TYPE: genomic DNA ( i x ) FEATURE:
        ( A ) NAME/KEY: MAGE-4 gene ( x i ) SEQUENCE DESCRIPTION: SEQ ID NO: 13:

```
GGATCCAGGC  CCTGCCTGGA  GAAATGTGAG  GGCCCTGAGT  GAACACAGTG          50
GGGATCATCC  ACTCCATGAG  AGTGGGGACC  TCACAGAGTC  CAGCCTACCC         100
```

```
TCTTGATGGC ACTGAGGGAC CGGGGCTGTG CTTACAGTCT GCACCCTAAG        150
GGCCCATGGA TTCCTCTCCT AGGAGCTCCA GGAACAAGGC AGTGAGGCCT        200
TGGTCTGAGA CAGTGTCCTC AGGTTACAGA GCAGAGGATG CACAGGCTGT        250
GCCAGCAGTG AATGTTTGCC CTGAATGCAC ACCAAGGGCC CCACCTGCCA        300
CAAGACACAT AGGACTCCAA AGAGTCTGGC CTCACCTCCC TACCATCAAT        350
CCTGCAGAAT CGACCTCTGC TGGCCGGCTA TACCCTGAGG TGCTCTCTCA        400
CTTCCTCCTT CAGGTTCTGA GCAGACAGGC CAACCGGAGA CAGGATTCCC        450
TGGAGGCCAC AGAGGAGCAC CAAGGAGAAG ATCTGTAAGT AAGCCTTTGT        500
TAGAGCCTCT AAGATTTGGT TCTCAGCTGA GGTCTCTCAC ATGCTCCCTC        550
TCTCCGTAGG CCTGTGGGTC CCCATTGCCC AGCTTTTGCC TGCACTCTTG        600
CCTGCTGCCC TGACCAGAGT CATC                                   624
ATG TCT TCT GAG CAG AAG AGT CAG CAC TGC AAG CCT GAG GAA      666
GGC GTT GAG GCC CAA GAA GAG GCC CTG GGC CTG GTG GGT GCA      708
CAG GCT CCT ACT ACT GAG GAG CAG GAG GCT GCT GTC TCC TCC      750
TCC TCT CCT CTG GTC CCT GGC ACC CTG AGG AAG TG CCT GCT       792
GCT GAG TCA GCA GGT CCT CCC CAG AGT CCT CAG GGA GCC TCT      834
GCC TTA CCC ACT ACC ATC AGC TTC ACT TGC TGG AGG CAA CCC      876
AAT GAG GGT TCC AGC AGC CAA GAA GAG GAG GGG CCA AGC ACC      918
TCG CCT GAC GCA GAG TCC TTG TTC CGA AAG CA CTC AGT AAC       960
AAG GTG GAT GAG TTG GCT CAT TTT CTG CTC CGC AAG TAT CGA      1002
GCC AAG GAG CTG GTC ACA AAG GCA GAA ATG CTG GAG AGA GTC      1044
ATC AAA AAT TAC AAG CGC TGC TTT CCT GTG ATC TTC GGC AAA      1086
GCC TCC GAG TCC CTG AAG ATG ATC TTT GGC ATT GAC GTG AAG      1128
GAA GTG GAC CCC GCC AGC AAC ACC TAC ACC CTT GTC ACC TGC      1170
CTG GGC CTT TCC TAT GAT GGC CTG CTG GGT AAT AAT CAG ATC      1212
TTT CCC AAG ACA GGC CTT CTG ATA ATC GTC CTG GGC ACA ATT      1254
GCA ATG GAG GGC GAC AGC GCC TCT GAG GAG GAA ATC TGG GAG      1296
GAG CTG GGT GTG ATG GGG GTG TAT GAT GGG AGG GAG CAC ACT      1338
GTC TAT GGG GAG CCC AGG AAA CTG CTC ACC CAA GAT TGG GTG      1380
CAG GAA AAC TAC CTG GAG TAC CGG CAG GTA CCC GGC AGT AAT      1422
CCT GCG CGC TAT GAG TTC CTG TGG GGT CCA AGG GCT CTG GCT      1464
GAA ACC AGC TAT GTG AAA GTC CTG GAG CAT GTG GTC AGG GTC      1506
AAT GCA AGA GTT CGC ATT GCC TAC CCA TCC CTG CGT GAA GCA      1548
GCT TTG TTA GAG GAG GAA GAG GGA GTC TGA                      1578
GCATGAGTTG CAGCCAGGGC TGTGGGGAAG GGGCAGGGCT GGGCCAGTGC       1628
ATCTAACAGC CCTGTGCAGC AGCTTCCCTT GCCTCGTGTA ACATGAGGCC       1678
CATTCTTCAC TCTGTTTGAA GAAAATAGTC AGTGTTCTTA GTAGTGGGTT       1728
TCTATTTTGT TGGATGACTT GGAGATTTAT CTCTGTTTCC TTTTACAATT       1778
GTTGAAATGT TCCTTTTAAT GGATGGTTGA ATTAACTTCA GCATCCAAGT       1828
TTATGAATCG TAGTTAACGT ATATTGCTGT TAATATAGTT TAGGAGTAAG       1878
```

| | | | | |
|---|---|---|---|---|
| AGTCTTGTTT | TTTATTCAGA | TTGGGAAATC | CGTTCTATTT | TGTGAATTTG | 1928 |
| GGACATAATA | ACAGCAGTGG | AGTAAGTATT | TAGAAGTGTG | AATTCACCGT | 1978 |
| GAAATAGGTG | AGATAAATTA | AAAGATACTT | AATTCCCGCC | TTATGCCTCA | 2028 |
| GTCTATTCTG | TAAAATTTAA | AAATATATAT | GCATACCTGG | ATTTCCTTGG | 2078 |
| CTTCGTGAAT | GTAAGAGAAA | TTAAATCTGA | ATAAATAATT | CTTTCTGTTA | 2128 |
| ACTGGCTCAT | TTCTTCTCTA | TGCACTGAGC | ATCTGCTCTG | TGGAAGGCCC | 2178 |
| AGGATTAGTA | GTGGAGATAC | TAGGGTAAGC | CAGACACACA | CCTACCGATA | 2228 |
| GGGTATTAAG | AGTCTAGGAG | CGCGGTCATA | TAATTAAGGT | GACAAGATGT | 2278 |
| CCTCTAAGAT | GTAGGGGAAA | AGTAACGAGT | GTGGGTATGG | GGCTCCAGGT | 2328 |
| GAGAGTGGTC | GGGTGTAAAT | TCCCTGTGTG | GGGCCTTTTG | GGCTTTGGGA | 2378 |
| AACTGCATTT | TCTTCTGAGG | GATCTGATTC | TAATGAAGCT | TGGTGGGTCC | 2428 |
| AGGGCCAGAT | TCTCAGAGGG | AGAGGGAAAA | GCCCAGATTG | GAAAAGTTGC | 2478 |
| TCTGAGCAGT | TCCTTTGTGA | CAATGGATGA | ACAGAGAGGA | GCCTCTACCT | 2528 |
| GGG | | | | | 2531 |

( 2 ) INFORMATION FOR SEQ ID NO: 14:

( i ) SEQUENCE CHARACTERISTICS:
        ( A ) LENGTH: 2531 base pairs
        ( B ) TYPE: nucleic acid
        ( C ) STRANDEDNESS: single
        ( D ) TOPOLOGY: linear ( i i ) MOLECULE TYPE: genomic DNA ( i x ) FEATURE:
        ( A ) NAME/KEY: MAGE-41 gene ( x i ) SEQUENCE DESCRIPTION: SEQ ID NO: 14:

| | | | | | |
|---|---|---|---|---|---|
| GGATCCAGGC | CCTGCCTGGA | GAAATGTGAG | GGCCCTGAGT | GAACACAGTG | 50 |
| GGGATCATCC | ACTCCATGAG | AGTGGGGACC | TCACAGAGTC | CAGCCTACCC | 100 |
| TCTTGATGGC | ACTGAGGGAC | CGGGGCTGTG | CTTACAGTCT | GCACCCTAAG | 150 |
| GGCCCATGGA | TTCCTCTCCT | AGGAGCTCCA | GGAACAAGGC | AGTGAGGCCT | 200 |
| TGGTCTGAGA | CAGTGTCCTC | AGGTTACAGA | GCAGAGGATG | CACAGGCTGT | 250 |
| GCCAGCAGTG | AATGTTTGCC | CTGAATGCAC | ACCAAGGGCC | CCACCTGCCA | 300 |
| CAAGACACAT | AGGACTCCAA | AGAGTCTGGC | CTCACCTCCC | TACCATCAAT | 350 |
| CCTGCAGAAT | CGACCTCTGC | TGGCCGGCTA | TACCCTGAGG | TGCTCTCTCA | 400 |
| CTTCCTCCTT | CAGGTTCTGA | GCAGACAGGC | CAACCGGAGA | CAGGATTCCC | 450 |
| TGGAGGCCAC | AGAGGAGCAC | CAAGGAGAAG | ATCTGTAAGT | AAGCCTTTGT | 500 |
| TAGAGCCTCT | AAGATTTGGT | TCTCAGCTGA | GGTCTCTCAC | ATGCTCCCTC | 550 |
| TCTCCGTAGG | CCTGTGGGTC | CCCATTGCCC | AGCTTTTGCC | TGCACTCTTG | 600 |
| CCTGCTGCCC | TGAGCAGAGT | CATC | | | 624 |
| ATG TCT | TCT GAG CAG | AAG AGT CAG | CAC TGC AAG | CCT GAG GAA | 666 |
| GGC GTT | GAG GCC CAA | GAA GAG GCC | CTG GGC CTG | GTG GGT GCG | 708 |
| CAG GCT | CCT ACT ACT | GAG GAG CAG | GAG GCT GCT | GTC TCC TCC | 750 |
| TCC TCT | CCT CTG GTC | CCT GGC ACC | CTG GAG GAA | GTG CCT GCT | 792 |
| GCT GAG | TCA GCA GGT | CCT CCC CAG | AGT CCT CAG | GGA GCC TCT | 834 |

| | | |
|---|---|---|
| GCC TTA CCC ACT ACC ATC AGC TTC ACT TGC TGG AGG CAA CCC | | 876 |
| AAT GAG GGT TCC AGC AGC CAA GAA GAG GAG GGG CCA AGC ACC | | 918 |
| TCG CCT GAC GCA GAG TCC TTG TTC CGA GAA GCA CTC AGT AAC | | 960 |
| AAG GTG GAT GAG TTG GCT CAT TTT CTG CTC CGC AAG TAT CGA | | 1002 |
| GCC AAG GAG CTG GTC ACA AAG GCA GAA ATG CTG GAG AGA GTC | | 1044 |
| ATC AAA AAT TAC AAG CGC TGC TTT CCT GTG ATC TTC GGC AAA | | 1086 |
| GCC TCC GAG TCC CTG AAG ATG ATC TTT GGC ATT GAC GTG AAG | | 1128 |
| GAA GTG GAC CCC ACC AGC AAC ACC TAC ACC CTT GTC ACC TGC | | 1170 |
| CTG GGC CTT TCC TAT GAT GGC CTG CTG GGT AAT AAT CAG ATC | | 1212 |
| TTT CCC AAG ACA GGC CTT CTG ATA ATC GTC CTG GGC ACA ATT | | 1254 |
| GCA ATG GAG GGC GAC AGC GCC TCT GAG GAG GAA ATC TGG GAG | | 1296 |
| GAG CTG GGT GTG ATG GGG GTG TAT GAT GGG AGG GAG CAC ACT | | 1338 |
| GTC TAT GGG GAG CCC AGG AAA CTG CTC ACC CAA GAT TGG GTG | | 1380 |
| CAG GAA AAC TAC CTG GAG TAC CGG CAG GTA CCC GGC AGT AAT | | 1422 |
| CCT GCG CGC TAT GAG TTC CTG TGG GGT CCA AGG GCT CTG GCT | | 1464 |
| GAA ACC AGC TAT GTG AAA GTC CTG GAG CAT GTG GTC AGG GTC | | 1506 |
| AAT GCA AGA GTT CGC ATT GCC TAC CCA TCC CTG CGT GAA GCA | | 1548 |
| GCT TTG TTA GAG GAG GAA GAG GGA GTC TGA | | 1578 |
| GCATGAGTTG CAGCCAGGGC TGTGGGGAAG GGGCAGGGCT GGCCAGTGC | | 1628 |
| ATCTAACAGC CCTGTGCAGC AGCTTCCCTT GCCTCGTGTA ACATGAGGCC | | 1678 |
| CATTCTTCAC TCTGTTTGAA GAAATAGTC AGTGTTCTTA GTAGTGGGTT | | 1728 |
| TCTATTTTGT TGGATGACTT GGAGATTTAT CTCTGTTTCC TTTTACAATT | | 1778 |
| GTTGAAATGT TCCTTTTAAT GGATGGTTGA ATTAACTTCA GCATCCAAGT | | 1828 |
| TTATGAATCG TAGTTAACGT ATATTGCTGT TAATATAGTT TAGGAGTAAG | | 1878 |
| AGTCTTGTTT TTTATTCAGA TTGGGAAATC CGTTCTATTT TGTGAATTTG | | 1928 |
| GGACATAATA ACAGCAGTGG AGTAAGTATT TAGAAGTGTG AATTCACCGT | | 1978 |
| GAAATAGGTG AGATAAATTA AAAGATACTT AATTCCGCC TTATGCCTCA | | 2028 |
| GTCTATTCTG TAAAATTTAA AAATATATAT GCATACCTGG ATTTCCTTGG | | 2078 |
| CTTCGTGAAT GTAAGAGAAA TTAAATCTGA ATAAATAATT CTTTCTGTTA | | 2128 |
| ACTGGCTCAT TTCTTCTCTA TGCACTGAGC ATCTGCTCTG TGGAAGGCCC | | 2178 |
| AGGATTAGTA GTGGAGATAC TAGGGTAAGC CAGACACACA CCTACCGATA | | 2228 |
| GGGTATTAAG AGTCTAGGAG CGCGGTCATA TAATTAAGGT GACAAGATGT | | 2278 |
| CCTCTAAGAT GTAGGGAAA AGTAACGAGT GTGGGTATGG GGCTCCAGGT | | 2328 |
| GAGAGTGGTC GGGTGTAAAT TCCCTGTGTG GGGCCTTTTG GGCTTTGGGA | | 2378 |
| AACTCCATTT TCTTCTGAGG GATCTGATTC TAATGAAGCT TGGTGGGTCC | | 2428 |
| AGGGCCAGAT TCTCAGAGGG AGAGGGAAAA GCCCAGATTG GAAAAGTTGC | | 2478 |
| TCTGAGCGGT TCCTTTGTGA CAATGGATGA ACAGAGAGGA GCCTCTACCT | | 2528 |
| GGG | | 2531 |

( 2 ) INFORMATION FOR SEQ ID NO: 15:

( i ) SEQUENCE CHARACTERISTICS:

-continued (A) LENGTH: 1068 base pairs
(B) TYPE: nucleic acid
(C) STRANDEDNESS: single
(D) TOPOLOGY: linear (ii) MOLECULE TYPE: cDNA to mRNA (ix) FEATURE:
(A) NAME/KEY: cDNA MAGE-4

(xi) SEQUENCE DESCRIPTION: SEQ ID NO: 15:

| G | GGG | CCA | AGC | ACC | TCG | CCT | GAC | GCA | GAG | TCC | TTG | TTC | CGA | 40 |
|---|-----|-----|-----|-----|-----|-----|-----|-----|-----|-----|-----|-----|-----|----|
| GAA | GCA | CTC | AGT | AAC | AAG | GTG | GAT | GAG | TTG | GCT | CAT | TTT | CTG | 82 |
| CTC | CGC | AAG | TAT | CGA | GCC | AAG | GAG | CTG | GTC | ACA | AAG | GCA | GAA | 124 |
| ATG | CTG | GAG | AGA | GTC | ATC | AAA | AAT | TAC | AAG | CGC | TGC | TTT | CCT | 166 |
| GTG | ATC | TTC | GGC | AAA | GCC | TCC | GAG | TCC | CTG | AAG | ATG | ATC | TTT | 208 |
| GGC | ATT | GAC | GTG | AAG | GAA | GTG | GAC | CCC | GCC | AGC | AAC | ACC | TAC | 250 |
| ACC | CTT | GTC | ACC | TGC | CTG | GGC | CTT | TCC | TAT | GAT | GGC | CTG | CTG | 292 |
| GGT | AAT | AAT | CAG | ATC | TTT | CCC | AAG | ACA | GGC | CTT | CTG | ATA | ATC | 334 |
| GTC | CTG | GGC | ACA | ATT | GCA | ATG | GAG | GGC | GAC | AGC | GCC | TCT | GAG | 376 |
| GAG | GAA | ATC | TGG | GAG | GAG | CTG | GGT | GTG | ATG | GGG | GTG | TAT | GAT | 418 |
| GGG | AGG | GAG | CAC | ACT | GTC | TAT | GGG | GAG | CCC | AGG | AAA | CTG | CTC | 460 |
| ACC | CAA | GAT | TGG | GTG | CAG | GAA | AAC | TAC | CTG | GAG | TAC | CGG | CAG | 502 |
| GTA | CCC | GGC | AGT | AAT | CCT | GCG | CGC | TAT | GAG | TTC | CTG | TGG | GGT | 544 |
| CCA | AGG | GCT | CTG | GCT | GAA | ACC | AGC | TAT | GTG | AAA | GTC | CTG | GAG | 586 |
| CAT | GTG | GTC | AGG | GTC | AAT | GCA | AGA | GTT | CGC | ATT | GCC | TAC | CCA | 628 |
| TCC | CTG | CGT | GAA | GCA | GCT | TTG | TTA | GAG | GAG | GAA | GAG | GGA | GTC | 670 |

| TGAGCATGAG | TTGCAGCCAG | GGCTGTGGGG | AAGGGGCAGG | GCTGGGCCAG | 720 |
|------------|------------|------------|------------|------------|-----|
| TGCATCTAAC | AGCCCTGTGC | AGCAGCTTCC | CTTGCCTCGT | GTAACATGAG | 770 |
| GCCCATTCTT | CACTCTGTTT | GAAGAAAATA | GTCAGTGTTC | TTAGTAGTGG | 820 |
| GTTTCTATTT | TGTTGGATGA | CTTGGAGATT | TATCTCTGTT | TCCTTTTACA | 870 |
| ATTGTTGAAA | TGTTCCTTTT | AATGGATGGT | TGAATTAACT | TCAGCATCCA | 920 |
| AGTTTATGAA | TCGTAGTTAA | CGTATATTGC | TGTTAATATA | GTTTAGGAGT | 970 |
| AAGAGTCTTG | TTTTTTATTC | AGATTGGGAA | ATCCGTTCTA | TTTTGTGAAT | 1020 |
| TTGGGACATA | ATAACAGCAG | TGGAGTAAGT | ATTTAGAAGT | GTGAATTC | 1068 |

(2) INFORMATION FOR SEQ ID NO: 16:

(i) SEQUENCE CHARACTERISTICS:
(A) LENGTH: 2226 base pairs
(B) TYPE: nucleic acid
(C) STRANDEDNESS: single
(D) TOPOLOGY: linear (ii) MOLECULE TYPE: genomic DNA (ix) FEATURE:
(A) NAME/KEY: MAGE-5 gene (xi) SEQUENCE DESCRIPTION: SEQ ID NO: 16:

| GGATCCAGGC | CTTGCCAGGA | GAAAGGTGAG | GGCCCTGTGT | GAGCACAGAG | 50 |
|------------|------------|------------|------------|------------|-----|
| GGGACCATTC | ACCCCAAGAG | GGTGGAGACC | TCACAGATTC | CAGCCTACCC | 100 |

```
TCCTGTTAGC ACTGGGGGCC TGAGGCTGTG CTTGCAGTCT GCACCCTGAG        150
GGCCCATGCA TTCCTCTTCC AGGAGCTCCA GGAAACAGAC ACTGAGGCCT        200
TGGTCTGAGG CCGTGCCCTC AGGTCACAGA GCAGAGGAGA TGCAGACGTC        250
TAGTGCCAGC AGTGAACGTT TGCCTTGAAT GCACACTAAT GGCCCCCATC        300
GCCCCAGAAC ATATGGGACT CCAGAGCACC TGGCCTCACC CTCTCTACTG        350
TCAGTCCTGC AGAATCAGCC TCTGCTTGCT TGTGTACCCT GAGGTGCCCT        400
CTCACTTTTT CCTTCAGGTT CTCAGGGGAC AGGCTGACCA GGATCACCAG        450
GAAGCTCCAG AGGATCCCCA GGAGGCCCTA GAGGAGCACC AAAGGAGAAG        500
ATCTGTAAGT AAGCCTTTGT TAGAGCCTCC AAGGTTCAGT TTTTAGCTGA        550
GGCTTCTCAC ATGCTCCCTC TCTCCAGG  CCAGTGGGTC TCCATTGCCC         600
AGCTCCTGCC CACACTCCTG CCTGTTGCGG TGACCAGAGT CGTC              644
ATG TCT CTT GAG CAG AAG AGT CAG CAC TGC AAG CCT GAG GAA       686
CTC CTC TGG TCC CAG GCA CCC TGG GGG AGG TGC CTG CTG CTG       728
GGT CAC CAG GTC CTC TCA AGA GTC CTC AGG GAG CCT CCG CCA       770
TCC CCA CTG CCA TCG ATT TCA CTC TAT GGA GGC AAT CCA TTA       812
AGG GCT CCA GCA ACC AAG AAG AGG AGG GGC CAA GCA CCT CCC       854
CTG ACC CAG AGT CTG TGT CCG AGC AGC ACT CAG TAA GAA GG        896
TGG CTG ACT TGA                                               908
TTCATTTTCT GCTCCTCAAG TATTAAGTCA AGGAGCTGGT CACAAAGGCA         958
GAAATGCTGG AGAGCGTCAT CAAAAATTAC AAGCGCTGCT TCCTGAGAT         1008
CTTCGGCAAA GCCTCCGAGT CCTTGCAGCT GGTCTTTGGC ATTGACGTGA        1058
AGGAAGCGGA CCCCACCAGC AACACCTACA CCCTTGTCAC CTGCCTGGGA        1108
CTCCTATGAT GGCCTGCTGG TTGATAATAA TCAGATCATG CCCAAGACGG        1158
GCCTCCTGAT AATCGTCTTG GGCATGATTG CAATGGAGGG CAAATGCGTC        1208
CCTGAGGAGA AAATCTGGGA GGAGCTGAGT GTGATGAAGG TGTATGTTGG        1258
GAGGGAGCAC AGTGTCTGTG GGGAGCCCAG GAAGCTGCTC ACCCAAGATT        1308
TGGTGCAGGA AAACTACCTG GAGTACCGGC AGGTGCCCAG CAGTGATCCC        1358
ATATGCTATG AGTTACTGTG GGGTCCAAGG GCACTCGCTG CTTGAAAGTA        1408
CTGGAGCACG TGGTCAGGGT CAATGCAAGA GTTCTCATTT CCTACCCATC        1458
CCTGCGTGAA GCAGCTTTGA GAGAGGAGGA AGAGGGAGTC TGAGCATGAG        1508
CTGCAGCCAG GGCCACTGCG AGGGGGGCTG GGCCAGTGCA CCTTCCAGGG        1558
CTCCGTCCAG TAGTTTCCCC TGCCTTAATG TGACATGAGG CCCATTCTTC        1608
TCTCTTTGAA GAGAGCAGTC AACATTCTTA GTAGTGGGTT TCTGTTCTAT        1658
TGGATGACTT TGAGATTTGT CTTTGTTTCC TTTTGGAATT GTTCAAATGT        1708
TTCTTTTAAT GGGTGGTTGA ATGAACTTCA GCATTCAAAT TTATGAATGA        1758
CAGTAGTCAC ACATAGTGCT GTTTATATAG TTTAGGAGTA AGAGTCTTGT        1808
TTTTTATTCA GATTGGGAAA TCCATTCCAT TTTGTGAATT GGGACATAGT        1858
TACAGCAGTG GAATAAGTAT TCATTTAGAA ATGTGAATGA GCAGTAAAAC        1908
TGATGACATA AAGAAATTAA AAGATATTTA ATTCTTGCTT ATACTCAGTC        1958
TATTCGGTAA AATTTTTTTT AAAAAATGTG CATACCTGGA TTTCCTTGGC        2008
```

5,612,201

```
TTCTTTGAGA ATGTAAGACA AATTAAATCT GAATAAATCA TTCTCCCTGT         2058

TCACTGGCTC ATTTATTCTC TATGCACTGA GCATTTGCTC TGTGGAAGGC         2108

CCTGGGTTAA TAGTGGAGAT GCTAAGGTAA GCCAGACTCA CCCCTACCCA         2158

CAGGGTAGTA AAGTCTAGGA GCAGCAGTCA TATAATTAAG GTGGAGAGAT         2208

GCCCTCTAAG ATGTAGAG                                             2226
```

( 2 ) INFORMATION FOR SEQ ID NO: 17:

( i ) SEQUENCE CHARACTERISTICS:
        ( A ) LENGTH: 2305 base pairs
        ( B ) TYPE: nucleic acid
        ( C ) STRANDEDNESS: single
        ( D ) TOPOLOGY: linear ( i i ) MOLECULE TYPE: genomic DNA ( i x ) FEATURE:
        ( A ) NAME/KEY: MAGE-51 gene ( x i ) SEQUENCE DESCRIPTION: SEQ ID NO: 17:

```
GGATCCAGGC CTTGCCAGGA GAAAGGTGAG GGCCCTGTGT GAGCACAGAG         50

GGGACCATTC ACCCCAAGAG GGTGGAGACC TCACAGATTC CAGCCTACCC         100

TCCTGTTAGC ACTGGGGGCC TGAGGCTGTG CTTGCAGTCT GCACCCTGAG         150

GGCCCATGCA TTCCTCTTCC AGGAGCTCCA GGAAACAGAC ACTGAGGCCT         200

TGGTCTGAGG CCGTGCCCTC AGGTCACAGA GCAGAGGAGA TGCAGACGTC         250

TAGTGCCAGC AGTGAACGTT TGCCTTGAAT GCACACTAAT GGCCCCATC          300

GCCCCAGAAC ATATGGGACT CCAGAGCACC TGGCCTCACC CTCTCTACTG         350

TCAGTCCTGC AGAATCAGCC TCTGCTTGCT TGTGTACCCT GAGGTGCCCT         400

CTCACTTTTT CCTTCAGGTT CTCAGGGGAC AGGCTGACCA GGATCACCAG         450

GAAGCTCCAG AGGATCCCCA GGAGGCCCTA GAGGAGCACC AAAGGAGAAG         500

ATCTGTAAGT AAGCCTTTGT TAGAGCCTCC AAGGTTCAGT TTTTAGCTGA         550

GGCTTCTCAC ATGCTCCCTC TCTCTCCAGG CCAGTGGGTC TCCATTGCCC         600

AGCTCCTGCC CACACTCCTG CCTGTTGCGG TGACCAGAGT CGTC              644

ATG TCT CTT GAG CAG AAG AGT CAG CAC TGC AAG CCT GAG GAA         686

GGC CTT GAC ACC CAA GAA GAG CCC TGG GCC TGG TGG GTG TGC         728

AGG CTG CCA CTA CTG AGG AGC AGG AGG CTG TGT CCT CCT CCT         770

CTC CTC TGG TCC CAG GCA CCC TGG GGG AGG TGC CTG CTG CTG         812

GGT CAC CAG GTC CTC TCA AGA GTC CTC AGG GAG CCT CCG CCA         854

TCC CCA CTG CCA TCG ATT TCA CTC TAT GGA GGC AAT CCA TTA         896

AGG GCT CCA GCA ACC AAG AAG AGG AGG GGC CAA GCA CCT CCC         938

CTG ACC CAG AGT CTG TGT TCC GAG CAG CAC TCA GTA AGA AGG         980

TGG CTG ACT TGA                                                992

TTCATTTTCT GCTCCTCAAG TATTAAGTCA AGGAGCCGGT CACAAAGGCA         1042

GAAATGCTGG AGAGCGTCAT CAAAAATTAC AAGCGCTGCT TTCCTGAGAT         1092

CTTCGGCAAA GCCTCCGAGT CCTTGCAGCT GGTCTTTGGC ATTGACGTGA         1142

AGGAAGCGGA CCCCACCAGC AACACCTACA CCCTTGTCAC CTGCCTGGGA         1192

CTCCTATGAT GGCCTGGTGG TTTAATCAGA TCATGCCCAA GACGGGCCTC         1242
```

| | | | | | |
|---|---|---|---|---|---|
| CTGATAATCG | TCTTGGGCAT | GATTGCAATG | GAGGGCAAAT | GCGTCCCTGA | 1292 |
| GGAGAAAATC | TGGGAGGAGC | TGGGTGTGAT | GAAGGTGTAT | GTTGGGAGGG | 1342 |
| AGCACAGTGT | CTGTGGGGAG | CCCAGGAAGC | TGCTCACCCA | AGATTTGGTG | 1392 |
| CAGGAAAACT | ACCTGGAGTA | CCGCAGGTGC | CCAGCAGTGA | TCCCATATGC | 1442 |
| TATGAGTTAC | TGTGGGGTCC | AAGGGCACTC | GCTGCTTGAA | AGTACTGGAG | 1492 |
| CACGTGGTCA | GGGTCAATGC | AAGAGTTCTC | ATTTCCTACC | CATCCCTGCA | 1542 |
| TGAAGCAGCT | TTGAGAGAGG | AGGAAGAGGG | AGTCTGAGCA | TGAGCTGCAG | 1592 |
| CCAGGGCCAC | TGCGAGGGGG | GCTGGGCCAG | TGCACCTTCC | AGGGCTCCGT | 1642 |
| CCAGTAGTTT | CCCCTGCCTT | AATGTGACAT | GAGGCCCATT | CTTCTCTCTT | 1692 |
| TGAAGAGAGC | AGTCAACATT | CTTAGTAGTG | GGTTTCTGTT | CTATTGGATG | 1742 |
| ACTTTGAGAT | TTGTCTTTGT | TTCCTTTTGG | AATTGTTCAA | ATGTTCCTTT | 1792 |
| TAATGGGTGG | TTGAATGAAC | TTCAGCATTC | AAATTTATGA | ATGACAGTAG | 1842 |
| TCACACATAG | TGCTGTTTAT | ATAGTTTAGG | AGTAAGAGTC | TTGTTTTTA | 1892 |
| TTCAGATTGG | GAAATCCATT | CCATTTGTG | AATTGGGACA | TAGTTACAGC | 1942 |
| AGTGGAATAA | GTATTCATTT | AGAAATGTGA | ATGAGCAGTA | AAACTGATGA | 1992 |
| GATAAAGAAA | TTAAAGATA | TTTAATTCTT | GCCTTATACT | CAGTCTATTC | 2042 |
| GGTAAAATTT | TTTTTAAAA | ATGTGCATAC | CTGGATTTCC | TTGGCTTCTT | 2092 |
| TGAGAATGTA | AGACAAATTA | AATCTGAATA | AATCATTCTC | CCTGTTCACT | 2142 |
| GGCTCATTTA | TTCTCTATGC | ACTGAGCATT | TGCTCTGTGG | AAGGCCCTGG | 2192 |
| GTTAATAGTG | GAGATGCTAA | GGTAAGCCAG | ACTCACCCCT | ACCCACAGGG | 2242 |
| TAGTAAAGTC | TAGGAGCAGC | AGTCATATAA | TTAAGGTGGA | GAGATGCCCT | 2292 |
| CTAAGATGTA | GAG | | | | 2305 |

( 2 ) INFORMATION FOR SEQ ID NO: 18:

( i ) SEQUENCE CHARACTERISTICS:
    ( A ) LENGTH: 225 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: MAGE-6 gene ( x i ) SEQUENCE DESCRIPTION: SEQ ID NO: 18:

| | | | | | | | | | | | | | |
|---|---|---|---|---|---|---|---|---|---|---|---|---|---|
| TAT | TTC | TTT | CCT | GTG | ATC | TTC | AGC | AAA | GCT | TCC | GAT | TCC | TTG | 42 |
| CAG | CTG | GTC | TTT | GGC | ATC | GAG | CTG | ATG | AAA | GTG | GAC | CCC | ATC | 84 |
| GGC | CAC | GTG | TAC | ATC | TTT | GCC | ACC | TGC | CTG | GGC | CTC | TCC | TAC | 126 |
| GAT | GGC | CTG | CTG | GGT | GAC | AAT | CAG | ATC | ATG | CCC | AGG | ACA | GGC | 168 |
| TTC | CTG | ATA | ATC | ATC | CTG | GCC | ATA | ATC | GCA | AGA | GAG | GGC | GAC | 210 |
| TGT | GCC | CCT | GAG | GAG | | | | | | | | | | 225 |

( 2 ) INFORMATION FOR SEQ ID NO: 19:

( i ) SEQUENCE CHARACTERISTICS:
    ( A ) LENGTH: 1947 base pairs
    ( B ) TYPE: nucleic acid
    ( C ) STRANDEDNESS: single
    ( D ) TOPOLOGY: linear ( i i ) MOLECULE TYPE: genomic DNA ( i x ) FEATURE:
    ( A ) NAME/KEY: MAGE-7 gene ( x i ) SEQUENCE DESCRIPTION: SEQ ID NO: 19:

| | | | | | |
|---|---|---|---|---|---|
| TGAATGGACA | ACAAGGGCCC | CACACTCCCC | AGAACACAAG | GGACTCCAGA | 50 |
| GAGCCCAGCC | TCACCTTCCC | TACTGTCAGT | CCTGCAGCCT | CAGCCTCTGC | 100 |
| TGGCCGGCTG | TACCCTGAGG | TGCCCTCTCA | CTTCCTCCTT | CAGGTTCTCA | 150 |
| GCGGACAGGC | CGGCCAGGAG | GTCAGAAGCC | CCAGGAGGCC | CCAGAGGAGC | 200 |
| ACCGAAGGAG | AAGATCTGTA | AGTAGGCCTT | TGTTAGGGCC | TCCAGGGCGT | 250 |
| GGTTCACAAA | TGAGGCCCCT | CACAAGCTCC | TTCTCTCCCC | AGATCTGTGG | 300 |
| GTTCCTCCCC | ATCGCCCAGC | TGCTGCCCGC | ACTCCAGCCT | GCTGCCCTGA | 350 |
| CCAGAGTCAT | CATGTCTTCT | GAGCAGAGGA | GTCAGCACTG | CAAGCCTGAG | 400 |
| GATGCCTTGA | GGCCCAAGGA | CAGGAGGCTC | TGGGCCTGGT | GGGTGCGCAG | 450 |
| GCTCCCGCCA | CCGAGGAGCA | CGAGGCTGCC | TCCTCCTTCA | CTCTGATTGA | 500 |
| AGGCACCCTG | GAGGAGGTGC | CTGCTGCTGG | GTCCCCAGT | CCTCCCTGA | 550 |
| GTCTCAGGGT | TCCTCCTTTT | CCCTGACCAT | CAGCAACAAC | ACTCTATGGA | 600 |
| GCCAATCCAG | TGAGGGCACC | AGCAGCCGGG | AAGAGGAGGG | GCCAACCACC | 650 |
| TAGACACACC | CCGCTCACCT | GGCGTCCTTG | TTCCA | | 685 |

| | | | | | | | | | | |
|---|---|---|---|---|---|---|---|---|---|---|
| ATG | GGA | AGG | TGG | CTG | AGT | TGG | TTC | GCT | TCC | TGC | TGC | ACA | AGT | 727 |
| ATC | GAG | TCA | AGG | AGC | TGG | TCA | CAA | AGG | CAG | AAA | TGC | TGG | ACA | 769 |
| GTG | TCA | TCA | AAA | ATT | ACA | AGC | ACT | AGT | TTC | CTT | GTG | ATC | TAT | 811 |
| GGC | AAA | GCC | TCA | GAG | TGC | ATG | CAG | GTG | ATG | TTT | GGC | ATT | GAC | 853 |
| ATG | AAG | GAA | GTG | GAC | CCC | GCG | GCC | ACT | CCT | ACG | TCC | TTG | TCA | 895 |
| CCT | GCT | TGG | GCC | TCT | CCT | ACA | ATG | GCC | TGC | TGG | GTG | ATG | ATC | 937 |
| AGA | GCA | TGC | CCG | AGA | CCG | GCC | TTC | TGA | | | | | | 964 |

| | | | | |
|---|---|---|---|---|
| TTATGGTCTT | GACCATGATC | TTAATGGAGG | GCCACTGTGC | CCCTGAGGAG | 1014 |
| GCAATCTGGG | AAGCGTTGAG | TGTAATGGTG | TATGATGGGA | TGGAGCAGTT | 1064 |
| TCTTTGGGCA | GCTGAGGAAG | CTGCTCACCC | AAGATTGGGT | GCAGGAAAAC | 1114 |
| TACCTGCAAT | ACCGCCAGGT | GCCAGCAGT | GATCCCCGT | GCTACCAGTT | 1164 |
| CCTGTGGGGT | CCAAGGGCCC | TCATTGAAAC | CAGCTATGTG | AAAGTCCTGG | 1214 |
| AGTATGCAGC | CAGGGTCAGT | ACTAAAGAGA | GCATTTCCTA | CCCATCCCTG | 1264 |
| CATGAAGAGG | CTTTGGGAGA | GGAGGAAGAG | GGAGTCTGAG | CAGAAGTTGC | 1314 |
| AGCCAGGGCC | AGTGGGGCAG | ATTGGGGGAG | GGCCTGGGCA | GTGCACGTTC | 1364 |
| CACACATCCA | CCACCTTCCC | TGTCCTGTTA | CATGAGGCCC | ATTCTTCACT | 1414 |
| CTGTGTTTGA | AGAGAGCAGT | CAATGTTCTC | AGTAGCGGGG | AGTGTGTTGG | 1464 |
| GTGTGAGGGA | ATACAAGGTG | GACCATCTCT | CAGTTCCTGT | TCTCTTGGGC | 1514 |
| GATTTGGAGG | TTTATCTTTG | TTTCCTTTTG | CAGTCGTTCA | AATGTTCCTT | 1564 |
| TTAATGGATG | GTGTAATGAA | CTTCAACATT | CATTTCATGT | ATGACAGTAG | 1614 |
| GCAGACTTAC | TGTTTTTTAT | ATAGTTAAAA | GTAAGTGCAT | TGTTTTTTAT | 1664 |
| TTATGTAAGA | AAATCTATGT | TATTTCTTGA | ATTGGGACAA | CATAACATAG | 1714 |

| | |
|---|---|
| CAGAGGATTA AGTACCTTTT ATAATGTGAA AGAACAAAGC GGTAAAATGG | 1764 |
| GTGAGATAAA GAAATAAAGA AATTAAATTG GCTGGGCACG GTGGCTCACG | 1814 |
| CCTGTAATCC CAGCACTTTA GGAGGCAGAG GCACGGGGAT CACGAGGTCA | 1864 |
| GGAGATCGAG ACCATTCTGG CTAACACAGT GAAACACCAT CTCTATTAAA | 1914 |
| AATACAAAAC TTAGCCGGGC GTGGTGGCGG GTG | 1947 |

( 2 ) INFORMATION FOR SEQ ID NO: 20:

( i ) SEQUENCE CHARACTERISTICS:
        ( A ) LENGTH: 1810 base pairs
        ( B ) TYPE: nucleic acid
        ( C ) STRANDEDNESS: single
        ( D ) TOPOLOGY: linear ( i i ) MOLECULE TYPE: genomic DNA ( i x ) FEATURE:
        ( A ) NAME/KEY: MAGE-8 gene ( x i ) SEQUENCE DESCRIPTION: SEQ ID NO: 20:

| | |
|---|---|
| GAGCTCCAGG AACCAGGCTG TGAGGTCTTG GTCTGAGGCA GTATCTTCAA | 50 |
| TCACAGAGCA TAAGAGGCCC AGGCAGTAGT AGCAGTCAAG CTGAGGTGGT | 100 |
| GTTTCCCCTG TATGTATACC AGAGGCCCCT CTGGCATCAG AACAGCAGGA | 150 |
| ACCCCACAGT TCCTGGCCCT ACCAGCCCTT TTGTCAGTCC TGGAGCCTTG | 200 |
| GCCTTTGCCA GGAGGCTGCA CCCTGAGATG CCCTCTCAAT TTCTCCTTCA | 250 |
| GGTTCGCAGA GAACAGGCCA GCCAGGAGGT CAGGAGGCCC AGAGAAGCA | 300 |
| CTGAAGAAGA CCTGTAAGTA GACCTTTGTT AGGGCATCCA GGGTGTAGTA | 350 |
| CCCAGCTGAG GCCTCTCACA CGCTTCCTCT CTCCCCAGGC CTGTGGGTCT | 400 |
| CAATTGCCCA GCTCCGGCCC ACACTCTCCT GCTGCCCTGA CCTGAGTCAT | 450 |
| C | 451 |
| ATG CTT CTT GGG CAG AAG AGT CAG CGC TAC AAG GCT GAG GAA | 493 |
| GGC CTT CAG GCC CAA GGA GAG GCA CCA GGG CTT ATG GAT GTG | 535 |
| CAG ATT CCC ACA GCT GAG GAG CAG AAG GCT GCA TCC TCC TCC | 577 |
| TCT ACT CTG ATC ATG GGA ACC CTT GAG GAG GTG ACT GAT TCT | 619 |
| GGG TCA CCA AGT CCT CCC CAG AGT CCT GAG GGT GCC TCC TCT | 661 |
| TCC CTG ACT GTC ACC GAC AGC ACT CTG TGG AGC CAA TCC GAT | 703 |
| GAG GGT TCC AGC AGC AAT GAA GAG GAG GGG CCA AGC ACC TCC | 745 |
| CCG GAC CCA GCT CAC CTG GAG TCC CTG TTC CGG GAA GCA CTT | 787 |
| GAT GAG AAA GTG GCT GAG TTA GTT CGT TTC CTG CTC CGC AAA | 829 |
| TAT CAA ATT AAG GAG CCG GTC ACA AAG GCA GAA ATG CTT GAG | 871 |
| AGT GTC ATC AAA AAT TAC AAG AAC CAC TTT CCT GAT ATC TTC | 913 |
| AGC AAA GCC TCT GAG TGC ATG CAG GTG ATC TTT GGC ATT GAT | 955 |
| GTG AAG GAA GTG GAC CCT GCC GGC CAC TCC TAC ATC CTT GTC | 997 |
| ACC TGC CTG GGC CTC TCC TAT GAT GGC CTG CTG GGT GAT GAT | 1039 |
| CAG AGT ACG CCC AAG ACC GGC CTC CTG ATA ATC GTC CTG GGC | 1081 |
| ATG ATC TTA ATG GAG GGC AGC CGC GCC CCG GAG GAG GCA ATC | 1123 |
| TGG GAA GCA TTG AGT GTG ATG GGG GCT GTA TGA | 1156 |

| | | | | |
|---|---|---|---|---|
| TGGGAGGGAG | CACAGTGTCT | ATTGGAAGCT | CAGGAAGCTG | CTCACCCAAG | 1206 |
| AGTGGGTGCA | GGAGAACTAC | CTGGAGTACC | GCCAGGCGCC | CGGCAGTGAT | 1256 |
| CCTGTGCGCT | ACGAGTTCCT | GTGGGGTCCA | AGGGCCCTTG | CTGAAACCAG | 1306 |
| CTATGTGAAA | GTCCTGGAGC | ATGTGGTCAG | GGTCAATGCA | AGAGTTCGCA | 1356 |
| TTTCCTACCC | ATCCCTGCAT | GAAGAGGCTT | TGGGAGAGGA | GAAAGGAGTT | 1406 |
| TGAGCAGGAG | TTGCAGCTAG | GGCCAGTGGG | GCAGGTTGTG | GGAGGGCCTG | 1456 |
| GGCCAGTGCA | CGTTCCAGGG | CCACATCCAC | CACTTTCCCT | GCTCTGTTAC | 1506 |
| ATGAGGCCCA | TTCTTCACTC | TGTGTTTGAA | GAGAGCAGTC | ACAGTTCTCA | 1556 |
| GTAGTGGGGA | GCATGTTGGG | TGTGAGGGAA | CACAGTGTGG | ACCATCTCTC | 1606 |
| AGTTCCTGTT | CTATTGGGCG | ATTTGGAGGT | TTATCTTTGT | TTCCTTTTGG | 1656 |
| AATTGTTCCA | ATGTTCCTTC | TAATGGATGG | TGTAATGAAC | TTCAACATTC | 1706 |
| ATTTTATGTA | TGACAGTAGA | CAGACTTACT | GCTTTTTATA | TAGTTTAGGA | 1756 |
| GTAAGAGTCT | TGCTTTTCAT | TTATACTGGG | AAACCCATGT | TATTTCTTGA | 1806 |
| ATTC | | | | | 1810 |

( 2 ) INFORMATION FOR SEQ ID NO: 21:

( i ) SEQUENCE CHARACTERISTICS:
  ( A ) LENGTH: 1412 base pairs
  ( B ) TYPE: nucleic acid
  ( C ) STRANDEDNESS: single
  ( D ) TOPOLOGY: linear ( i i ) MOLECULE TYPE: genomic DNA ( i x ) FEATURE:
  ( A ) NAME/KEY: MAGE-9 gene ( x i ) SEQUENCE DESCRIPTION: SEQ ID NO: 21:

| | | | | |
|---|---|---|---|---|
| TCTGAGACAG | TGTCCTCAGG | TCGCAGAGCA | GAGGAGACCC | AGGCAGTGTC | 50 |
| AGCAGTGAAG | GTGAAGTGTT | CACCCTGAAT | GTGCACCAAG | GGCCCCACCT | 100 |
| GCCCCAGCAC | ACATGGGACC | CCATAGCACC | TGGCCCCATT | CCCCCTACTG | 150 |
| TCACTCATAG | AGCCTTGATC | TCTGCAGGCT | AGCTGCACGC | TGAGTAGCCC | 200 |
| TCTCACTTCC | TCCCTCAGGT | TCTCGGGACA | GGCTAACCAG | GAGGACAGGA | 250 |
| GCCCCAAGAG | GCCCCAGAGC | AGCACTGACG | AAGACCTGTA | AGTCAGCCTT | 300 |
| TGTTAGAACC | TCCAAGGTTC | GGTTCTCAGC | TGAAGTCTCT | CACACACTCC | 350 |
| CTCTCTCCCC | AGGCCTGTGG | GTCTCCATCG | CCCAGCTCCT | GCCCACGCTC | 400 |
| CTGACTGCTG | CCCTGACCAG | AGTCATC | | | 427 |

| | | | | | | | | | | | | | | |
|---|---|---|---|---|---|---|---|---|---|---|---|---|---|---|
| ATG | TCT | CTC | GAG | CAG | AGG | AGT | CCG | CAC | TGC | AAG | CCT | GAT | GAA | 469 |
| GAC | CTT | GAA | GCC | CAA | GGA | GAG | GAC | TTG | GGC | CTG | ATG | GGT | GCA | 511 |
| CAG | GAA | CCC | ACA | GGC | GAG | GAG | GAG | GAG | ACT | ACC | TCC | TCC | TCT | 553 |
| GAC | AGC | AAG | GAG | GAG | GAG | GTG | TCT | GCT | GCT | GGG | TCA | TCA | AGT | 595 |
| CCT | CCC | CAG | AGT | CCT | CAG | GGA | GGC | GCT | TCC | TCC | TCC | ATT | TCC | 637 |
| GTC | TAC | TAC | ACT | TTA | TGG | AGC | CAA | TTC | GAT | GAG | GGC | TCC | AGC | 679 |
| AGT | CAA | GAA | GAG | GAA | GAG | CCA | AGC | TCC | TCG | GTC | GAC | CCA | GCT | 721 |
| CAG | CTG | GAG | TTC | ATG | TTC | CAA | GAA | GCA | CTG | AAA | TTG | AAG | GTG | 763 |
| GCT | GAG | TTG | GTT | CAT | TTC | CTG | CTC | CAC | AAA | TAT | CGA | GTC | AAG | 805 |

| | | | | | | | | | | | | | |
|---|---|---|---|---|---|---|---|---|---|---|---|---|---|
| GAG | CCG | GTC | ACA | AAG | GCA | GAA | ATG | CTG | GAG | AGC | GTC | ATC | AAA | 847 |
| AAT | TAC | AAG | CGC | TAC | TTT | CCT | GTG | ATC | TTC | GGC | AAA | GCC | TCC | 889 |
| GAG | TTC | ATG | CAG | GTG | ATC | TTT | GGC | ACT | GAT | GTG | AAG | GAG | GTG | 931 |
| GAC | CCC | GCC | GGC | CAC | TCC | TAC | ATC | CTT | GTC | ACT | GCT | CTT | GGC | 973 |
| CTC | TCG | TGC | GAT | AGC | ATG | CTG | GGT | GAT | GGT | CAT | AGC | ATG | CCC | 1015 |
| AAG | GCC | GCC | CTC | CTG | ATC | ATT | GTC | CTG | GGT | GTG | ATC | CTA | ACC | 1057 |
| AAA | GAC | AAC | TGC | GCC | CCT | GAA | GAG | GTT | ATC | TGG | GAA | GCG | TTG | 1099 |
| AGT | GTG | ATG | GGG | GTG | TAT | GTT | GGG | AAG | GAG | CAC | ATG | TTC | TAC | 1141 |
| GGG | GAG | CCC | AGG | AAG | CTG | CTC | ACC | CAA | GAT | TGG | GTG | CAG | GAA | 1183 |
| AAC | TAC | CTG | GAG | TAC | CGG | CAG | GTG | CCC | GGC | AGT | GAT | CCT | GCG | 1225 |
| CAC | TAC | GAG | TTC | CTG | TGG | GGT | TCC | AAG | GCC | CAC | GCT | GAA | ACC | 1267 |
| AGC | TAT | GAG | AAG | GTC | ATA | AAT | TAT | TTG | GTC | ATG | CTC | AAT | GCA | 1309 |
| AGA | GAG | CCC | ATC | TGC | TAC | CCA | TCC | CTT | TAT | GAA | GAG | GTT | TTG | 1351 |
| GGA | GAG | GAG | CAA | GAG | GGA | GTC | TGA | | | | | | | 1375 |

| | | | | |
|---|---|---|---|---|
| GCACCAGCCG | CAGCCGGGGC | CAAAGTTTGT | GGGGTCA | | 1412 |

( 2 ) INFORMATION FOR SEQ ID NO: 22:

( i ) SEQUENCE CHARACTERISTICS:
( A ) LENGTH: 920 base pairs
( B ) TYPE: nucleic acid
( C ) STRANDEDNESS: single
( D ) TOPOLOGY: linear ( i i ) MOLECULE TYPE: genomic DNA ( i x ) FEATURE:
( A ) NAME/KEY: MAGE-10 gene ( x i ) SEQUENCE DESCRIPTION: SEQ ID NO: 22:

| | | | | | |
|---|---|---|---|---|---|
| ACCTGCTCCA | GGACAAAGTG | GACCCCACTG | CATCAGCTCC | ACCTACCCTA | 50 |
| CTGTCAGTCC | TGGAGCCTTG | GCCTCTGCCG | GCTGCATCCT | GAGGAGCCAT | 100 |
| CTCTCACTTC | CTTCTTCAGG | TTCTCAGGGG | ACAGGGAGAG | CAAGAGGTCA | 150 |
| AGAGCTGTGG | ACACCACAG | AGCAGCACTG | AAGGAGAAGA | CCTGTAAGTT | 200 |
| GGCCTTTGTT | AGAACCTCCA | GGGTGTGGTT | CTCAGCTGTG | GCCACTTACA | 250 |
| CCCTCCCTCT | CTCCCAGGC | CTGTGGGTCC | CCATCGCCCA | AGTCCTGCCC | 300 |
| ACACTCCCAC | CTGCTACCCT | GATCAGAGTC | ATC | | 333 |

| | | | | | | | | | | | | | | |
|---|---|---|---|---|---|---|---|---|---|---|---|---|---|---|
| ATG | CCT | CGA | GCT | CCA | AAG | CGT | CAG | CGC | TGC | ATG | CCT | GAA | GAA | 375 |
| GAT | CTT | CAA | TCC | CAA | AGT | GAG | ACA | CAG | GGC | CTC | GAG | GGT | GCA | 417 |
| CAG | GCT | CCC | CTG | GCT | GTG | GAG | GAG | GAT | GCT | TCA | TCA | TCC | ACT | 459 |
| TCC | ACC | AGC | TCC | TCT | TTT | CCA | TCC | TCT | TTT | CCC | TCC | TCC | TCC | 501 |
| TCT | TCC | TCC | TCC | TCC | TCC | TGC | TAT | CCT | CTA | ATA | CCA | AGC | ACC | 543 |
| CCA | GAG | GAG | GTT | TCT | GCT | GAT | GAT | GAG | ACA | CCA | AAT | CCT | CCC | 585 |
| CAG | AGT | GCT | CAG | ATA | GCC | TGC | TCC | TCC | CCC | TCG | GTC | GTT | GCT | 627 |
| TCC | CTT | CCA | TTA | GAT | CAA | TCT | GAT | GAG | GGC | TCC | AGC | AGC | CAA | 669 |
| AAG | GAG | GAG | AGT | CCA | AGC | ACC | CTA | CAG | GTC | CTG | CCA | GAC | AGT | 711 |
| GAG | TCT | TTA | CCC | AGA | AGT | GAG | ATA | GAT | GAA | AAG | GTG | ACT | GAT | 753 |

```
TTG GTG CAG TTT CTG CTC TTC AAG TAT CAA ATG AAG GAG CCG        795

ATC ACA AAG GCA GAA ATA CTG GAG AGT GTC ATA AAA AAT TAT        837

GAA GAC CAC TTC CCT TTG TTG TTT AGT GAA GCC TCC GAG TGC        879

ATG CTG CTG GTC TTT GGC ATT GAT GTA AAG GAA GTG GAT CC         920
```

( 2 ) INFORMATION FOR SEQ ID NO: 23:

( i ) SEQUENCE CHARACTERISTICS:
        ( A ) LENGTH: 1107 base pairs
        ( B ) TYPE: nucleic acid
        ( C ) STRANDEDNESS: single
        ( D ) TOPOLOGY: linear ( i i ) MOLECULE TYPE: genomic DNA ( i x ) FEATURE:
        ( A ) NAME/KEY: MAGE-11 gene ( x i ) SEQUENCE DESCRIPTION: SEQ ID NO: 23:

```
AGAGAACAGG   CCAACCTGGA   GGACAGGAGT   CCCAGGAGAA   CCCAGAGGAT        50

CACTGGAGGA   GAACAAGTGT   AAGTAGGCCT   TTGTTAGATT   CTCCATGGTT       100

CATATCTCAT   CTGAGTCTGT   TCTCACGCTC   CCTCTCTCCC   CAGGCTGTGG       150

GGCCCCATCA   CCCAGATATT   TCCCACAGTT   CGGCCTGCTG   ACCTAACCAG       200

AGTCATCATG   CCTCTTGAGC   AAAGAAGTCA   GCACTGCAAG   CCTGAGGAAG       250

CCTTCAGGCC   CAAGAAGAAG   ACCTGGGCCT   GGTGGGTGCA   CAGGCTCTCC       300

AAGCTGAGGA   GCAGGAGGCT   GCCTTCTTCT   CCTCTACTCT   GAATGTGGGC       350

ACTCTAGAGG   AGTTGCCTGC   TGCTGAGTCA   CCAAGTCCTC   CCAGAGTCC        400

TCAGGAAGAG   TCCTTCTCTC   CCACTGCCAT   GGATGCCATC   TTTGGGAGCC       450

TATCTGATGA   GGGCTCTGGC   AGCCAAGAAA   AGGAGGGGCC   AAGTACCTCG       500

CCTGACCTGA   TAGACCCTGA   GTCCTTTTCC   CAAGATATAC   TACATGACAA       550

GATAATTGAT   TTGGTTCATT   TATTCTCCGC   AAGTATCGAG   TCAAGGGGCT       600

GATCACAAAG   GCAGAA                                                 616

ATG CTG GGG AGT GTC ATC AAA AAT TAT GAG GAC TAC TTT CCT            658

GAG ATA TTT AGG GAA GCC TCT GTA TGC ATG CAA CTG CTC TTT            700

GGC ATT GAT GTG AAG GAA GTG GAC CCC ACT AGC CAC TCC TAT            742

GTC CTT GTC ACC TCC CTC AAC CTC TCT TAT GAT GGC ATA CAG            784

TGT AAT GAG CAG AGC ATG CCC AAG TCT GGC TCC TG ATA ATA            826

GTC CTG GGT GTA ATC TTC ATG GAG GGG AAC TGC ATC CCT GAA            868

GAG GTT ATG TGG GAA GTC CTG AGC ATT ATG GGG GTG TAT GCT            910

GGA AGG GAG CAC TTC CTC TTT GGG GAG CCC AAG AGG CTC CTT            952

ACC CAA AAT TGG GTG CAG GAA AAG TAC CTG GTG TAC CGG CAG            994

GTG CCC GGC ACT GAT CCT GCA TGC TAT GAG TTC CTG TGG GGT           1036

CCA AGG GCC CAC GCT GAG ACC AGC AAG ATG AAA GTT CTT GAG           1078

TAC ATA GCC AAT GCC AAT GGG AGG GAT CC                            1107
```

( 2 ) INFORMATION FOR SEQ ID NO: 24:

( i ) SEQUENCE CHARACTERISTICS:
        ( A ) LENGTH: 2150 base pairs
        ( B ) TYPE: nucleic acid (C) STRANDEDNESS: single
(D) TOPOLOGY: linear (ii) MOLECULE TYPE: genomic DNA (ix) FEATURE:
  (A) NAME/KEY: smage-I (xi) SEQUENCE DESCRIPTION: SEQ ID NO: 24:

```
TCTGTCTGCA TATGCCTCCA CTTGTGTGTA GCAGTCTCAA ATGGATCTCT            50
CTCTACAGAC CTCTGTCTGT GTCTGGCACC CTAAGTGGCT TTGCATGGGC           100
ACAGGTTTCT GCCCCTGCAT GGAGCTTAAA TAGATCTTTC TCCACAGGCC           150
TATACCCCTG CATTGTAAGT TTAAGTGGCT TTATGTGGAT ACAGGTCTCT           200
GCCCTTGTAT GCAGGCCTAA GTTTTCTGT CTGCTTAACC CCTCCAAGTG            250
AAGCTAGTGA AAGATCTAAC CCACTTTGG AAGTCTGAAA CTAGACTTTT            300
ATGCAGTGGC CTAACAAGTT TTAATTTCTT CCACAGGGTT TGCAGAAAAG           350
AGCTTGATCC ACGAGTTCAG AAGTCCTGGT ATGTTCCTAG AAAG                 394
ATG TTC TCC TGG AAA GCT TCA AAA GCC AGG TCT CCA TTA AGT          436
CCA AGG TAT TCT CTA CCT GGT AGT ACA GAG GTA CTT ACA GGT          478
TGT CAT TCT TAT CCT TCC AGA TTC CTG TCT GCC AGC TCT TTT          520
ACT TCA GCC CTG AGC ACA GTC AAC ATG CCT AGG GGT CAA AAG          562
AGT AAG ACC CGC TCC CGT GCA AAA CGA CAG CAG TCA CGC AGG          604
GAG GTT CCA GTA GTT CAG CCC ACT GCA GAG GAA GCA GGG TCT          646
TCT CCT GTT GAC CAG AGT GCT GGG TCC AGC TTC CCT GGT GGT          688
TCT GCT CCT CAG GGT GTG AAA ACC CCT GGA TCT TTT GGT GCA          730
GGT GTA TCC TGC ACA GGC TCT GGT ATA GGT GGT AGA AAT GCT          772
GCT GTC CTG CCT GAT ACA AAA AGT TCA GAT GGC ACC CAG GCA          814
GGG ACT TCC ATT CAG CAC ACA CTG AAA GAT CCT ATC ATG AGG          856
AAG GCT AGT GTG CTG ATA GAA TTC CTG CTA GAT AAA TTT AAG          898
ATG AAA GAA GCA GTT ACA AGG AGT GAA ATG CTG GCA GTA GTT          940
AAC AAG AAG TAT AAG GAG CAA TTC CCT GAG ATC CTC AGG AGA          982
ACT TCT GCA CGC CTA GAA TTA GTC TTT GGT CTT GAG TTG AAG         1024
GAA ATT GAT CCC AGC ACT CAT TCC TAT TTG CTG GTA GGC AAA         1066
CTG GGT CTT TCC ACT GAG GGA AGT TTG AGT AGT AAC TGG GGG         1108
TTG CCT AGG ACA GGT CTC CTA ATG TCT GTC CTA GGT GTG ATC         1150
TTC ATG AAG GGT AAC CGT GCC ACT GAG CAA GAG GTC TGG CAA         1192
TTT CTG CAT GGA GTG GGG TAT GCT GGG AAG AAG CAC TTG             1234
ATC TTT GGC GAG CCT GAG GAG TTT ATA AGA GAT GTA GTG CGG         1276
GAA AAT TAC CTG GAG TAC CGC CAG GTA CCT GGC AGT GAT CCC         1318
CCA AGC TAT GAG TTC CTG TGG GGA CCC AGA GCC CAT GCT GAA         1360
ACA ACC AAG ATG AAA GTC CTG GAA GTT TTA GCT AAA GTC AAT         1402
GGC ACA GTC CCT AGT GCC TTC CCT AAT CTC TAC CAG TTG GCT         1444
CTT AGA GAT CAG GCA GGA GGG GTG CCA AGA AGG AGA GTT CAA         1486
GGC AAG GGT GTT CAT TCC AAG GCC CCA TCC CAA AAG TCC TCT         1528
```

| | | | | | |
|---|---|---|---|---|---|
| AAC ATG TAG | | | | | 1537 |
| TTGAGTCTGT | TCTGTTGTGT | TTGAAAAACA | GTCAGGCTCC | TAATCAGTAG | 1587 |
| AGAGTTCATA | GCCTACCAGA | ACCAACATGC | ATCCATTCTT | GGCCTGTTAT | 1637 |
| ACATTAGTAG | AATGGAGGCT | ATTTTGTTA | CTTTTCAAAT | GTTTGTTTAA | 1687 |
| CTAAACAGTG | CTTTTTGCCA | TGCTTCTTGT | TAACTGCATA | AAGAGGTAAC | 1737 |
| TGTCACTTGT | CAGATTAGGA | CTTGTTTTGT | TATTTGCAAC | AAACTGGAAA | 1787 |
| ACATTATTTT | GTTTTACTA | AACATTGTG | TAACATTGCA | TTGGAGAAGG | 1837 |
| GATTGTCATG | GCAATGTGAT | ATCATACAGT | GGTGAAACAA | CAGTGAAGTG | 1887 |
| GGAAAGTTTA | TATTGTTAAT | TTTGAAAATT | TTATGAGTGT | GATTGCTGTA | 1937 |
| TACTTTTTTC | TTTTTTGTAT | AATGCTAAGT | GAAATAAAGT | TGGATTTGAT | 1987 |
| GACTTTACTC | AAATTCATTA | GAAAGTAAAT | CGTAAAACTC | TATTACTTTA | 2037 |
| TTATTTTCTT | CAATTATGAA | TTAAGCATTG | GTTATCTGGA | AGTTTCTCCA | 2087 |
| GTAGCACAGG | ATCTAGTATG | AAATGTATCT | AGTATAGGCA | CTGACAGTGA | 2137 |
| GTTATCAGAG | TCT | | | | 2150 |

( 2 ) INFORMATION FOR SEQ ID NO: 25:

( i ) SEQUENCE CHARACTERISTICS:
        ( A ) LENGTH: 2099 base pairs
        ( B ) TYPE: nucleic acid
        ( C ) STRANDEDNESS: single
        ( D ) TOPOLOGY: linear ( i i ) MOLECULE TYPE: genomic DNA ( i x ) FEATURE:
        ( A ) NAME/KEY: smage-II ( x i ) SEQUENCE DESCRIPTION: SEQ ID NO: 25:

| | | | | | |
|---|---|---|---|---|---|
| ACCTTATTGG | GTCTGTCTGC | ATATGCCTCC | ACTTGTGTGT | AGCAGTCTCA | 50 |
| AATGGATCTC | TCTCTACAGA | CCTCTGTCTG | TGTCTGGCAC | CCTAAGTGGC | 100 |
| TTTGCATGGG | CACAGGTTTC | TGCCCCTGCA | TGGAGCTTAA | ATAGATCTTT | 150 |
| CTCCACAGGC | CTATACCCCT | GCATTGTAAG | TTTAAGTGGC | TTTATGTGGA | 200 |
| TACAGGTCTC | TGCCCTTGTA | TGCAGGCCTA | AGTTTTCTG | TCTGCTTAGC | 250 |
| CCCTCCAAGT | GAAGCTAGTG | AAAGATCTAA | CCCACTTTTG | GAAGTCTGAA | 300 |
| ACTAGACTTT | TATGCAGTGG | CCTAACAAGT | TTTAATTTCT | TCCACAGGGT | 350 |
| TTGCAGAAAA | GAGCTTGATC | CACGAGTTCG | GAAGTCCTGG | TATGTTCCTA | 400 |
| GAAAGATGTT | CTCCTGGAAA | GCTTCAAAAG | CCAGGTCTCC | ATTAAGTCCA | 450 |
| AGGTATTCTC | TACCTGGTAG | TACAGAGGTA | CTTACAGGTT | GTCATTCTTA | 500 |
| TCTTTCCAGA | TTCCTGTCTG | CCAGCTCTTT | TACTTCAGCC | CTGAGCACAG | 550 |
| TCAACATGCC | TAGGGGTCAA | AAGAGTAAGA | CCCGCTCCCG | TGCAAAACGA | 600 |
| CAGCAGTCAC | GCAGGGAGGT | TCCAGTAGTT | CAGCCCACTG | CAGAGGAAGC | 650 |
| AGGGTCTTCT | CCTGTTGACC | AGAGTGCTGG | GTCCAGCTTC | CCTGGTGGTT | 700 |
| CTGCTCCTCA | GGGTGTGAAA | ACCCCTGGAT | CTTTTGGTGC | AGGTGTATCC | 750 |
| TGCACAGGCT | CTGGTATAGG | TGGTAGAAAT | GCTGCTGTCC | TGCCTGATAC | 800 |
| AAAAAGTTCA | GATGGCACCC | AGGCAGGGAC | TTCCATTCAG | CACACACTGA | 850 |
| AAGATCCTAT | CATGAGGAAG | GCTAGTGTGC | TGATAGAATT | CCTGCTAGAT | 900 |

| | | | | |
|---|---|---|---|---|
| AAGTTTAAGA | TGAAAGAAGC | AGTTACAAGG | AGTGAAATGC | TGGCAGTAGT | 950
| TAACAAGAAG | TATAAGGAGC | AATTCCCTGA | GATCCTCAGG | AGAACTTCTG | 1000
| CACGCCTAGA | ATTAGTCTTT | GGTCTTGAGT | TGAAGGAAAT | TGATCCCAGC | 1050
| ACTCATTCCT | ATTTGCTGGT | AGGCAAACTG | GGTCTTTCCA | CTGAGGGAAG | 1100
| TTTGAGTAGT | AACTGGGGGT | TGCCTAGGAC | AGGTCTCCTA | ATGTCTGTCC | 1150
| TAGGTGTGAT | CTTCATGAAG | GGTAACCGTG | CCACTGAGCA | AGAGGTCTGG | 1200
| CAATTTCTGC | ATGGAGTGGG | GGTATATGCT | GGGAAGAAGC | ACTTGATCTT | 1250
| TGGCGAGCCT | GAGGAGTTTA | TAAGAGATGT | AGTGCGGGAA | AATTACCTGG | 1300
| AGTACCGCCA | GGTACCTGGC | AGTGATCCCC | CAAGCTATGA | GTTCCTGTGG | 1350
| GGACCCAGAG | CCCATGCTGA | AACAACCAAG | ATGAAAGTCC | TGGAAGTTTT | 1400
| AGCTAAAGTC | AATGGCACAG | TCCCTAGTGC | CTTCCCTAAT | CTCTACCAGT | 1450
| TGGCTCTTAG | AGATCAGGCA | GGAGGGGTGC | CAAGAAGGAG | AGTTCAAGGC | 1500
| AAGGGTGTTC | ATTCCAAGGC | CCCATCCCAA | AAGTCCTCTA | ACATGTAGTT | 1550
| GAGTCTGTTC | TGTTGTGTTT | GAAAAACAGT | CAGGCTCCTA | ATCAGTAGAG | 1600
| AGTTCATAGC | CTACCAGAAC | CAACATGCAT | CCATTCTTGG | CCTGTTATAC | 1650
| ATTAGTAGAA | TGGAGGCTAT | TTTTGTTACT | TTTCAAATGT | TTGTTTAACT | 1700
| AAACAGTGCT | TTTTGCCATG | CTTCTTGTTA | ACTGCATAAA | GAGGTAACTG | 1750
| TCACTTGTCA | GATTAGGACT | TGTTTTGTTA | TTTGCAACAA | ACTGGAAAAC | 1800
| ATTATTTTGT | TTTTACTAAA | ACATTGTGTA | ACATTGCATT | GGAGAAGGGA | 1850
| TTGTCATGGC | AATGTGATAT | CATACAGTGG | TGAAACAACA | GTGAAGTGGG | 1900
| AAAGTTTATA | TTGTTAGTTT | TGAAAATTTT | ATGAGTGTGA | TTGCTGTATA | 1950
| CTTTTTTCTT | TTTTGTATAA | TGCTAAGTGA | AATAAAGTTG | GATTGATGA | 2000
| CTTTACTCAA | ATTCATTAGA | AAGTAAATCA | TAAAACTCTA | TTACTTTATT | 2050
| ATTTTCTTCA | ATTATTAATT | AAGCATTGGT | TATCTGGAAG | TTTCTCCAG | 2099

( 2 ) INFORMATION FOR SEQ ID NO: 26:

( i ) SEQUENCE CHARACTERISTICS:
        ( A ) LENGTH: 9 amino acids
        ( B ) TYPE: amino acids
        ( D ) TOPOLOGY: linear ( i i ) MOLECULE TYPE: protein ( x i ) SEQUENCE DESCRIPTION: SEQ ID NO: 26:

Glu  Ala  Asp  Pro  Thr  Gly  His  Ser  Tyr
                        5

( 2 ) INFORMATION FOR SEQ ID NO: 27:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 27:

TGGAGGACCA  GAGGCCCCC                                                    19

( 2 ) INFORMATION FOR SEQ ID NO: 28:

( i ) SEQUENCE CHARACTERISTICS:

(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 28:

GGACGATTAT CAGGAGGCCT GC   22

(2) INFORMATION FOR SEQ ID NO: 29:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 29:

GAGCAGACAG GCCAACCG   18

(2) INFORMATION FOR SEQ ID NO: 30:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 30:

AAGGACTCTG CGTCAGGC   18

(2) INFORMATION FOR SEQ ID NO: 31:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 31:

CTAGAGGAGC ACCAAAGGAG AAG   23

(2) INFORMATION FOR SEQ ID NO: 32:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 32:

TGCTCGGAAC ACAGACTCTG G   21

(2) INFORMATION FOR SEQ ID NO: 33:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO: 33:

TGGAGGACCA GAGGCCCCC   19

(2) INFORMATION FOR SEQ ID NO: 34:

(i) SEQUENCE CHARACTERISTICS:
(A) LENGTH: 24 base pairs
(B) TYPE: nucleic acid ( C ) STRANDEDNESS: single
( D ) TOPOLOGY: linear ( x i ) SEQUENCE DESCRIPTION: SEQ ID NO: 34:

CAGGATGATT ATCAGGAAGC CTGT 24

( 2 ) INFORMATION FOR SEQ ID NO: 35:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO: 35:

CAGAGGAGCA CCGAAGGAGA A 21

( 2 ) INFORMATION FOR SEQ ID NO: 36:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO: 36:

CAGGTGAGCG GGGTGTGTC 19

( 2 ) INFORMATION FOR SEQ ID NO: 37:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO: 37:

CCCCAGAGAA GCACTGAAGA AG 22

( 2 ) INFORMATION FOR SEQ ID NO: 38:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 38:

GGTGAGCTGG GTCCGGG 17

( 2 ) INFORMATION FOR SEQ ID NO: 39:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO: 39:

CCCCAGAGCA GCACTGACG 19

( 2 ) INFORMATION FOR SEQ ID NO: 40:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO: 40:

CAGCTGAGCT GGGTCGACC 19

( 2 ) INFORMATION FOR SEQ ID NO: 41:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 41:

CACAGAGCAG CACTGAAGGA G 21

( 2 ) INFORMATION FOR SEQ ID NO: 42:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 42:

CTGGGTAAAG ACTCACTGTC TGG 23

( 2 ) INFORMATION FOR SEQ ID NO: 43:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 43:

GAGAACCCAG AGGATCACTG GA 22

( 2 ) INFORMATION FOR SEQ ID NO: 44:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 44:

GGGAAAAGGA CTCAGGGTCT ATC 23

( 2 ) INFORMATION FOR SEQ ID NO: 45:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 45:

GGTGGAAGTG GTCCGCATCG 20

( 2 ) INFORMATION FOR SEQ ID NO: 46:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 46:

GCCCTCCACT GATCTTTAGC AA 22

(2) INFORMATION FOR SEQ ID NO: 47:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 47:

ACTCAGCTCC TCCCAGATTT 20

(2) INFORMATION FOR SEQ ID NO: 48:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 48:

GAAGAGGAGG GGCCAAG 17